United States Patent
Vacher et al.

(10) Patent No.: US 7,109,234 B2
(45) Date of Patent: Sep. 19, 2006

(54) BENZOXATHIEPINE DERIVATIVES AND THEIR USE AS MEDICINES

(75) Inventors: Bernard Vacher, Castres (FR); Florence Castan-Cuisat, Castres (FR); Gareth John, Castres (FR); Bruno Legrand, Lautrec (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 160 days.

(21) Appl. No.: 10/472,728

(22) PCT Filed: Mar. 20, 2002

(86) PCT No.: PCT/FR02/00969

§ 371 (c)(1),
(2), (4) Date: Sep. 22, 2003

(87) PCT Pub. No.: WO02/081464

PCT Pub. Date: Oct. 17, 2002

(65) Prior Publication Data

US 2004/0127552 A1  Jul. 1, 2004

(30) Foreign Application Priority Data

Mar. 22, 2001 (FR) .................... 01 03877

(51) Int. Cl.
  *A61K 31/38* (2006.01)
  *C07D 327/00* (2006.01)
(52) U.S. Cl. ........................ 514/431; 549/10
(58) Field of Classification Search ............. 549/10; 514/431

See application file for complete search history.

(56) References Cited

U.S. PATENT DOCUMENTS 4,751,316 A * 6/1988 Sugihara et al. ............. 549/10
5,538,974 A * 7/1996 Ogawa et al. ......... 514/252.13

* cited by examiner

Primary Examiner—Taofiq Solola
Assistant Examiner—Robert Shiao
(74) *Attorney, Agent, or Firm*—Hueschen and Sage

(57) ABSTRACT

The invention concerns 3-arylthio-propyl-amino-3,4-dihydro-2H-1,5-aryloxathiepin derivatives of general formula (I), wherein: R1 and R2, identical or different, represent a hydrogen atom, a fluorine atom or a chlorine atom, a hydroxy group, an alkyl, cyclopropyl, alkoxy, cyclopropoxy radical or when they occupy adjacent positions, form with the carbon atoms bearing them a carbon-containing cycle or an oxygen-containing heterocycle with five non-aromatic rings; R3 represents an alkyl radical, a hydroxy group or a methoxy radical; R4 represents a hydrogen atom or a methyl radical; and R5 and R6, identical or different represent a hydrogen atom, an alkyl, alkoxy, alkylthio, alkylamino radical, or the groups OR4 and R5 form with the carbons which bear them a non-aromatic heterocycle with five or six rings containing at least an oxygen atom; and their pharmaceutically acceptable additions salts (I)

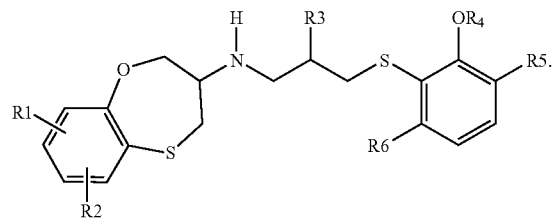

13 Claims, No Drawings

BENZOXATHIEPINE DERIVATIVES AND THEIR USE AS MEDICINES

This application is 371 of PCT/FR02/00969 filed on Mar. 20, 2002, which claims benefit of the foreign application, FRANCE 01/03877 filed on Mar. 22, 2001.

A subject matter of the present invention is 3-arylthiopropylamino-3,4-dihydro-2H-1,5-benzoxathiepine derivatives, their process of preparation and their use as medicaments.

Indole derivatives of formula:

in which:
$R_1 = C_3–C_{12}$ cycloalkyl or poly($C_3–C_{12}$)cycloalkyl;
$A = (CH_2)_n CO$, $SO_2$, $S(O)$, $NHCO$, $(CH_2)_n COO$, $SCO$, $O(CH_2)_n CO$ or $HC=CHCO$;
$R'_2 = C_1–C_6$ alkyl, $HC=CH_2$, $CCH$, $(CH_2)_n CH=CH_2$, $(CH_2)_n CCH$, $(CH_2)_n Ar$, $(CH_2)_n OR'$, $(CH_2)_n OAr$, $(CH_2)_n CO_2 R'$ or $(CH_2)_n NR_5 R_6$;
$R_9 = H$, $C_1–C_6$ alkyl, $(CH_2)_n CO_2 R'$, $(CH_2)_n OAr$, $(CH_2)_n Ar$ or $(CH_2)_n NR_5 R_6$;
$R'_{12} = R'_{13} = R'_{14} =$ halogen;
X and $Y = O$, S, N, $CH_2$, $CHR_{12}$, $NR_{12}$, $NR_{12} CO$, CN, $C=C$, CO or a bond;
$w = 0$ or 1; $n = n' = 0–6$;
$R_5$ and $R_6 = H$ or $C_1–C_6$ alkyl;
$R' = H$ or $C_1–C_6$ alkyl;
Ar = carbon- or heteroaromatic, carbo- or heterocyclic, mono- or polycyclic residue;
$R_{12} = H$;

are claimed in international application WO 93/03721 as colecystokinin antagonists of use in the treatment of depression.

3-Oxo-3,4-dihydro-2H-1,5-benzoxathiepines of formula:

in which:
$R_1$ and $R_2 = H$, alkyl, alkoxy, OH or halo;
$R_3$ and $R_4 = H$, alkyl, cycloalkyl, aralkyl or heterocyclic;
$X = H$, $CO_2 H$, alkyl or aryl;
$Y = (C=O)$ or $CH_2 OR_5$;
$m = 0–2$; $n = 1–6$;
$R_5 = H$, $C_1–C_6$ alkyl, phenyl($C_1–C_6$)alkyl which is unsubstituted or substituted by 1 to 3 halogen atoms or a $C_1–C_4$ alkyl or $C_1–C_4$ alkoxy or methylenedioxy or amino or nitro or hydroxyl group; a unsubstituted carbamoyl group or a carbamoyl group substituted by a group which is $C_1–C_4$ alkyl, unsubstituted phenyl or phenyl substituted by 1 to 3 halogen atoms or $C_1–C_4$ alkyl or $C_1–C_4$ alkoxy or methylenedioxy or amino or nitro or hydroxyl; a unsubstituted phenyl($C_1–C_4$)alkyl group or a phenyl ($C_1–C_4$)alkyl group substituted by 1 to 3 halogen atoms or $C_1–C_4$ alkyl or $C_1–C_4$ alkoxy or methylenedioxy or amino or nitro or hydroxyl, are claimed in patents EP 300 088 and EP 145 494 and in international application WO 85/02617 both as serotonin 5-HT$_2$ receptor subtype antagonists and calcium channel antagonists. The same compounds are claimed in patent EP 667 156 as agents of use in the treatment of ocular diseases.

The preparation of 3-amino-3,4-dihydro-2H-1,5-benzoxathiepine-4-carbonitriles of formula:

in which:
$R = H$, $OCH_3$, $CH_3$ or Cl;

is disclosed in Chem. Pharm. Bull., 1987, 35, 1919 and WO 85/02617.

1,5-Benzoxathiepine-2-one-4-aryls are reported as benzodiazepine analogs in Synth. Commun., 1996, 26, 4459 and Med. Sci. Res., 1996, 24, 589.

4-Hydroxy-1,5-benzoxathiepines are described in Phosphorus Sulfur, 1983, 14, 151 and J. Heterocyclic. Chem., 1994, 31, 1151.

1,5-Benzoxathiepine-2,4-diones are reported in J. Heterocyclic. Chem., 1982, 19, 1241 and Rapid Commun. Mass Spectrom., 1991, 5, 137.

Variously substituted 2,3-dihydro-1,4-benzothiazepines, related to diltiazem, are described in J. Org. Chem., 1999, 64, 2219. Others are claimed as bradykinin receptor agonists (FR 2 756 566; J. Med. Chem., 2000, 43, 2382 and 2387) or as neuropeptide Y inhibitors (WO 98/35941) or as conversion enzyme inhibitors (U.S. Pat. No. 5,723,457).

Diphosphonic acids of formula:

in which:
$R_1$ and $R_2$ represent, independently of one another, a hydrogen atom, a $C_1–C_7$ alkyl radical, a $C_1–C_7$ alkoxy radical, a halogen or a trifluoromethyl group;
$R_3$ represents a hydrogen atom or a $C_1–C_7$ alkyl radical;
X and Y represent, independently of one another, a sulfur or oxygen atom;
$R'_1$ and $R'_2$, which are identical or different, represent a $C_1–C_7$ alkoxy radical;
$n = 0$ or 1; m and m', independently of one another, $= 0$, 1 or 2, the sum n, m and m'$= 1$, 2 or 3;

are claimed in patent EP 481 920 as calcium exchange regulators.

1,5-Benzoxathiepine derivatives of formula:

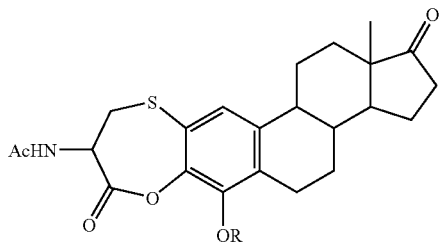

are described in Steroids, 1998, 63(12), 672 and 1996, 61(5), 296 and are used as pharmacokinetic tools.

3-Arylthiopropylamino-3,4-dihydro-2H-1,5-benzoxathiepine derivatives have never been described as being openers, activators, agonists, modulators, blockers, inhibitors or antagonists of voltage-dependent sodium channels.

Coronary insufficiency, which encompasses various pathologies (e.g. silent ischemia, stable angina, unstable angina, myocardial infarction, and the like), constitutes one of the main causes of morbidity and mortality in the industrialized world. The aging of the population should further contribute to aggravating the situation in the years to come (Nature Medecine, 1998, 4, 1241). In coronary insufficiency, the condition of the contractile function is the main determinant of the prognosis. In point of fact, the attack on the contractile function can only be limited by treatments which preserve the viability of the cardiomyocytes in the region compromised by the ischemia.

Two principles make it possible to postpone the death of the cardiac cells exposed to the ischemia and thus to limit the subsequent degree of dysfunction:

rapid reoxygenation of the tissue;

maintenance of the ionic homeostasis of the cells.

While, on the one hand, the progress achieved in blood clot therapy and in cardiac surgery have had a positive impact, quantifiable in terms of clinical benefits (Lancet, 1994, 343, 311; Arch. Intern. Med., 1996, 156, 1382), on the other hand, the contribution made by cytoprotective agents per se is currently virtually nonexistent (Scrip Magazine, November 1998, p. 15).

This is because the medicaments used in coronary insufficiency (e.g., beta-blockers, calcium inhibitors, nitro derivatives) all act indirectly, mainly by a hemodynamic phenomenon. Thus, nitro derivatives act by venous and coronary vasodilation, beta-blockers reduce the heart rate and thus cardiac work and calcium channel inhibitors improve cardiac perfusion. Nicorandil, which is both a nitrate and an activator of ATP-dependent potassium channels, is a vasodilator and reduces cardiac work (Eur. Heart J., 1999, 20, 51; Drugs, 2000, 60(4), 955). Trimetazidine has vasodilating effects and acts on the energy metabolism of cells exposed to ischemia (Dictionnaire Vidal®, 74th edition, p. 1940, 1998).

It follows that medicaments capable of directly protecting the cardiac cell in a situation of ischemia (chronic or acute) and therefore of contributing to preserving the cardiac function in the absence of a significant hemodynamic effect are highly desirable.

The mechanisms involved in cell death and those which oppose the recovery of the cardiac function after the reestablishment of the blood circulation are many and complex. This is because their relative contributions vary over time and their effects are additive. Nevertheless, it is accepted that myocardial ischemia disrupts, inter alia, the operation of the sodium channels and of the $Na^+/K^+$ pump. The latter constitutes the main mechanism for the expulsion of $Na^+$ ions in cardiac cells (J. Mol. Cell Cardiol., 1998, 30, 337). These combined effects are probably involved in the intracellular accumulation of sodium ions observed during ischemia (Circ. Res., 1999, 84, 1401). This intracellular accumulation of sodium ions induces, via the sodium-calcium exchanger, a calcium overload already during the ischemic episode and which is further enhanced during the reperfusion process (Circulation, 1994, 90, 391; J. Mol. Cell. Cardiol., 2000, 32, 1169). The excessive rise in the intra-cellular concentration of calcium ion reduces the contractility and weakens the cytoskeleton. A contraction can result therefrom and can lead to the death of the cardiac cell. Furthermore, the contraction of a cell can damage the adjacent cells and further extend the region of necrosis inside the tissue (Circ. Res., 1999, 85, 280; News Physiol. Sc., 2000, 15, 326). The detrimental change in the contractile function of the exposed cardiac cells is reflected overall by a detrimental change in the cardiac function.

In view of the major role played by the sodium overload in the initiation of processes resulting in the death of the cardiac myocyte, numerous compounds targeted at preventing it have been described (Pharmacol. Res., 1999, 39, 169). Currently, two different routes of entry of sodium ions into the cell are the subject of attempts at therapeutic interventions: the voltage-dependent sodium channel and the sodium-proton exchanger, although the role of the latter during the ischemic episode is disputed (J. Mol. Cell. Cardiol., 1998, 30, 829; Circulation, 2000, 102, 1977; J. Mol. Cell Cardiol., 2000, 32, 1897). The $Na^+/HCO_3^-$ cotransporter constitutes a third route of entry of $Na^+$ ions into the cell but its contribution during ischemia is currently unknown (Am. J. Physiol., 1999, 276, C576).

Several inhibitors of the sodium-proton exchanger are described, such as, for example, the compounds FR 183998 and FR 168888 (Fujisawa), SM-20550 (Sumitomo), KB-R9032 (Organon), MS-31-038 (Mitsui), EMD-96785 (Merck KgaA), cariporide (Aventis), TY-12533 (Eur. J. Pharmacol., 2000, 404, 221), BIIB-513 (Am. J. Physiol., 2000, 279, H1563) and those which are subjects of the international applications WO 99/43663, WO 99/61414 and WO 99/55690. However, the clinical benefit of this class of compounds in coronary diseases remains to be confirmed (Circulation, 2000, 102, 3032).

Voltage-dependent sodium channel blockers, for their part, have formed the subject of intense research for several decades. A large number of compounds are consequently available. The latter can be divided into three main subclasses according to their mode of interaction with the sodium channels.

The first subclass combines together class I antiarrhythmics, local anesthetics and some anticonvulsants (Trends in Pharmacological Science, 1992, 13, 352). Several representatives of this subclass are available clinically. Class I antiarrhythmics, local anesthetics and some anticonvulsants, such as, for example, lidocaine, phenytoin, flecainide and quinidine, have a common site of interaction at the cardiac and neuronal sodium channels (Proc. Natl. Acad. Sci. USA, 1996, 93, 9270). Nevertheless, these agents exert no or exert only a slight cardiac cytoprotective activity. Furthermore, their use in the treatment of coronary diseases presents a high risk of side effects. This is because it has been shown clinically that compounds such as encainide and flecainide have a high arrhythmogenic potential when the electrophysiological conditions are detrimentally affected, such as, for example, during ischemia (Am. J. Cardiol., 1996, 7 (supp. 4A); 12).

The second subclass comprises blockers or modulators of neuronal sodium channels which do not appear to significantly affect cardiac voltage-dependent sodium channels. The compounds belonging to this subclass are mainly claimed for the treatment of diseases and disorders of the central and/or peripheral nervous system (Exp. Opin. Pharmacother., 1999, 1, 61; Brain Res. Rev., 1998, 26, 16; Trends in Pharmacological Science, 1995, 16, 309). This subclass combines together compounds of various chemical categories (Ion Channel Modulator, 1997, 12, 594; Annual Reports in Medicinal Chemistry, 1998, 33, 51; J. Med. Chem., 2001, 44, 115), M50463 (Brain Res., 1999, 815, 131), NS-7 (Naunyn-Schmiedeberg's Arch. Pharmacol., 1997, 355, 601), T-477 (Eur. J. Pharmacol., 2000, 398(2), 209), SUN N8075 (J. Med. Chem., 2000, 43, 3372), certain arylpiperidine derivatives (Bioorg. Med. Chem. Lett., 1999, 9, 2999), certain arylpiperidinopropanol derivatives (WO 99/23072), certain piperidinol derivatives (WO 00/61558), certain pyrazine derivatives (WO 98/38174), certain N,N-diarylguanidine derivatives (J. Med. Chem., 1998, 41, 3298), certain benzoylguanidine derivatives (EP 822 182), certain sulfonylcyanamide derivatives (DE 19820064 and DE 19804251), certain 4-aminopyridine derivatives (Drug Dev. Res., 1998, 44, 8), certain 3-aminopyrrole derivatives (J. Med. Chem., 1998, 41, 63), certain aryl(aromatic heterocycle) derivatives (WO 00/57877), certain 5-naphth-1-yl-1, 3-dioxane derivatives (WO 98/55474), certain chroman derivatives (WO 98/47889), certain cyclic ether derivatives (WO 98/08842), certain quinone derivatives (WO 97/07109), certain derivatives of heterocycles substituted by diphenyl groups (DE 19816880), certain benzomorphan derivatives (DE 19740110) and certain benzindole derivatives (DE 19834714). The advantage of these derivatives as cardiac cytoprotective agents appears to be limited.

The third subclass comprises compounds which act at the cardiac sodium channels but via a different mechanism from that of class I antiarrhythmic agents. This is because they block the noninactivated sodium channel and thus reduce the slow inactivation component of the sodium current. This is the case with the derivative R 56865, originally developed as antianoxic/antihypoxic agent (EP 0 184 257), the cardioprotective action of which via the voltage-dependent sodium channel was only revealed subsequently (J. Cardiovasc. Pharmacol., 1998, 31, 800). Other derivatives, claimed inter alia as cardiac cytoprotective agents, might form part of this subclass. They are, for example, the derivative CRE-319M2 (Naunyn-Schmiedeberg's Arch. Pharmacol., 1998, 358 (supp. 2), 508), 1-cis-diltiazem (Eur. J. Pharmacol., 2000, 391, 217), KC 12291 (Naunyn-Schmiedeberg's Arch. Pharmacol., 1998, 358, 554), CP-060S (J. Cardiovasc. Pharmacol., 1999, 33, 70), ST-6 (Drug Data Report, 2000, 22, 790), the benzofuranones disclosed in international application WO 96/12718, the benzo(thia/oxa)zines disclosed in international applications WO 97/05134 and WO 00/43391, and the arylisothioureas disclosed in international application WO 00/43011.

However, although the compounds belonging to the third subclass exhibit a high potential as cardiac cytoprotective agents, none is entirely satisfactory:
either because of their inadequate selectivity with regard to the other voltage-dependent ion channels, in particular the $K^+$ and/or $Ca^{++}$ channels;
or because of their inadequate selectivity with regard to neuronal and/or (skeletal and/or smooth) muscle voltage-dependent sodium channels;
or because of their inadequate selectivity with regard to the fast inactivation component of the sodium current;
or because of their interaction with other receptor and/or enzyme systems.

The development of novel molecules, belonging to the third subclass but more selective than the prior molecules, is therefore highly desirable.

In point of fact, the inventors have discovered, surprisingly, that compounds derived from 3-aryl-thiopropylamino-3,4-dihydro-2H-1,5-benzoxathiepine can specifically oppose the sodium overload induced by ischemia by acting directly and selectively on the noninactivated voltage-dependent sodium channel. Such compounds, capable of alleviating the sodium overload induced by ischemia, are cytoprotective and therefore cardioprotective overall and, for this reason, are potentially of use in the treatment of diseases related to a sodium overload, in particular coronary insufficiency, for which there exists a great therapeutic need.

A subject matter of the present invention is thus a novel family of compounds which correspond to the general formula (1)

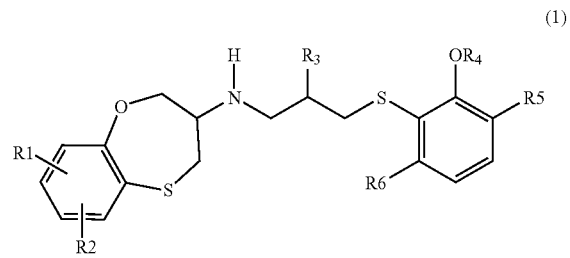

in which
$R_1$ and $R_2$, which are identical or different, represent:
  a hydrogen atom;
  a fluorine atom or a chlorine atom;
  a hydroxyl group;
  a linear or branched alkyl radical including from 1 to 3 carbon atoms;
  a cyclopropyl radical;
  a cyclopropoxy radical; or
  when the $R_1$ and $R_2$ groups occupy adjacent positions on the aromatic ring, then they form, with the carbon atoms which carry them, a nonaromatic five-membered oxygen-comprising heterocycle or carbonaceous ring;
$R_3$ represents:
  a linear or branched alkyl radical including from 1 to 3 carbon atoms;
  a hydroxyl group or a methoxy radical;
$R_4$ represents:
  a hydrogen atom or a methyl radical; and
$R_5$ and $R_6$, which are identical or different, represent:
  a hydrogen atom;
  a linear or branched alkyl radical including from 1 to 3 carbon atoms;
  a linear or branched alkoxy radical including from 1 to 3 carbon atoms;
  a linear or branched alkylthio radical including from 1 to 3 carbon atoms;
  an alkylamino radical;

provided that, when R₄ represents a methyl radical, then R₅ represents a hydrogen atom, an alkoxy radical including from 1 to 3 carbon atoms, a linear or branched alkylthio radical including from 1 to 3 carbon atoms or an alkylamino radical, or the OR₄ and R₅ groups form, with the carbons which carry them, a nonaromatic five- or six-membered heterocycle comprising at least one oxygen atom, and R₆ is as defined above, their addition salts and the hydrates of these addition salts with inorganic acids or organic acids pharmaceutically acceptable, and their tautomeric forms, the enantiomers and the mixtures of enantiomers, and the stereoisomers, pure or as a racemic or nonracemic mixture.

A more particular subject matter of the invention is derivatives of formula (1) in which:

R₁ and R₂, which are identical or different, represent:
  a hydrogen atom;
  a fluorine atom or a chlorine atom;
  a hydroxyl group;
  an alkyl radical chosen from the group comprising the methyl, ethyl, propyl and isopropyl radicals;
  a cyclopropyl radical;
  an alkoxy radical chosen from the group comprising the methoxy, ethoxy, propoxy and isopropoxy radicals;
  a cyclopropoxy radical; or
  when the R₁ and R₂ groups occupy adjacent positions on the aromatic ring, then R₁R₂ represent —CH₂CH₂CH₂—, —OCH₂CH₂—, —OCH₂O— or —CH₂CH₂O—;

R₃ represents;
  an alkyl radical chosen from the group comprising the methyl, ethyl, propyl and isopropyl radicals;
  a hydroxyl group or a methoxy radical;

R₄ represents:
  a hydrogen atom or a methyl radical; and

R₅ and R₆, which are identical or different, represent:
  a hydrogen atom;
  an alkyl radical chosen from the group comprising the methyl, ethyl and isopropyl radicals;
  an alkoxy radical chosen from the group comprising the methoxy, ethoxy, propoxy and isopropoxy radicals;
  an alkylthio radical chosen from the group comprising the methylthio, ethylthio and isopropylthio radicals;
  an alkylamino radical chosen from the group comprising the N-methylamino and N,N-dimethylamino radicals; or R₄R₅ represents a radical chosen from the group comprising —CH₂CH₂—, —CH₂O—, —CH₂CH₂O—, —CH₂CH₂S— and —CH₂CH₂NR₄—, and R₆ is as defined above, their addition salts and the hydrates of these addition salts with inorganic acids or organic acids pharmaceutically acceptable, and their tautomeric forms, the enantiomers and the mixtures of enantiomers, and the stereoisomers, pure or as a racemic or nonracemic mixture.

In a specific embodiment of the invention, derivatives of formula (1) are chosen from the group comprising:

3-[3-(2-methoxyphenylthio)-2-methoxypropyl]amino-3,4-dihydro-2H-1,5-benzoxathiepine;
3-[3-(2-methoxyphenylthio)-2-hydroxypropyl]amino-3,4-dihydro-2H-1,5-benzoxathiepine;
3-[3-(2-hydroxyphenylthio)-2-hydroxypropyl]amino-3,4-dihydro-2H-1,5-benzoxathiepine;
3-[3-(2-methoxyphenylthio)-2-methylpropyl]amino-3,4-dihydro-2H-1,5-benzoxathiepine;
3-[3-(2-methoxyphenylthio)-2-ethylpropyl]amino-3,4-dihydro-2H-1,5-benzoxathiepine;
3-[3-(2-methoxyphenylthio)-2-(n-propyl)propyl]amino-3,4-dihydro-2H-1,5-benzoxathiepine;
3-[3-(2-methoxyphenylthio)-2-(isopropyl)propyl]amino-3,4-dihydro-2H-1,5-benzoxathiepine;
3-[3-(2-methoxyphenylthio)-2-methylpropyl]amino-7-methyl-3,4-dihydro-2H-1,5-benzoxathiepine;
3-[3-(2-methoxyphenylthio)-2-methylpropyl]amino-6-methyl-3,4-dihydro-2H-1,5-benzoxathiepine;
3-[3-(2-hydroxy-3-methylphenylthio)-2-methylpropyl]-amino-3,4-dihydro-2H-1,5-benzoxathiepine;
3-[3-(2-hydroxyphenylthio)-2-methylpropyl]amino-3,4-dihydro-2H-1,5-benzoxathiepine;
3-[3-(2-hydroxy-3-ethylphenylthio)-2-methylpropyl]-amino-3,4-dihydro-2H-1,5-benzoxathiepine;
3-[3-(2,3-dihydrobenzofuran-7-thio)-2-methylpropyl]-amino-3,4-dihydro-2H-1,5-benzoxathiepine;
3-[3-(2-hydroxy-3-methylphenylthio)-2-ethylpropyl]-amino-3,4-dihydro-2H-1,5-benzoxathiepine;
3-[3-(2-hydroxy-3-methylphenylthio)-2-(isopropyl)-propyl]amino-3,4-dihydro-2H-1,5-benzoxathiepine;
3-[3-(2-hydroxy-3-methylphenylthio)-2-methylpropyl]-amino-6-methyl-3,4-dihydro-2H-1,5-benzoxathiepine;
3-[3-(2-hydroxy-3-methoxyphenylthio)-2-methylpropyl]-amino-3,4-dihydro-2H-1,5-benzoxathiepine;
3-[3-(2,3-dimethoxyphenylthio)-2-methylpropyl]amino-3,4-dihydro-2H-1,5-benzoxathiepine;
3-[3-(2-hydroxy-3-(isopropyl)phenylthio)-2-methyl-propyl]amino-3,4-dihydro-2H-1,5-benzoxathiepine;
3-[3-(2-hydroxy-6-methylphenylthio)-2-methylpropyl]-amino-3,4-dihydro-2H-1,5-benzoxathiepine, their addition salts and the hydrates of these addition salts with inorganic acids or organic acids pharmaceutically acceptable, and their tautomeric forms, the enantiomers and the mixtures of enantiomers, and the stereoisomers, pure or as a racemic or nonracemic mixture.

The compounds of general formula (1) can exist in several tautomeric forms. Such tautomeric forms, although not explicitly mentioned in the present application in order to simplify the graphical representation of the expanded formulae, are nevertheless included in the field of application of the invention.

The compounds of the invention comprise two asymmetric carbon atoms in their structure. For this reason, they exist in the form of enantiomers and of diastereoisomers. The invention relates both to each pure stereoisomer, that is to say associated with less than 5% of another stereoisomer or of a mixture of other stereoisomers, and to the mixture of one or more stereoisomers in all proportions. The compounds of the invention can therefore participate as pure stereoisomers or racemic or nonracemic mixtures of stereoisomers. However, among the four existing stereoisomers of a compound of formula (1), the enantiomer in which the C(3) asymmetric carbon atom of the 3,4-dihydro-2H-1,5-benzoxathiepine fragment has the (R) absolute configuration and in which the asymmetric carbon atom which carries the R₃ group has the (S) absolute configuration is, in all cases, preferred.

The labels R and S used to specify the absolute configuration of the stereogenic carbon atoms present in the molecules of formula (1) are defined as in the Cahn-Ingold-Prelog priority rule (E. L. Eliel and S. H. Wilen, Stereochemistry of Organic Compounds, 1994, John Wiley & Sons Inc., chap. 5, 104–12).

In another specific embodiment of the invention, the derivatives of general formula (1) have the (R) absolute configuration at the C(3) asymmetric carbon atom of the 3,4-dihydro-2H-1,5-benzoxathiepine fragment and the (S) absolute configuration at the asymmetric carbon atom which carries the $R_3$ group.

In another particularly advantageous embodiment of the invention, the derivatives of general formula (1) are chosen from the group comprising the following stereoisomers:

3-(R)-[3-(2-methoxyphenylthio)-2-(S)-methoxypropyl]-amino-3,4-dihydro-2H-1,5-benzoxathiepine;
3-(R)-[3-(2-methoxyphenylthio)-2-(S)-hydroxypropyl]-amino-3,4-dihydro-2H-1,5-benzoxathiepine;
3-(R)-[3-(2-hydroxyphenylthio)-2-(S)-hydroxypropyl]-amino-3,4-dihydro-2H-1,5-benzoxathiepine;
3-(R)-[3-(2-methoxyphenylthio)-2-(S)-methylpropyl]-amino-3,4-dihydro-2H-1,5-benzoxathiepine;
3-(R)-[3-(2-methoxyphenylthio)-2-(S)-ethylpropyl]amino-3,4-dihydro-2H-1,5-benzoxathiepine;
3-(R)-[3-(2-methoxyphenylthio)-2-(S)-(n-propyl)propyl]-amino-3,4-dihydro-2H-1,5-benzoxathiepine;
3-(R)-[3-(2-methoxyphenylthio)-2-(S)-(isopropyl)-propyl]amino-3,4-dihydro-2H-1,5-benzoxathiepine;
3-(R)-[3-(2-methoxyphenylthio)-2-(S)-methylpropyl]-amino-7-methyl-3,4-dihydro-2H-1,5-benzoxathiepine;
3-(R)-[3-(2-methoxyphenylthio)-2-(S)-methylpropyl]-amino-6-methyl-3,4-dihydro-2H-1,5-benzoxathiepine;
3-(R)-[3-(2-hydroxy-3-methylphenylthio)-2-(S)-methylpropyl]amino-3,4-dihydro-2H-1,5-benzoxathiepine;
3-(R)-[3-(2-hydroxyphenylthio)-2-(S)-methylpropyl]-amino-3,4-dihydro-2H-1,5-benzoxathiepine;
3-(R)-[3-(2-hydroxy-3-ethylphenylthio)-2-(S)-methylpropyl]amino-3,4-dihydro-2H-1,5-benzoxathiepine;
3-(R)-[3-(2,3-dihydrobenzofuran-7-thio)-2-(S)-methylpropyl]amino-3,4-dihydro-2H-1,5-benzoxathiepine;
3-(R)-[3-(2-hydroxy-3-methylphenylthio)-2-(S)-ethylpropyl]amino-3,4-dihydro-2H-1,5-benzoxathiepine;
3-(R)-[3-(2-hydroxy-3-methylphenylthio)-2-(S)-(isopropyl)propyl]amino-3,4-dihydro-2H-1,5-benzoxathiepine;
3-(R)-[3-(2-hydroxy-3-methylphenylthio)-2-(S)-methylpropyl]amino-6-methyl-3,4-dihydro-2H-1,5-benzoxathiepine;
3-(R)-[3-(2-hydroxy-3-methoxyphenylthio)-2-(S)-methylpropyl]amino-3,4-dihydro-2H-1,5-benzoxathiepine;
3-(R)-[3-(2,3-dimethoxyphenylthio)-2-(S)-methylpropyl]-amino-3,4-dihydro-2H-1,5-benzoxathiepine;
3-(R)-[3-(2-hydroxy-3-isopropylphenylthio)-2-(S)-methylpropyl]amino-3,4-dihydro-2H-1,5-benzoxathiepine;
3-(R)-[3-(2-hydroxy-6-methylphenylthio)-2-(S)-methylpropyl]amino-3,4-dihydro-2H-1,5-benzoxathiepine, their addition salts and the hydrates of these addition salts with inorganic acids or organic acids pharmaceutically acceptable, and their tautomeric forms, the enantiomers and the mixtures of enantiomers, and the stereoisomers, pure or as a racemic or nonracemic mixture.

The invention also relates to the addition salts and optionally the hydrates of the addition salts of the compounds of general formula (1) with inorganic acids or organic acids pharmaceutically acceptable.

The invention also applies to the process for the preparation of the derivatives of general formula (1).

The chemical process used for the preparation of the compounds of general formula (1) depends on the nature of the $R_3$ and $R_4$ substituents.

The compounds of formula (1) can be obtained by one of the processes (a), (b) or (c) described in the following scheme A [lacuna] is illustrated in appendix 1.

Scheme A

According to process (a), when the $R_3$ radical is other than a hydroxyl group and $R_4$ represents a methyl group: the compound of formula (1) is prepared by reductive amination of the aldehyde of formula (II) by means of a primary amine of formula (I) or of a salt of the primary amine of formula (I). The aldehyde of formula (II) can be isolated before being charged to the reductive amination reaction or can be charged to the reductive amination reaction without being isolated beforehand. The reducing agent used in the reductive amination reaction in question can be a simple or complex borohydride, such as, for example, sodium borohydride, potassium borohydride, sodium cyanoborohydride or sodium triacetoxyborohydride.

According to process (b), when $R_3$ is a hydroxyl group: the compound of formula (1) is prepared by regioselective opening of the epoxide of formula (III) by means of the appropriate arylthiophenol of formula (IV) (Synth. Commun., 1996, 26(23), 4459). The epoxide of formula (III) is itself obtained from a precursor of the 3-[(1-chloro-2-hydroxypropyl)amino]-3,4-dihydro-2H-1,5-benzoxathiepine type not mentioned in scheme A as it is not isolated. This is because the inventors have discovered that it is experimentally more advantageous not to isolate the intermediate in question but to carry out the following intramolecular cyclization stage in situ and to isolate pure only the epoxide of formula (III). Said epoxide (III) results from the reaction between the primary amine of formula (I) and a commercially available epichlorohydrin according to conventional techniques of organic chemistry (J. Org. Chem., 1990, 55(9), 2920; WO 00/48987). Under the experimental conditions used by the inventors, the nucleophilic attack of the amine of formula (I) on the epichlorohydrin is both chemo- and regioselective.

According to process (c), when $R_3$ is other than a hydroxyl group and $R_4$ is a hydrogen atom: the intermediate compound of formula (VI) is prepared from the amine of formula (I) and from the aldehyde of formula (V) according to a process identical to that described in process (a). A stage of deprotection of the phenol functional group of the compound (VI) subsequently makes it possible to result in the expected compound of formula (I) (Eur. J. Org. Chem., 2000, 18, 3223).

The compounds of formula (I) can be purified by one or more methods chosen from liquid-phase chromatography techniques. They can subsequently, if desired, be salified by means of a pharmacologically acceptable organic or inorganic acid.

The preparation of the primary amines of formula (I) is described in the following scheme B which is illustrated in appendix 2.

Scheme B

The intermediate of the N-Boc-(2-hydroxyphenyl)cysteine type (VIII) is prepared in a similar way to that of the N-Boc-(4-hydroxyphenyl)-L-cysteine disclosed in international application WO 00/20441. The carboxylic acid functional group of the compound of formula (VIII) is subsequently converted to a primary alcohol functional group. This reaction can advantageously carried out by reduction of an intermediate mixed anhydride, formed in situ, using a simple or complex borohydride according to a one-pot technique well known to the organic chemist. The primary alcohol of formula (IX) is subsequently cyclized, for example by means of an intramolecular Mitsunobu reaction, to give the corresponding cyclic compound (X). The primary amine of formula (I) is obtained by cleavage of the tert-butoxycarbonyl group using a protic acid, such as, for example, trifluoroacetic acid (T. W. Greene and P. G. M. Wuts, Protective Groups in Organic Synthesis, 1999, John Wiley & Sons Inc., 3rd ed., chap. 7, 518–25). The primary amine of formula (I) can, if desired, be salified and stored in the hydrochloride or hydro-bromide form, which is crystalline, nonhygroscopic and stable under standard temperature and light conditions.

The chemical process used for the preparation of the aldehydes of general formulae (II) and (V) depends on the nature of the $R_3$ and $R_4$ substituents.

The aldehydes of formulae (IIa) and (Va), specific cases of the compounds of formulae (II) and (V) in which $R_3$ is a methoxy group, can be prepared according to the method described in the following scheme C which is illustrated in appendix 3.

Scheme C

The primary alcohol functional group of the inter-mediate of the 3-arylthio-1,2-propanediol type (XI), prepared in a similar way to that disclosed in patent FR 1 064 619, is protected in the trityl ether form according to a method analogous to that described by Kim (J. Org. Chem., 1992, 57 (5), 1605). The secondary alcohol functional group of the compound of formula (XII), activated in the form of an alkali metal alkoxide, is then methylated using a methyl halide or methyl sulfate to give the corresponding compound of formula (XIII). The primary alcohol functional group of the compound of formula (XIII) is subsequently released by hydrolysis of the triphenylmethyl group in protic acidic medium (T. W. Greene and P. G. M. Wuts, Protective Groups in Organic Synthesis, 1999, John Wiley & Sons Inc., 3rd ed., chap. 2, 102–4).

According to route (a), when $R_4$ is a methyl radical, the aldehyde of formula (IIa) is obtained by oxidation of the primary alcohol of formula (XIV). The reaction in question can be carried out using an activated dimethyl sulfoxide derivative, such as, for example, dimethyl sulfoxide activated by the sulfur trioxide-pyridine complex, dimethyl sulfoxide activated by oxalyl chloride or dimethyl sulfoxide activated by an oxidizing agent of the hypervalent iodine type, such as, for example, the Dess-Martin reagent, according to conventional techniques well known to the organic chemist.

With regard to the intermediate of formula (XIII), when the R radical represents a methoxymethyl (MOM) group, the detritylation in acidic medium of the primary alcohol functional group is accompanied by the hydrolysis of the methoxymethyl (MOM) group carried by the phenol functional group. The compound obtained is therefore, in this case, the dihydroxylated derivative (XIV, $R_4$=H). The phenol functional group of said intermediate (XIV, $R_4$=H) must be protected before carrying out the oxidation of the primary alcohol functional group according to route (b). This is carried out by chemoselective alkylation of the phenol functional group using chloromethyl methyl ether according to an experimental procedure identical to that described in J. Org. Chem., 1998, 63(10), 3260. The oxidation of the primary alcohol (XV) to the aldehyde of formula (Va) is subsequently carried out in a similar way to that used for the oxidation of the alcohol (XIV, $R_4$=CH$_3$) to the aldehyde (IIa), cf. route (a).

The preparation of the aldehydes of formulae (II) and (V) in which the $R_3$ radical represents an alkyl group, in particular that of the aldehydes of formulae (IIb–g) and (Vb–j), is described in the following scheme D which is illustrated in appendix 4.

Scheme D

The aldehydes of formulae (IIb–g) and (Vb–j) derive from a common precursor of the 2-alkyl-3-(arylthio)propan-1-ol type of formula (XX). This intermediate is obtained by reaction of the appropriate arylthiol of formula (IV) or of an alkali metal salt derived from said arylthiol with commercially available 3-bromo-2-methylpropan-1-ol or with 2-alkyl-3-hydroxypropyl p-toluenesulfonate of formula (XIX), the method of preparation of which is described hereinafter.

The compound of formula (XVI), prepared according to the method described by Fukumoto in J. Org. Chem., 1996, 61(2), 677, is reduced to the alcohol (XVII) using lithium borohydride in tetrahydrofuran (THF) according to an experimental procedure similar to that described in J. Org. Chem., 1994, 59(18), 5317 or in Synth. Commun., 1990, 20(2), 307. The primary alcohol functional group of the compound of formula (XVII) is first converted to the p-toluenesulfonic acid ester (tosylate) of formula (XVIII). The compound of formula (XVIII) can then be debenzylated by hydrogenolysis in the presence of a palladium catalyst to give the expected compound (XIX) according to a method similar to that described in J. Am. Chem. Soc., 1999, 121(43), 9967.

According to route (a), the intermediate of formula (XX), in which $R_4$ is a methyl radical or forms, with the adjacent $R_5$ group, a heterocycle, can be oxidized directly to the aldehyde of formula (II) according to a method similar to that described above for the oxidation of the alcohol (XIV, $R_4$=CH$_3$) to the aldehyde (IIa) (cf. scheme C, route (a)). However, in the case where the enantiomeric purity of the asymmetric carbon atom which carries the $R_3$ radical in the precursor of formula (XX) has to be retained in the final compound of formula (1), the following limitations apply:

the reaction for the oxidation of the alcohol (XX) to the aldehyde (II) is carried out according to the Swern method modified according to Evans (J. Am. Chem. Soc., 1993, 115(24), 11446);

the aldehyde of formula (II) is not isolated but is used in situ in the following reductive amination stage (cf. scheme A, process (a)).

According to route (b), the phenol functional group of the compound of formula (XX) is converted either to the methoxymethyl ether (XXIa, R=MOM) or to the methyl ether (XXIb, R=CH$_3$). The oxidation of the alcohol (XXI) to the aldehyde (II) or (V) is subsequently carried out according to a method identical to that used for the preparation of the aldehyde (II) from the alcohol (XX) (cf. scheme D, route (a)). The limitations which apply to the oxidation of the alcohol (XX) to the aldehyde (II) and to the use of said aldehyde in the following reductive amination reaction also apply to the oxidation of the alcohol (XXI) to the aldehyde (II) or (V) and to their use in the reductive amination reaction.

The compounds of the arylthiol type of formula (IV), of use as intermediates in the preparation of the aldehydes of formulae (II) and (V) and in the preparation of certain primary amines of formula (I), are either commercially available or are described in the literature (i.e. Heterocycles, 1999, 50(2), 681; J. Heterocyclic Chem., 1998, 35(3), 699; JP 08143533; JP 06293640; Synth. Commun., 1994, 24(1), 35; J. Org. Chem., 1994, 59(16), 4618; Drug Metab. Dispos., 1992, 20(5), 688; J. Org. Chem., 1990, 55(9), 2736; J. Med. Chem., 1990, 33(5), 1491; J. Med. Chem., 1989, 32(10), 2399; EP 200 212; J. Org. Chem., 1979, 44(26), 4971; J. Pharm. Sci., 1976, 65(10), 1554; DE 2411826; Gazz. Chim. Ital., 1969, 99(11), 1095; Gazz. Chim. Ital., 1969, 99(4), 397; J. Am. Chem. Soc., 1955, 77, 568) or are prepared according to the procedures described in the examples illustrating the present invention.

Another subject matter of the invention is the amines of formula (I)

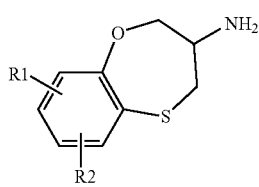

in which $R_1$ and $R_2$, which are identical or different, represent:
  a hydrogen atom;
  a fluorine atom or a chlorine atom;
  a hydroxyl group;
  a linear or branched alkyl radical including from 1 to 3 carbon atoms;
  a cyclopropyl radical;
  a linear or branched alkoxy radical including from 1 to 3 carbon atoms;
  a cyclopropoxy radical; or
  when the $R_1$ and $R_2$ groups occupy adjacent positions on the aromatic ring, they form, with the carbon atoms which carry them, a nonaromatic five-membered oxygen-comprising heterocycle or carbonaceous ring;

of use as intermediates in the synthesis of the compounds of formula (1).

In a particularly advantageous embodiment of the invention, the amines of formula (1) are those in which the C(3) asymmetric carbon atom has the (R) absolute configuration.

Another subject matter of the invention is the process for the preparation of the compounds of formula (I), characterized in that the N-Boc-(2-hydroxyphenyl)-cysteine of formula (VIII)

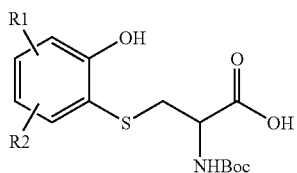

is converted to the primary alcohol of formula (IX)

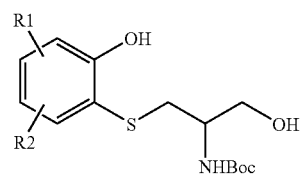

by reduction of an intermediate mixed anhydride, formed in situ, using a simple or complex borohydride according to a one-pot technique, and then said compound (IX) is cyclized to produce the corresponding cyclic compound (X)

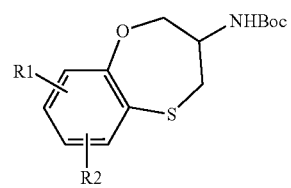

which is treated with a protic acid to produce the amine of formula (I), which is salified, if desired.

Another subject matter of the invention is the aldehydes of formula (II)

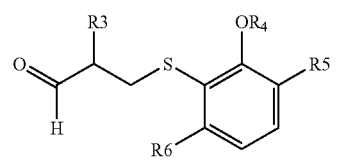

in which $R_3$ represents
  a linear or branched alkyl radical including from 1 to 3 carbon atoms or a methoxy radial, $R_4$ represents:
  a hydrogen atom or a methyl radical, and $R_5$ and $R_6$, which are identical or different, represent:
  a hydrogen atom;
  a linear or branched alkyl radical including from 1 to 3 carbon atoms;
  a linear or branched alkoxy radical including from 1 to 3 carbon atoms;
  a linear or branched alkylthio radical including from 1 to 3 carbon atoms;
  an alkylamino radical, provided that, when $R_4$ represents a methyl radical, then $R_5$ represents a hydrogen atom, an alkoxy radical including from 1 to 3 carbon atoms, a linear or branched alkylthio radical including from 1 to 3 carbon atoms or an alkylamino radical, or the OR₄ and R₅ groups form, with the carbons which carry them, a nonaromatic five- or six-membered heterocycle comprising at least one oxygen atom, and R₆ is as defined above, of use as intermediates in the synthesis of the compounds of formula (1).

In a specific embodiment of the invention, the aldehydes of formula (II) are those in which the asymmetric carbon atom carrying the R₃ group has the (S) absolute configuration.

Another subject matter of the invention is the aldehydes of formula (V)

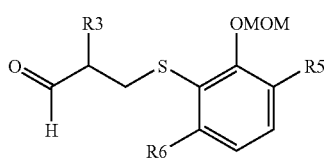
(V)

in which
R₃ represents
  a linear or branched alkyl radical including from 1 to 3 carbon atoms or a methoxy radical, and
R₅ and R₆, which are identical or different, represent:
  a hydrogen atom;
  a linear or branched alkyl radical including from 1 to 3 carbon atoms;
  a linear or branched alkoxy radical including from 1 to 3 carbon atoms;
  a linear or branched alkylthio radical including from 1 to 3 carbon atoms;
  an alkylamino radical, of use as intermediates in the synthesis of the compounds of formula (1).

In an advantageous embodiment of the invention, the aldehydes of formula (V) are those in which the asymmetric carbon atom carrying the R₃ group has the (S) absolute configuration.

Another subject matter of the invention is the process for the preparation of the compounds of formula (IIa) in which R₃ represents a methoxy group and of the compounds of formula (Va) in which R₃ represents a methoxy group, characterized in that the primary alcohol functional group of the intermediate of the 3-arylthio-1,2-propanediol type (XI)

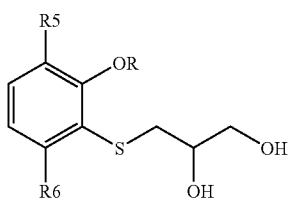
(XI)

in which R represents a methyl or methoxymethyl (MOM) radical and R₅ and R₆ are as defined in claim 1, is protected in the form of the trityl ether of formula (XII),

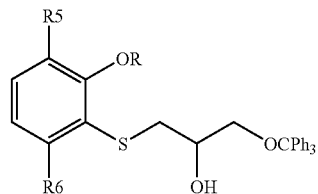
(XII)

activated in the form of an alkali metal alkoxide and then methylated using a methyl halide or sulfate to give the compound of formula (XIII)

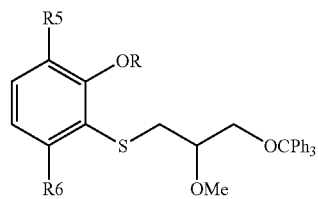
(XIII)

in which R is as defined above, and the primary alcohol functional group is released by hydrolysis of the triphenylmethyl group in a protic acidic medium, and the following compounds are obtained, when R is a methyl radical, a compound of formula (XIVa1)

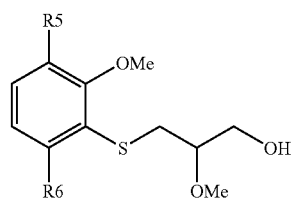
(XIVa₁)

the primary alcohol of which is oxidized and a compound of formula (IIa) is obtained

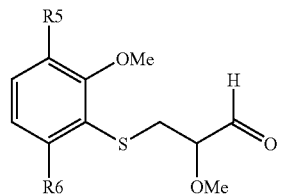
(II-a)

when R is a methoxymethyl radical, a compound of formula (XIVa2) is obtained

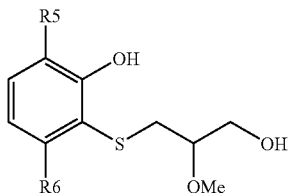

(XIVa₂)

the phenol functional group of which is protected by chemoselective alkylation using chloromethyl methyl ether and a compound of formula (XV) is obtained

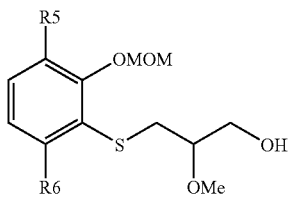

(XV)

the primary alcohol of which is oxidized and a compound of formula (Va) is obtained

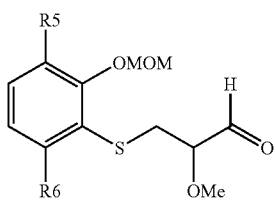

(Va)

Another subject matter of the invention is the process for the preparation of the compounds of formulae (II) and (V), in particular of the compounds of formula (IIb–g) and of the compounds of formula (Vb–j), in which $R_3$ represents an alkyl radical, characterized in that either a compound of formula (XVI)

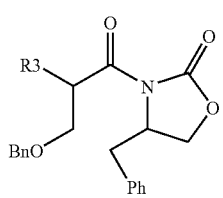

(XVI)

in which $R_3$ represents a linear or branched alkyl radical including from 1 to 3 carbon atoms, is reduced and an alcohol of formula (XVII)

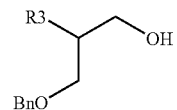

(XVII)

is obtained, which is converted to a p-toluenesulfonic acid ester (tosylate) of formula (XVIII)

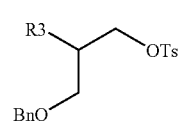

(XVIII)

which is subjected to hydrogenolysis in the presence of a palladium catalyst to give the compound (XIX)

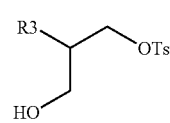

(XIX)

which is reacted with a compound of formula (IV), optionally in the form of an alkali metal salt,

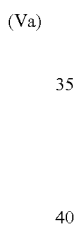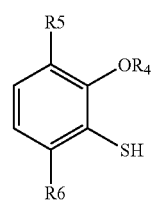

(IV)

in which
$R_4$ represents:
  a hydrogen atom or a methyl radical, and
$R_5$ and $R_6$, which are identical or different, represent:
  a hydrogen atom;
  a linear or branched alkyl radical including from 1 to 3 carbon atoms;
  a linear or branched alkoxy radical including from 1 to 3 carbon atoms;
  a linear or branched alkylthio radical including from 1 to 3 carbon atoms;
  an alkylamino radical,
  provided that, when $R_4$ represents a methyl radical, then $R_5$ represents a hydrogen atom, an alkoxy radical including from 1 to 3 carbon atoms, a linear or branched alkylthio radical including from 1 to 3 carbon atoms or an alkylamino radical, or
  the $OR_4$ and $R_5$ groups form, with the carbons which carry them, a nonaromatic five- or six-membered heterocycle comprising at least one oxygen atom, and $R_6$ is as defined above,
or 3-bromo-2-methylpropan-1-ol is reacted with a compound of formula (IV)
and a compound of formula (XX)

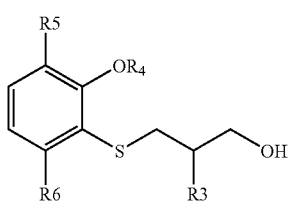

(XX)

is obtained, then, when $R_4$ is an alkyl radical or forms, with the adjacent $R_5$ group, a heterocycle, the compound of formula (XX) is oxidized directly to the aldehyde of formula (IIb–g)

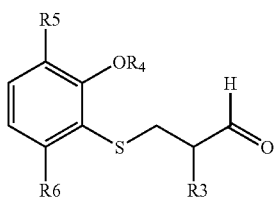

(IIb-g)

or, when $R_4$ is a hydrogen atom, then the phenol functional group of the compound of formula (XX) is converted to the compound of formula (XXI)

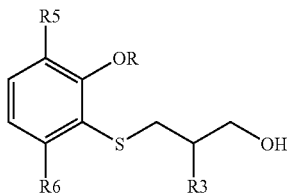

(XXI, R = CH₃ or MOM)

in which R represents a methoxymethyl radical (XXIa, R=MOM) or a methyl radical (XXIb, R=CH₃), then the alcohol (XXIa) is oxidized to the aldehyde (II)

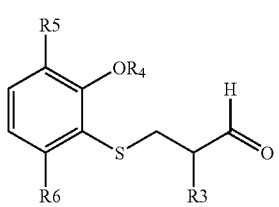

(II)

and the alcohol (XXIb) to the aldehyde (V)

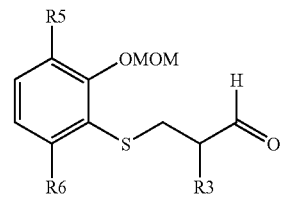

(V)

Another subject matter of the invention is the pharmaceutical compositions comprising, as active principle, at least one of the derivatives of general formula (1) or one of its addition salts or hydrates of its addition salts in combination with one or more inert pharmaceutical carriers or other pharmaceutically acceptable vehicles and optionally with another medicament.

The pharmaceutical compositions according to the invention can, by way of example, be compositions which can be administered orally, nasally, sublingually, rectally or parenterally. Mention may be made, by way of example of compositions which can be administered orally, of tablets, hard gelatin capsules, granules, powders and solutions or suspensions to be taken orally.

The appropriate formulations for the chosen administration form are known and are described, for example, in: Remington, The Science and Practice of Pharmacy, 19th edition, 1995, Mack Publishing Company.

The effective dose of a compound of the invention varies according to numerous parameters, such as, for example, the chosen administration route, the weight, the age, the sex, the nature of the pathology and the sensitivity of the individual to be treated. Consequently, the optimum dosage should be determined, according to the parameters regarded as relevant, by a specialist in the matter. Although the effective doses of a compound of the invention can vary greatly, the daily doses might range between 0.01 mg and 100 mg per kg of body weight of the individual to be treated. A daily dose of a compound of the invention of between 0.10 mg and 50 mg per kg of body weight of the individual to be treated being preferred, however.

The pharmaceutical compositions according to the invention are of use in the treatment of stable angina, unstable angina, cardiac insufficiency, long QT syndrome of congenital origin, myocardial infarction and cardiac rhythm disorders.

They can also be of use in the treatment of cerebral ischemia, transitory ischemic attack, neuropathies of a traumatic or ischemic nature, and epilepsy, and in that of the treatments of pain of neuropathic origin and of neurodegenerative diseases.

EXAMPLES

The following examples illustrate the invention but do not limit it in any way:

examples 1 to 4 illustrate the synthesis of the intermediates I according to scheme B, examples 5 and 6 illustrate the synthesis of the intermediates IIa according to scheme C, examples 7 to 15 illustrate the synthesis of the intermediates IIb–g according to scheme D, examples 16 and 17 illustrate the synthesis of the intermediates III of process b illustrated in scheme A, examples 18 to 25 illustrate the synthesis of the intermediates V according to route c illustrated in scheme D, examples 26 to 34 illustrate the synthesis of the intermediates VIa–j according to process c illustrated in scheme A, and reference examples 1 to 26 illustrate the synthesis of the compounds of formula (1) according to scheme A.

In the examples and the reference examples hereinafter:
(i) the progress of the reactions is monitored by thin layer chromatography (TLC) and, consequently, the reaction times are only mentioned by way of indication;
(ii) different crystalline forms can give different melting points; the melting points mentioned in the present application are those of the products prepared according to the method described and are not corrected;
(iii) the structures of the products obtained according to the invention are confirmed by the nuclear magnetic resonance (NMR) spectra, the infrared (IR) spectra and percentage analysis, the purity of the final products is confirmed by TLC, and the enantiomeric purity of the reaction intermediates and of the final products is determined by chiral phase HPLC;
(iv) the NMR spectra are recorded in the solvent indicated. The chemical shifts (δ) are expressed in parts per million (ppm) with respect to tetramethylsilane. The multiplicity of the signals is indicated by: s, singlet; d, doublet; t, triplet; q, quartet; m, multiplet; b, broad;
(v) the different symbols for the units have their usual meanings: μg (microgram); mg (milligram); g (gram); ml (milliliter); mV (millivolt); °C. (degrees Celsius); mmol (millimole); nmol (nanomole); cm (centimeter); nm (nanometer); min (minute); ms (millisecond); Hz (hertz); [α](specific rotation, measured at 589 nm, at 25° C. and at the concentration c; in the present invention, the measure $deg.cm^2.g^{-1}$ is always to be understood); the pressures are given in millibar (mb);
(vi) the abbreviations have the following meanings: M.p. (melting point); B.p. (boiling point); AUC (area under the curve);
(vii) the term "ambient temperature" is understood to mean a temperature between 20° C. and 25° C.

Example 1

3-(R)-Amino-3,4-dihydro-2H-1,5-benzoxathiepine (Ia-1)

Stage 1: 2-(R)-tert-Butoxycarbonylamino-3-(2-hydroxyphenylthio)propan-1-ol (IXa-1)

74.45 g (0.237 mol) of N-Boc-(2-hydroxyphenyl)-L-cysteine (VIII) and 300 ml of distilled tetrahydrofuran are introduced into a round-bottomed flask kept under an inert atmosphere. The mixture is cooled to −10° C. and then 26 ml (0.236 mol) of N-methylmorpholine are added dropwise. After stirring for 15 minutes at −10° C., 22.7 ml (0.237 mol) of ethyl chloroformate are introduced dropwise. The mixture is stirred at −10° C. for 30 minutes and then the precipitate formed is filtered off under cold conditions. The filtrate is recovered directly in a round-bottomed flask and cooled to −10° C. 13.45 g (0.35 mol) of sodium borohydride in solution in 50 ml of water are then introduced in such a way that the temperature of the mixture does not exceed −10° C. At the end of the addition, the mixture is reheated to ambient temperature and stirred for 12 hours. The mixture is concentrated under reduced pressure, acidified using 250 ml of an aqueous potassium hydrogensulfate solution (2N) and extracted with dichloromethane. The combined organic phases are washed with brine, dried over sodium sulfate, filtered and concentrated under reduced pressure. 61.41 g (0.205 mol) of the title compound (IXa-1) are obtained in the form of a yellow oil, which is used without additional purification in the following stage.

Crude yield: 86% [α]=−44.2 (c=0.371, methanol) $^1$H NMR (d$_6$-DMSO) δ: 1.38 (s, 9H), 2.80 (dd, 1H), 3.03 (dd, 1H), 3.35 (bs, 1H), 3.49 (m, 2H), 4.78 (m, 1H), 6.74 (m, 3H), 7.02 (m, 1H), 7.23 (m, 1H), 9.72 (bs, 1H).

Stage 2: 3-(R)-tert-Butoxycarbonylamino-3,4-dihydro-2H-1,5-benzoxathiepine (Xa-1)

[lacuna] (0.205 mol) of 2-tert-butoxycarbonyl-amino-3-(2-hydroxyphenylthio)propan-1-ol (IXa-1), 300 ml of distilled tetrahydrofuran and 53.80 g (0.205 mol) of triphenylphosphine are introduced into a round-bottomed flask kept under an inert atmosphere. The mixture is cooled to 0° C. and then 31.9 ml (0.205 mol) of diethyl azodicarboxylate are added dropwise. The mixture is stirred at ambient temperature for 24 hours. The tetrahydrofuran is evaporated under reduced pressure and then the residue is taken up in ethyl ether. The precipitate formed is removed by filtration and the filtrate is concentrated under reduced pressure. The residue is purified by flash chromatography on silica gel (eluent: dichloromethane/cyclohexane=80:20). 48 g (0.170 mol) of the title compound (Xa-1) are recovered in the form of a pinkish oil.

Yield: 83% [α]=+15.2 (c=0.493, methanol) $^1$H NMR (CDCl$_3$) δ: 1.47 (s, 9H), 2.93 (dd, 1H), 3.07 (dd, 1H), 3.95 (d, 1H), 4.27 (bs, 1H), 4.34 (d, 1H), 5.64 (bd, 1H), 7.00 (m, 2H), 7.18 (td, 1H), 7.41 (d, 1H) HPLC (Chiracel OD, hexane/isopropanol (92:8), 0.5 ml/min): compound (Xa-1), retention time=12.71 min; compound (Xa-2), retention time=14.05 min; ratio of the AUCs (Xa-1)/(Xa-2)=98:2.

Stage 3: 3-(R)-Amino-3,4-dihydro-2H-1,5-benzoxathiepine (Ia-1)

48 g (0.170 mol) of 3-(R)-tert-butoxycarbonyl-amino-3,4-dihydro-2H-1,5-benzoxathiepine (Xa-1) and 120 ml of hydrochloric acid (2N) in ethanol are introduced into a round-bottomed flask equipped with a reflux condenser. The mixture is brought to 80° C. for 2 to 3 hours. The mixture is cooled, concentrated under reduced pressure and then diluted with ethyl ether. The precipitate formed is filtered off, washed with ethyl ether and pulled dry. 19 g (0.087 mol) of the hydrochloride of the title compound (Ia-1) are thus recovered in the form of a white solid.

Yield: 50% M.p.: 235° C. [α]=+48.9 (c=0.350, methanol) Analysis $C_9H_{12}ClNOS$:

| | | | |
|---|---|---|---|
| Calc. %: | C 49.65 | H 5.56 | N 6.43 |
| Found: | C 49.59 | H 5.63 | N 6.32 |

$^1$H NMR (d$_6$-DMSO) δ: 3.12 (dd, 1H), 3.21 (dd, 1H), 3.81 (m, 1H), 4.21 (dd, 1H), 4.31 (dd, 1H), 7.09 (m, 2H), 7.28 (td, 1H), 7.45 (dd, 1H), 8.64 (bs, exchangeable) HPLC (Chiralpack AD, hexane/ethanol/diethylamine (95:4.95:0.05), 1 ml/min): compound (Ia-1), retention time=25.26 min; compound (Ia-2), retention time=23.48 min; ratio of the AUCs (Ia-1)/(Ia-2)=98:2.

Example 2

3-(S)-Amino-3,4-dihydro-2H-1,5-benzoxathiepine (Ia-2)

The hydrochloride of the title compound (Ia-2) is prepared according to a reaction sequence identical to that employed for the synthesis of 3-(R)-amino-3,4-dihydro-2H-1,5-benzoxathiepine (Ia-1) but using, as starting material, N-Boc-(2-hydroxyphenyl)-D-cysteine instead of N-Boc-(2-hydroxyphenyl)-L-cysteine.

M.p. 210° C. (sublimation) [α]=−44.8 (c=0.402, methanol) Analysis $C_9H_{12}ClNOS$:

| | | | |
|---|---|---|---|
| Calc. %: | C 49.65 | H 5.56 | N 6.43 |
| Found: | C 49.68 | H 5.57 | N 6.50 |

$^1$H NMR (d$_6$-DMSO) δ: 3.12 (dd, 1H), 3.21 (dd, 1H), 3.80 (bs, 1H), 4.20 (d, 1H), 4.31 (dd, 1H), 7.09 (m, 2H), 7.28 (m, 1H), 7.45 (d, 1H), 8.63 (bs, exchangeable). HPLC (Chiralpack AD, hexane/ethanol/diethylamine (95:4.95:0.05), 1 ml/min): compound (Ia-2), retention time=23.07 min; compound (Ia-1), retention time=24.99 min; ratio of the AUCs (Ia-2)/(Ia-1)=96:4.

Example 3

3-(R)-Amino-7-methyl-3,4-dihydro-2H-1,5-benzoxathiepine (Ib)

The title compound (Ib) is prepared according to a reaction sequence identical to that employed for the synthesis of 3-(R)-amino-3,4-dihydro-2H-1,5-benzoxathiepine (Ia-1) but using, as starting material, 2-hydroxy-5-methylthiophenol (IVb) instead of 2-hydroxythiophenol. The title compound (Ib) is obtained in the form of a yellow oil.

Yield: 60% [α]=+46 (c=0.106, methanol) $^1$H NMR (CDCl$_3$) δ: 1.65 (bs, exchangeable H), 2.26 (s, 3H), 2.76 (dd, 1H), 3.15 (dd, 1H), 3.42 (m, 1H), 4.05 (m, 2H), 6.92 (m, 2H), 7.19 (d, 1H).

Example 4

3-(R)-Amino-6-methyl-3,4-dihydro-2H-1,5-benzoxathiepine (Ic)

Stage 1: 2-Hydroxy-6-methylthiophenol (IVc)

5.3 g (0.077 mol) of sodium nitrite in solution in 12 ml of water are added dropwise to a round-bottomed flask comprising 14 g of ice, 14 ml of 36% hydrochloric acid and 8.62 g (0.07 mol) of 2-amino-m-cresol. The mixture, kept at 0° C., is subsequently poured slowly into a solution of 15 g (0.093 mol) of potassium ethyl xanthate in 20 ml of water held at 40° C. The heating bath is removed and the mixture is stirred for 3 hours and then extracted with ethyl ether. The combined organic phases are washed with aqueous saline solution, dried over magnesium sulfate, filtered and concentrated under reduced pressure. The residue is purified by fast chromatography on silica gel (eluent: cyclohexane/dichloromethane=65:35). The oil obtained is taken up in 20 ml of ethanol and the mixture is heated to 100° C. 20 ml of an ethanolic potassium hydroxide solution (7N) are then added dropwise. After 4 hours at 100° C., the mixture is cooled, concentrated under reduced pressure, acidified using hydrochloric acid (2N) and then extracted with ethyl ether. The combined organic phases are dried over magnesium sulfate, filtered and concentrated under reduced pressure to give a yellow oil which is not isolated but is used directly in the following stage.

Stage 2: 3-(R)-Amino-6-methyl-3,4-dihydro-2H-1,5-benzoxathiepine (Ic)

The hydrochloride of the title compound (Ic) is prepared according to a reaction sequence similar to that employed for the synthesis of 3-(R)-amino-3,4-dihydro-2H-1,5-benzoxathiepine (Ia-1) but using, as starting material, 2-hydroxy-6-methylthiophenol (IVc) instead of 2-hydroxythiophenol.

M.p.>250° C. [α]=+101.4 (c=0.313, methanol) Analysis $C_{10}H_{14}ClNOS$:

| | | | |
|---|---|---|---|
| Calc. %: | C 51.83 | H 6.09 | N 6.04 |
| Found: | C 51.64 | H 6.12 | N 5.89 |

$^1$H NMR (d$_6$-DMSO) δ: 2.37 (s, 3H), 3.16 (m, 2H), 3.79 (m, 1H), 4.20 (1d, 1H), 4.30 (dd, 1H), 6.94 (d, 1H), 7.03 (d, 1H), 7.14 (m, 1H), 8.59 (bs, 3 exchangeable H).

Example 5

2-(S)-Methoxy-3-(2-methoxyphenylthio)-propionaldehyde (IIa-1)

Stage 1: 1-(3-Triphenylmethyloxy-2-(S)-hydroxy-propylthio)-2-methoxybenzene (XII-1)

19.3 g (0.09 mol) of 1-(3-hydroxy-2-(S)-hydroxy-propylthio)-2-methoxybenzene (XI-1), 150 ml of acetonitrile, 11 ml (0.136 mol) of pyridine and 27.5 g (0.098 mol) of triphenylmethyl chloride are introduced into a round-bottomed flask under an inert atmosphere. The solution is stirred at ambient temperature for 5 hours. The mixture is concentrated under reduced pressure and the residual pyridine is entrained by azeotropic distillation with toluene. The residue is taken up in water and then extracted with dichloromethane. The combined organic phases are dried over sodium sulfate, filtered and evaporated, and the residue is purified by flash chromatography on silica gel (eluent: cyclohexane/dichloromethane=30:70). 34.8 g (0.076 mol) of the title compound (XII-1) are recovered in the form of a yellow oil.

Yield: 85% [α]=−7.1 (c=0.225, methanol) $^1$H NMR (CDCl$_3$) δ: 2.80 (d, 1H), 2.93 (dd, 1H), 3.14 (dd, 1H), 3.23 (d, 2H), 3.77 (m, 1H), 3.87 (s, 3H), 6.88 (m, 2H), 7.25 (m, 10H), 7.34 (dd, 1H), 7.41 (d, 6H).

Stage 2: 1-(3-Triphenylmethyloxy-2-(S)-methoxy-propylthio)-2-methoxybenzene (XIII-1)

34.8 g (0.076 mol) of 1-(3-triphenylmethyloxy-2-(S)-hydroxypropylthio)-2-methoxybenzene (XII-1), in solution in 50 ml of distilled tetrahydrofuran, are introduced dropwise into a round-bottomed flask, kept under an inert atmosphere, comprising a suspension of 3.5 g of sodium hydride (0.087 mol) in 30 ml of distilled tetrahydrofuran. The mixture is stirred at ambient temperature for 3 hours and then 5.1 ml (0.082 mol) of methyl iodide are added. After stirring at ambient temperature for 2 hours, the mixture is concentrated under reduced pressure and then the residue is taken up in dichloromethane. The solution obtained is cooled and then diluted with ice-cold water. The phases are separated and the aqueous phase is extracted with dichloromethane. The combined organic phases are washed with water and with brine, dried over magnesium sulfate, filtered and concentrated under reduced pressure. The residue is purified by flash chromatography on silica gel (eluent: dichloromethane/cyclohexane=70:30) to give 35.8 g (0.076 mol) of the title compound (XIII-1) in the form of an oil.

Yield: 100% $^1$H NMR (CDCl$_3$) δ: 3.01 (dd, 1H), 3.16 (dd, 1H), 3.25 (dd, 2H), 3.36 (s, 3H), 3.43 (m, 1H), 3.85 (s, 3H), 6.86 (m, 2H), 7.41 (m, 10H), 7.35 (m, 1H), 7.43 (d, 6H).

Stage 3: 2-(S)-Methoxy-3-(2-methoxyphenylthio)-propan-1-ol (XIV-1)

35.8 g (0.076 mol) of 1-(3-triphenylmethyloxy-2-(S)-methoxypropylthio)-2-methoxybenzene (XIII-1) and 150 ml of a solution of hydrochloric acid (2.5N) in ethanol are introduced into a round-bottomed flask kept under an inert atmosphere. The mixture is stirred at ambient temperature for 4 hours. The white precipitate formed is removed by filtration and the filtrate is concentrated under reduced pressure. The residue is purified by flash chromatography on silica gel (eluent: dichloromethane/ethyl acetate=90:10). 13.4 g (0.058 mol) of the title compound (XIV-1) are recovered in the form of an orange oil.

Yield: 77% [α]=−15.5 (c=0.0780, methanol) $^1$H NMR (CDCl$_3$) δ: 1.99 (t, 1H), 2.97 (dd, 1H), 3.15 (dd, 1H), 3.42 (s, 3H), 3.44 (m, 1H), 3.65 (m, 1H), 3.83 (m, 1H), 3.90 (s, 3H), 6.87 (d, 1H), 6.93 (t, 1H), 7.23 (td, 1H), 7.35 (dd, 1H).

Stage 4: 2-(S)-Methoxy-3-(2-methoxyphenylthio)-propionaldehyde (IIa-1)

4 g (0.017 mol) of 2-(S)-methoxy-3-(2-methoxyphenylthio)propan-1-ol (XIV-1), 100 ml of dichloromethane and 11.13 g (0.026 mol) of Dess-Martin reagent are introduced into a round-bottomed flask kept under an inert atmosphere. The mixture is stirred at ambient temperature for 3 hours. 190 ml of a saturated aqueous sodium thiosulfate solution are subsequently added, followed by 190 ml of a saturated aqueous sodium hydrogencarbonate solution, and the mixture is extracted with dichloromethane. The combined organic phases are washed with water and with brine, dried over magnesium sulfate, filtered and concentrated under reduced pressure. The residue is purified by flash chromatography on silica gel (eluent: dichloromethane/ethyl acetate=95:5). 1.2 g (0.005 mol) of the title compound (IIa-1) are recovered in the form of a yellow oil.

Yield: 31% $^1$H NMR (CDCl$_3$) δ: 3.13 (dd, 1H), 3.23 (dd, 1H), 3.47 (s, 3H), 3.70 (m, 1H), 3.90 (s, 3H), 6.88 (dd, 1H), 6.92 (td, 1H), 7.26 (td, 1H), 7.38 (dd, 1H), 9.68 (d, 1H).

Example 6

2-(R)-Methoxy-3-(2-methoxyphenylthio)-propionaldehyde (IIa-2)

The title compound (IIa-2) is obtained by carrying out the preparation as in example 5 but by replacing, in stage 1, 1-(3-hydroxy-2-(S)-hydroxypropylthio)-2-methoxybenzene (XI-1) with 1-(3-hydroxy-2-(R)-hydroxypropylthio)-2-methoxybenzene (XI-2).

Yield: 90% $^1$H NMR (CDCl$_3$) δ: 3.12 (dd, 1H), 3.23 (dd, 1H), 3.47 (s, 3H), 3.70 (m, 1H), 3.90 (s, 3H), 6.89 (m, 2H), 7.26 (m, 1H), 7.38 (dd, 1H), 9.67 (d, 1H).

Example 7

2-(S)-Methyl-3-(2-methoxyphenylthio)-propionaldehyde (IIb-1)

Stage 1: 2-(S)-Methyl-3-(2-methoxyphenylthio)-propan-1-ol (XXb-1)

2.2 ml (0.021 mol) of 3-bromo-2-(S)-methyl-1-propanol are introduced into a round-bottomed flask kept under an inert atmosphere. 20 ml of an aqueous sodium hydroxide solution (1N) are added dropwise, followed by 2.3 ml (0.019 mol) of 2-methoxythiophenol. The mixture is brought to 90° C. for 4 hours and is then cooled to ambient temperature. 50 ml of water are then added and the mixture is extracted with dichloromethane. The combined organic phases are washed with brine, dried over sodium sulfate, filtered and concentrated under reduced pressure. The residue is purified by flash chromatography on silica gel (eluent: dichloromethane/methanol=99:1). 4 g (0.019 mol) of the title compound (XXb-1) are recovered in the form of a colorless oil.

Yield: 100% [α]=+22.2 (c=0.982, methanol) $^1$H NMR (d$_6$-DMSO) δ: 0.95 (d, 3H), 1.74 (m, 1H), 2.61 (dd, 1H), 3.01 (dd, 1H), 3.34 (m, 2H), 3.80 (s, 3H), 4.61 (t, 1 exchangeable H), 6.94 (m, 2H), 7.14 (td, 1H), 7.23 (dd, 1H).

Stage 2: 2-(S)-Methyl-3-(2-methoxyphenylthio)-propionaldehyde (IIb-1)

0.61 ml (0.007 mol) of oxalyl chloride and 20 ml of dichloromethane are introduced into a round-bottomed flask kept under an inert atmosphere. The mixture is cooled to −78° C. and then 1 ml (0.014 mol) of dimethyl sulfoxide is introduced. After stirring at −78° C. for 15 minutes, 1.5 g (0.007 mol) of 2-(S)-methyl-3-(2-methoxyphenylthio)propan-1-ol (XXb-1), in solution in 15 ml of dichloromethane, are added dropwise. The mixture is stirred at −78° C. for 1 hour and then 2 ml (0.014 mol) of triethylamine are added. After 15 minutes at −78° C., the mixture is reheated to −10° C. and stirred at this temperature for 45 minutes. The aldehyde is not isolated at this stage but is used in situ in the following reductive amination reaction.

Example 8

2-(R)-Methyl-3-(2-methoxyphenylthio)-propionaldehyde (IIb-2)

The title compound (IIb-2) is obtained by carrying out the preparation as in example 7 but by using, in stage 1, 3-bromo-2-(R)-methyl-1-propanol instead of 3-bromo-2-(S)-methyl-1-propanol. This title compound, like the aldehyde (IIb-1) is not isolated but is used in situ in the following reductive amination reaction.

Example 9

2-(S)-Methyl-3-(2,3-dihydrobenzofuran-7-thio)propionaldehyde (IIc)

Stage 1: 2,3-Dihydrobenzofuran-7-thiol (IVd)

3 ml (0.026 mol) of 2,3-dihydrobenzofuran and 50 ml of ethyl ether are introduced into an inert atmosphere. The mixture is cooled to 0° C. and then 11.5 ml (0.029 mol) of a solution of n-butyllithium (2.5M) in hexane are added dropwise. At the end of the addition, the mixture is brought to reflux for 24 hours and then cooled to 0° C. before adding, portionwise, 0.92 g (0.029 mol) of sublimed sulfur. The mixture is heated at reflux for 2 hours and is then again cooled to 0° C. before adding 6 ml of hydrochloric acid (10N). The phases are separated and the aqueous phase is extracted with ethyl ether. The combined organic phases are washed with an aqueous hydrochloric acid solution (1N) and with water and then extracted using an aqueous sodium hydroxide solution (1N). The combined alkaline phases are washed with ethyl ether, acidified and extracted with ethyl ether. The combined ethereal phases are dried over sodium sulfate, filtered and concentrated under reduced pressure. The residue is purified by flash chromatography on silica gel (eluent: cyclohexane/ether=90:10) to give 0.4 g (0.0026 mol) of the title compound (IVd).

Yield: 10% $^1$H NMR ($d_6$-DMSO) δ: 3.20 (t, 2H), 4.55 (m, 2H), 4.79 (bs, 1 exchangeable H), 6.72 (m, 1H), 7.01 (m, 2H).

Stage 2: 2-(S)-Methyl-3-(2,3-dihydrobenzofuran-7-thio) propionaldehyde (IIc)

The title compound (IIc) is obtained by carrying out the preparation as in example 7 but by using, in stage 1, 2,3-dihydrobenzofuran-7-thiol (IVd) instead of 2-methoxythiophenol. This title compound, like the aldehyde (IIb-1), is not isolated but is used in situ in the following reductive amination reaction.

Example 10

2-(S)-Ethyl-3-(2-methoxyphenylthio)-propionaldehyde (IId-1)

Stage 1: 2-(R)-Ethyl-3-benzyloxypropan-1-ol (XVIId-1)

3.08 g (0.0084 mol) of 4-(R)-benzyl-3-(2-(R)-(benzyloxymethylbutyryl)oxazolidin-2-one (XVId-1), 70 ml of ethyl ether and 0.17 ml (0.0092 mol) of water are introduced into a round-bottomed flask kept under an inert atmosphere. The mixture is cooled to 0° C. and then 4.6 ml (0.0092 mol) of lithium borohydride (2N) in tetrahydrofuran are added dropwise. The mixture is stirred at 0° C. for 1 hour and then an aqueous sodium hydroxide solution (1N) is introduced in an amount sufficient for the phases to become clear. The phases are separated and the aqueous phase is extracted with ethyl ether. The combined organic phases are washed with water and with brine, dried over sodium sulfate, filtered and concentrated under reduced pressure. The residue is purified by flash chromatography on silica gel (eluent: cyclohexane/ethyl acetate=70:30). 1.34 g (0.0069 mol) of the title compound (XVIId-1) are obtained in the form of a colorless oil.

Yield: 82% [α]=+21 (c=0.634, CDCl$_3$) $^1$H NMR (CDCl$_3$) δ: 0.92 (t, 3H), 1.31 (m, 2H), 1.80 (m, 1H), 2.59 (m, 1H), 3.48 (t, 1H), 3.63 (m, 2H), 3.73 (m, 1H), 4.52 (s, 1H), 4.53 (s, 1H), 7.32 (m, 5H).

Stage 2: 2-(S)-Ethyl-3-benzyloxypropyl p-toluenesulfonate (XVIIId-1)

1.34 g (0.0069 mol) of 2-(R)-ethyl-3-benzyloxypropan-1-ol (XVIId-1), 12 ml of dichloromethane, 1.31 g (0.0069 mol) of tosyl chloride and 0.084 g (0.0007 mol) of 4-dimethylaminopyridine are introduced into a round-bottomed flask kept under an inert atmosphere. The mixture is cooled to 0° C. and then 0.89 ml (0.011 mol) of pyridine is added dropwise. After leaving overnight in a refrigerator, the mixture is hydrolyzed using a 10% aqueous citric acid solution. The phases are separated and the aqueous phase is extracted with ethyl ether. The combined organic phases are washed with water and with brine, dried over magnesium sulfate, filtered and concentrated under reduced pressure. The residue is purified by flash chromatography on silica gel (eluent: dichloromethane/cyclohexane=750:25). 1.54 g (0.0044 mol) of the title compound (XVIIId-1) are obtained.

Yield: 64% [α]=+4 (c=0.326, CDCl$_3$) $^1$H NMR (CDCl$_3$) δ: 0.85 (t, 3H), 1.37 (m, 2H), 1.84 (m, 1H), 2.41 (s, 3H), 3.38 (m, 2H), 4.07 (s, 1H), 4.08 (s, 1H), 4.38 (s, 2H), 7.28 (m, 7H), 7.78 (d, 2H).

Stage 3: 2-(S)-Ethyl-3-hydroxypropyl p-toluene-sulfonate (XIXd-1)

1.5 g (0.0043 mol) of 2-(S)-ethyl-3-benzyloxypropyl p-toluenesulfonate (XVIIId-1), 12 ml of ethanol and 0.29 g of 20% palladium hydroxide are introduced into a 100 ml round-bottomed flask. The mixture is vigorously stirred at ambient temperature under a slight hydrogen pressure. After reacting for one hour, the mixture is filtered through celite and the solid is washed with ethanol. The filtrate is concentrated under reduced pressure and the residue is purified by flash chromatography on silica gel (eluent: dichloromethane/cyclohexane=80:20). 1.02 g (0.0039 mol) of the title compound (XIXd-1) are recovered in the form of a colorless oil.

Yield: 92% [α]=−6.2 (c=0.423, CDCl$_3$) $^1$H NMR (CDCl$_3$) δ: 0.88 (t, 3H), 1.33 (m, 2H), 1.52 (t, 1H), 1.74 (m, 1H), 2.45 (s, 3H), 3.57 (m, 1H), 3.65 (m, 1H), 4.05 (dd, 1H), 4.12 (dd, 1H), 7.35 (d, 2H), 7.80 (d, 2H).

Stage 4: 2-(S)-Ethyl-3-(2-methoxyphenylthio)-propan-1-ol (XXd-1)

0.47 ml (0.0038 mol) of 2-methoxythiophenol, in solution in 5 ml of dimethylformamide, is added dropwise to a round-bottomed flask, kept under an inert atmosphere, comprising 0.19 g (0.0047 mol) of sodium hydride in suspension in 10 ml of dimethylformamide cooled to 0° C. The mixture is reheated to ambient temperature and stirred for 1 hour, then 0.99 g (0.0038 mol) of 2-(S)-ethyl-3-hydroxypropyl p-toluene-sulfonate (XIXd-1), in solution in 10 ml of dimethyl-formamide, is added. After stirring at ambient temperature for 2 hours, the dimethylformamide is evaporated under high vacuum and the residue is taken up in dichloromethane. The organic phase is washed with water and with brine, dried over sodium sulfate, filtered and concentrated under reduced pressure. The residue is purified by flash chromatography on silica gel (eluent: dichloromethane/methanol=98:2). 0.87 g (0.0038 mol) of the title compound (XXd-1) is recovered in the form of an oil.

Yield: 100% $^1$H NMR (CDCl$_3$) δ: 0.94 (t, 3H), 1.49 (m, 2H), 1.74 (m, 1H), 1.80 (m, 1H), 2.98 (m, 2H), 3.68 (m, 1H), 3.76 (m, 1H), 3.90 (s, 3H), 6.86 (d, 1H), 6.93 (td, 1H), 7.19 (td, 1H), 7.32 (dd, 1H). HPLC (Chiracel OD, hexane/isopropanol (90:10), 1 ml/min): compound (XXd-1), retention time=11.44 min; compound (XXd-2), retention time=13.23 min; ratio of the AUCs (XXd-1)/(XXd-2)=99.9:0.1.

Stage 5: 2-(S)-Ethyl-3-(2-methoxyphenylthio)-propionaldehyde (IId-1)

The title compound (IId-1) is obtained by carrying out the preparation as in example 7 but by replacing, in stage 2, 2-(S)-methyl-3-(2-methoxyphenylthio)propan-1-ol (XXb-1) with 2-(S)-ethyl-3-(2-methoxy-phenylthio)propan-1-ol (XXd-1). This title compound, like the aldehyde (IIb-1), is not isolated but is used in situ in the following reductive amination reaction.

Example 11

2-(R)-Ethyl-3-(2-methoxyphenylthio)-propionaldehyde (IId-2)

The title compound (IId-2) is obtained by carrying out the preparation as in example 10 but by replacing, in stage 1, 4-(R)-benzyl-3-(2-(R)-(benzyloxymethyl)-butyryl)oxazolidin-2-one (XVId-1) with 4-(S)-benzyl-3-(2-(S)-(benzyloxymethyl)butyryl)oxazolidin-2-one (XVId-2). This title compound, like the aldehyde (IId-1), is not isolated but is used in situ in the following reductive amination reaction.

Example 12

2-(S)-(n-Propyl)-3-(2-methoxyphenylthio)-propionaldehyde (IIe-1)

The title compound (IIe-1) is obtained by carrying out the preparation as in example 10 but by using, in stage 1, 4-(R)-benzyl-3-(2-(R)-(benzyloxymethyl)-pentanoyl)oxazolidin-2-one (XVIe-1) instead of 4-(R)-benzyl-3-(2-(R)-(benzyloxymethyl)butyryl)oxazolidin-2-one (XVId-1). This title compound, like the aldehyde (IId-1), is not isolated but is used in situ in the following reductive amination reaction.

Example 13

2-(R)-(n-Propyl)-3-(2-methoxyphenylthio)-propionaldehyde (IIe-2)

The title compound (IIe-2) is obtained by carrying out the preparation as in example 10 but by using, in stage 1, 4-(S)-benzyl-3-(2-(S)-(benzyloxymethyl)-pentanoyl)oxazolidin-2-one (XVIe-2) instead of 4-(R)-benzyl-3-(2-(R)-(benzyloxymethyl)butyryl)oxazolidin-2-one (XVId-1). This title compound, like the aldehyde (IId-1), is not isolated but is used in situ in the following reductive amination reaction.

Example 14

2-(S)-Isopropyl-3-(2-methoxyphenylthio)-propionaldehyde (IIf)

The title compound (IIf) is obtained by carrying out the preparation as in example 10 but by using, in stage 1, 4-(R)-benzyl-3-(2-(R)-benzyloxymethyl-3-methylbutyryl)oxazolidin-2-one (XVIf) instead of 4-(R)-benzyl-3-(2-(R)-(benzyloxymethyl)butyryl)oxazolidin-2-one (XVId-1). This title compound, like the aldehyde (IId-1), is not isolated but is used in situ in the following reductive amination reaction.

Example 15

2-(S)-Methyl-3-(2,3-dimethoxyphenylthio)-propionaldehyde (IIg)

Stage 1: 2-Mercapto-6-methoxyphenol (IVg)

The compound (IVg) is prepared from guaiacol according to the method reported by Tanabe (Heterocycles, 1999, 50(2), 681). The crude reaction product is taken up in a tetrahydrofuran/water (1:1) mixture and treated with 1 equivalent of triphenylphosphine at 60° C. for 2 to 3 hours and then with an aqueous sodium hydroxide solution (1N). The mixture is washed with pentane and then with dichloromethane. The aqueous phase is acidified with an aqueous hydrochloric acid solution (1N) and extracted with ethyl acetate. The ethyl acetate phase is dried over sodium sulfate, filtered and concentrated under reduced pressure to give a yellow oil which is used without additional purification in the following stage.

$^1$H NMR (d$_6$-DMSO) δ: 3.77 (s, 3H), 4.58 (s, 1H), 6.67 (m, 1H), 6.74 (dd, 1H), 6.81 (dd, 1H), 9.12 (s, 1H).

Stage 2: 2-(S)-Methyl-3-(2-hydroxy-3-methoxy-phenylthio)propan-1-ol (XXg)

0.57 g of 2-mercapto-6-methoxyphenol (IVg), in solution in 5 ml of dimethylformamide, is introduced dropwise into a round-bottomed flask, kept under an inert atmosphere, comprising 0.13 g (0.0032 mol) of sodium hydride and 5 ml of dimethylformamide. After 30 minutes, 0.34 ml (0.0033 mol) of bromo-2-(S)-methyl-1-propanol is added and the mixture is stirred at ambient temperature for 5 hours. The mixture is concentrated under reduced pressure, taken up in an aqueous hydrochloric acid solution (1N) and extracted with dichloromethane. The combined organic phases are dried over sodium sulfate, filtered and concentrated and the residue is purified by flash chromatography on silica gel (eluent: dichloromethane). 0.615 g (0.0027 mol) of the title compound (XXg) is recovered in the form of a yellow oil.

Yield: 84% $^1$H NMR (d$_6$-DMSO) δ: 0.93 (d, 3H), 1.69 (m, 1H), 2.58 (dd, 1H), 2.97 (dd, 1H), 3.32 (m, 2H), 3.78 (s, 3H), 4.58 (bs, 1H), 6.77 (m, 3H), 8.87 (bs, 1H).

Stage 3: 2-(S)-Methyl-3-(2,3-dimethoxyphenylthio)-propan-1-ol (XXIb)

0.43 g (0.0019 mol) of 2-(S)-methyl-3-(2-hydroxy-3-methoxyphenylthio)propan-1-ol (XXg), 10 ml of acetone and 0.26 g (0.0019 mol) of potassium carbonate are introduced into a round-bottomed flask kept under an inert atmosphere. After 15 minutes, 0.12 ml (0.0019 mol) of methyl iodide is introduced and the mixture is heated at 60° C. for 8 hours. The mixture is concentrated under reduced pressure. The residue is taken up in water and the aqueous phase is extracted with dichloromethane. The combined organic phases are dried over magnesium sulfate, filtered and concentrated. The residue obtained is used without additional purification in the following stage.

$^1$H NMR (d$_6$-DMSO) δ: 0.95 (d, 3H), 1.75 (m, 1H), 2.62 (dd, 1H), 3.02 (dd, 1H), 3.37 (m, 2H), 3.70 (s, 3H), 3.79 (s, 3H), 4.63 (t, 1H), 6.85 (m, 2H), 7.04 (m, 1H).

Stage 4: 2-(S)-Methyl-3-(2,3-dimethoxyphenylthio)-propionaldehyde (IIg)

The title compound (IIg) is obtained by carrying out the preparation as in example 7 but by using, in stage 2, 2-(S)-methyl-3-(2,3-dimethoxyphenylthio)-propan-1-ol (XXIb) instead of 2-(S)-methyl-3-(2-methoxyphenylthio)propan-1-ol (XXb-1). This title compound, like the aldehyde (IIb-1), is not isolated but is used in situ in the following reductive amination reaction.

Example 16

3-(R)-([(S)-3,4-Epoxypropyl]amino)-3,4-dihydro-2H-1,5-benzoxathiepine (III-1)

0.85 g (0.0047 mole) of 3-(R)-amino-3,4-dihydro-2H-1,5-benzoxathiepine (Ia-1), 15 ml of 2-propanol and 0.41 ml (0.0052 mol) of (S)-epichlorohydrin are introduced into a round-bottomed flask kept under an inert atmosphere. The mixture is brought to 60° C. for 12 hours and then cooled to ambient temperature. 0.37 g (0.0066 mol) of ground potassium hydroxide is then added and, after stirring at ambient temperature for 3 hours, the solvent is evaporated under reduced pressure. The residue is taken up in dichloromethane. The solution obtained is washed with water and with brine, dried over magnesium sulfate, filtered and concentrated under reduced pressure. The residue is purified by flash chromatography on silica gel (eluent: dichloromethane/methanol=98:2). 0.69 g (0.0029 mol) of the title compound (III-1) is obtained.

Yield: 62% $[\alpha]$=+22.1 (c=0.227, methanol) $^1$H NMR ($d_6$-DMSO) δ: 2.17 (bs, 1H), 2.56 (dd, 1H), 2.65 (m, 2H), 2.84 (m, 2H), 3.00 (m, 1H), 3.11 (m, 1H), 3.17 (bs, 1H), 3.93 (dd, 1H), 4.16 (dd, 1H), 6.98 (m, 2H), 7.18 (td, 1H), 7.34 (d, 1H) HPLC (Chiralpack AD, hexane/ethanol (90:10), 1 ml/min): compound (III-1), retention time=24.04 min; compound (III-2), retention time=29.81 min, ratio of the AUCs (III-1)/(III-2)=97:3

Example 17

3-(R)-([(R)-3,4-Epoxypropyl]amino)-3,4-dihydro-2H-1,5-benzoxathiepine (III-2)

The title compound (III-2) is obtained, in the form of a white oil, by carrying out the preparation as in example 16 but by replacing (S)-epichlorohydrin with (R)-epichlorohydrin.

Yield: 55% $[\alpha]$=+56 (c=0.256, methanol) $^1$H NMR ($CDCl_3$) δ: 2.08 (bs, 1H), 2.65 (m, 1H), 2.75 (dd, 1H), 2.80 (m, 1H), 2.97 (dd, 1H), 3.05 (dd, 1H), 3.12 (m, 2H), 3.28 (m, 1H), 4.09 (dd, 1H), 4.29 (dd, 1H), 6.96 (m, 2H), 7.14 (td, 1H), 7.35 (dd, 1H).

Example 18

2-(S)-Methyl-3-(2-(methoxymethoxy)phenylthio)propionaldehyde (Vb)

Stage 1: 2-(S)-Methyl-3-(2-hydroxyphenylthio)-propan-1-ol (XXh)

The title compound (XXh) is obtained by carrying out the preparation as in example 7 but by replacing, in stage 1, 2-methoxythiophenol with 2-hydroxythiophenol.

Yield: 100% $^1$H NMR ($d_6$-DMSO) δ: 0.94 (d, 3H), 1.71 (m, 1H), 2.58 (dd, 1H), 2.98 (dd, 1H), 3.34 (m, 2H), 4.59 (bs, 1 exchangeable H), 6.77 (m, 2H), 7.00 (m, 1H), 7.18 (m, 1H), 9.68 (bs, 1 exchangeable H).

Stage 2: 2-(S)-Methyl-3-(2-(methoxymethoxy)-phenylthio)propan-1-ol (XXIa)

2.47 g (0.012 mol) of 2-(S)-methyl-3-(2-hydroxyphenylthio)propan-1-ol (XXh), 25 ml of dichloromethane, 12.5 ml (0.024 mol) of an aqueous sodium hydroxide solution (2N), 0.55 ml (0.0012 mol) of Aliquat 336 and 0.9 ml (0.012 mol) of chloromethyl methyl ether are introduced into a 100 ml round-bottomed flask. The mixture is stirred at ambient temperature for 24 hours and then the phases are separated. The organic phase is washed successively with an aqueous hydrochloric acid solution (1N), an aqueous sodium hydroxide solution (1N), water and brine and then dried over sodium sulfate, filtered and concentrated under reduced pressure. The residue is purified by flash chromatography on silica gel (eluent: dichloromethane/acetone=96:4). 1.1 g (0.0045 mol) of the title compound (XXIa) are recovered in the form of a white oil.

Yield: 38% $^1$H NMR ($d_6$-DMSO) δ: 0.96 (d, 3H), 1.74 (m, 1H), 2.63 (dd, 1H), 3.04 (dd, 1H), 3.36 (t, 2H), 3.40 (s, 3H), 4.62 (t, 1 exchangeable H), 5.23 (s, 2H), 6.98 (td, 1H), 7.05 (dd, 1H), 7.12 (td, 1H), 7.25 (dd, 1H).

Stage 3: 2-(S)-Methyl-3-(2-(methoxymethoxy)phenylthio)propionaldehyde (Vb)

The title compound (Vb) is obtained by carrying out the preparation as in example 7 but by using, in stage 2, 2-(S)-methyl-3-(2-(methoxymethoxy)phenylthio)propan-1-ol (XXIa) instead of 2-(S)-methyl-3-(2-methoxyphenylthio)propan-1-ol (XXb-1). This title compound, like the aldehyde (IIb-1), is not isolated but is used in situ in the following reductive amination reaction.

Example 19

2-(S)-Methyl-3-(2-methoxymethoxy-3-methylphenylthio)propionaldehyde (Vc)

The title compound (Vc) is obtained by carrying out the preparation as in example 18 but by using, in stage 1, 2-hydroxy-3-methylthiophenol (IVa) instead of 2-hydroxythiophenol. This title compound, like the aldehyde (Vb), is not isolated but is used in the following reductive amination reaction.

Example 20

2-(S)-Methyl-3-(2-methoxymethoxy-3-ethylphenylthio)propionaldehyde (Vd)

The title compound (Vd) is obtained by carrying out the preparation as in example 18 but by using, in stage 1, 2-hydroxy-3-ethylthiophenol (IVe) instead of 2-hydroxythiophenol. This title compound, like the aldehyde (Vb), is not isolated but is used in the following reductive amination reaction.

Example 21

2-(S)-Ethyl-3-(2-methoxymethoxy-3-methylphenylthio)propionaldehyde (Ve)

Stage 1: 2-(S)-Ethyl-3-(2-hydroxy-3-methylphenylthio)propan-1-ol (XXj)

0.78 g (0.0034 mol) of the title compound (XXj), in the form of an orange-colored oil, are obtained by carrying out the preparation as in example 10 but by replacing, in stage 4, 2-methoxythiophenol with 2-hydroxy-3-methylthiophenol (IVa).

Yield: 79% $^1$H NMR ($d_6$-DMSO) δ: 0.84 (t, 3H), 1.40 (m, 2H), 1.51 (m, 1H), 2.16 (s, 3H), 2.71 (dd, 1H), 2.86 (dd, 1H), 3.39 (dd, 1H), 3.46 (dd, 1H), 4.55 (bs, 1 exchangeable H), 6.73 (t, 1H), 6.96 (d, 1H), 7.10 (d, 1H), 8.48 (bs, 1 exchangeable H).

Stage 2: 2-(S)-Ethyl-3-(2-methoxymethoxy-3-methylphenylthio)propionaldehyde (Ve)

The title compound (Ve) is obtained by carrying out the preparation as in example 18 but by using, in stage 2, 2-(S)-ethyl-3-(2-hydroxy-3-methylphenylthio)-propan-1-ol (XXj) instead of 2-(S)-methyl-3-(2-hydroxyphenylthio)propan-1-ol (XXh). This title compound, like the aldehyde (Vb), is not isolated but is used in situ in the following reductive amination reaction.

Example 22

2-(S)-Isopropyl-3-(2-methoxymethoxy-3-methylphenylthio)propionaldehyde (Vf)

The title compound (Vf) is obtained by carrying out the preparation as in example 21 but by using, in stage 1, 2-(S)-isopropyl-3-hydroxypropyl p-toluene-sulfonate (XIXf) instead of 2-(S)-ethyl-3-hydroxypropyl p-toluene-sulfonate (XIXd-1). This title compound, like the aldehyde (Vb), is not isolated but is used in situ in the following reductive amination reaction.

Example 23

2-(S)-Methyl-3-(2-methoxymethoxy-3-methoxyphenylthio)propionaldehyde (Vg)

The title compound (Vg) is obtained by carrying out the preparation as in example 18 but by using, in stage 1, 2-mercapto-6-methoxyphenol (IVg) instead of 2-hydroxythiophenol. This title compound, like the aldehyde (Vb), is not isolated but is used in situ in the following reductive amination reaction.

Example 24

2-(S)-Methyl-3-(2-methoxymethoxy-3-(isopropyl)phenylthio)propionaldehyde (Vh)

Stage 1: 2-Hydroxy-3-(isopropyl)thiophenol (IVh)

The title compound (IVh) is obtained, in the form of a yellow oil, by carrying out the preparation as in example 15 but by using, in stage 1, 2-isopropylphenol instead of guaiacol. This title compound is used in the crude form in the following S-alkylation stage, resulting in the intermediate (XXh).

$^1$H NMR (d$_6$-DMSO) δ: 1.14 (d, 6H), 3.27 (m, 1H), 4.64 (bs, 1H), 6.73 (m, 1H), 6.96 (m, 1H), 7.10 (m, 1H), 8.54 (bs, 1H).

Stage 2: 2-(S)-Methyl-3-(2-methoxymethoxy-3-(isopropyl)phenylthio)propionaldehyde (Vh)

The title compound (Vh) is obtained by carrying out the preparation as in example 18 but by using, in stage 1, 2-hydroxy-3-(isopropyl)thiophenol (IVh) instead of 2-hydroxythiophenol. This title compound, like the aldehyde (Vb), is not isolated but is used in situ in the following reductive amination reaction.

Example 25

2-(S)-Methyl-3-(2-methoxymethoxy-6-methylphenylthio)propionaldehyde (Vj)

The title compound (Vj) is obtained by carrying out the preparation as in example 18 but by using, in stage 1, 2-hydroxy-6-methylphenol (IVc) instead of 2-hydroxythiophenol. This title compound, like the aldehyde (Vb), is not isolated but is used in situ in the following reductive amination reaction.

Example 26

3-(R)-[3-(2-Methoxymethoxy-3-methylphenylthio)-2-(S)-ethylpropyl]amino-3,4-dihydro-2H-1,5-benzoxathiepine (VIa)

The amounts of the amine of formula (I) and of the reducing agent used in the reductive amination reaction are calculated on the basis of a quantitative oxidation reaction of the alcohol of formula (XXI) to the aldehyde of formula (V). 0.43 g (0.0024 mol) of 3-(R)-amino-3,4-dihydro-2H-1,5-benzoxathiepine (Ia-1), in solution in 5 ml of dichloromethane, is added to a solution, held at −10° C., of the aldehyde (Ve), 0.0023 mol theoretically, composed of the reaction medium from the reaction of the oxidation of the alcohol (XXIJ) to the aldehyde (Ve). After stirring at −10° C. for 10 minutes, 0.75 g (0.0035 mol) of sodium triacetoxyborohydride is added and the mixture is stirred at −10° C. for 1 hour 30 and then hydrolyzed using a 10% aqueous sodium carbonate solution. The phases are separated and the aqueous phase is extracted with dichloromethane. The combined organic phases are washed with water and with brine, dried over magnesium sulfate, filtered and concentrated under reduced pressure. The residue is purified by flash chromatography on silica gel (eluent=cyclohexane/ethyl acetate=70:30). 0.42 g (0.0097 mol) of the title compound (VIa) is recovered in the form of an oil.

Yield: 41% $^1$H NMR (d$_6$-DMSO) δ: 0.88 (t, 3H), 1.45 (m, 2H), 1.60 (m, 1H), 1.98 (m, 1H), 2.24 (s, 3H), 2.64 (bs, 2H), 2.84 (m, 2H), 3.05 (m, 3H), 3.53 (s, 3H), 3.93 (dd, 1H), 4.14 (dd, 1H), 4.99 (s, 2H), 7.00 (m, 4H), 7.18 (m, 2H), 7.46 (d, 1H).

Example 27

3-(R)-[3-(2-Methoxymethoxy-3-methylphenylthio)-2-(S)-methylpropyl]amino-3,4-dihydro-2H-1,5-benzoxathiepine (VIb)

The title compound (VIb) is obtained by carrying out the preparation as in example 26 but by using 2-(S)-methyl-3-(2-methoxymethoxy-3-methylphenylthio)-propionaldehyde (Vc) instead of 2-(S)-ethyl-3-(2-methoxymethoxy-3-methylphenylthio)propionaldehyde (Ve).

Yield: 70% $^1$H NMR (d$_6$-DMSO) δ: 1.00 (d, 3H), 1.76 (m, 1H), 2.02 (bs, 1 exchangeable H), 2.24 (s, 3H), 2.60 (m, 2H), 2.70 (dd, 1H), 2.81 (dd, 1H), 3.09 (m, 3H), 3.53 (s, 3H), 3.92 (dd, 1H), 4.16 (dd, 1H), 4.99 (s, 2H), 7.00 (m, 4H), 7.17 (m, 2H), 7.33 (d, 1H).

Example 28

3-(R)-[3-(2-Methoxymethoxy-3-methylphenylthio)-2-(S)-(isopropyl)propyl]amino-3,4-dihydro-2H-1,5-benzoxathiepine (VIc)

The title compound (VIc) is obtained by carrying out the preparation as in example 26 but by using 2-(S)-isopropyl-3-(2-methoxymethoxy-3-methylphenylthio)propionaldehyde (Vf) instead of 2-(S)-ethyl-3-(2-methoxymethoxy-3-methylphenylthio)propionaldehyde (Ve). This title compound is used without additional purification in the following stage.

Yield: 18%

Example 29

3-(R)-[3-(2-(Methoxymethoxy)phenylthio)-2-(S)-methylpropyl]amino-3,4-dihydro-2H-1,5-benzoxathiepine (VId)

The title compound (VId) is obtained by carrying out the preparation as in example 26 but by using 2-(S)-methyl-3-(2-(methoxymethoxy)phenylthio)propionaldehyde (Vb) instead of 2-(S)-ethyl-3-(2-(methoxy-methoxy)-3-methylphenylthio)propionaldehyde (Ve).

Yield: 77% $^1$H NMR (d$_6$-DMSO) δ: 1.01 (d, 3H), 1.77 (m, 1H), 2.02 (bs, 1 exchangeable H), 2.60 (m, 2H), 2.70 (dd, 1H), 2.81 (dd, 1H), 3.10 (m, 3H), 3.40 (s, 3H), 3.92 (dd, 1H), 4.16 (dd, 1H), 5.23 (s, 2H), 7.10 (m, 6H), 7.32 (m, 2H)

Example 30

3-(R)-[3-(2-Methoxymethoxy-3-ethylphenylthio)-2-(S)-methylpropyl]amino-3,4-dihydro-2H-1,5-benzoxathiepine (VIe)

The title compound (VIe) is obtained by carrying out the preparation as in example 26 but by using 2-(S)-methyl-3-(2-methoxymethoxy-3-ethylphenylthio)-propionaldehyde (Vd) instead of 2-(S)-ethyl-3-(2-methoxymethoxy-3-methylphenylthio)propionaldehyde (Ve).

Yield: 23% $^1$H NMR (CDCl$_3$) δ: 1.09 (d, 3H), 1.22 (t, 3H), 1.83 (bs, 1H), 1.93 (m, 1H), 2.72 (m, 5H), 2.95 (dd, 1H), 3.09 (m, 3H), 3.64 (s, 3H), 5.08 (s, 2H), 4.06 (dd, 1H), 4.25 (dd, 1H), 6.99 (m, 4H), 7.14 (m, 2H), 7.35 (dd, 1H).

Example 31

3-(R)-[3-(2-Methoxymethoxy-3-(isopropyl)-phenylthio)-2-(S)-methylpropyl]amino-3,4-dihydro-2H-1,5-benzoxathiepine (VIh)

The title compound (VIh) is obtained by carrying out the preparation as in example 26 but by using 2-(S)-methyl-3-(2-methoxymethoxy-3-(isopropyl)phenylthio)propionaldehyde (Vh) instead of 2-(S)-ethyl-3-(2-methoxymethoxy-3-methylphenylthio)propionaldehyde (Ve).

Yield: 30% $^1$H NMR (CDCl$_3$) δ: 1.10 (d, 3H), 1.21 (d, 6H), 1.70 (bs, 1H), 1.92 (m, 1H), 2.63 (dd, 1H), 2.77 (m, 2H), 2.94 (dd, 1H), 3.10 (m, 3H), 3.42 (m, 1H), 3.64 (s, 3H), 4.06 (dd, 1H), 4.24 (dd, 1H), 5.07 (s, 2H), 6.96 (m, 2H), 7.11 (m, 4H), 7.35 (d, 1H).

Example 32

3-(R)-[3-(2-Methoxymethoxy-3-methylphenylthio)-2-(S)-methylpropyl]amino-6-methyl-3,4-dihydro-2H-1,5-benzoxathiepine (VIg)

The title compound (VIg) is obtained by carrying out the preparation as in example 26 but by using 2-(S)-methyl-3-(2-methoxymethoxy-3-methylphenylthio)-propionaldehyde (Vc) instead of 2-(S)-ethyl-3-(2-methoxymethoxy-3-methylphenylthio)propionaldehyde (Ve) and 3-(R)-amino-6-methyl-3,4-dihydro-2H-1,5-benzoxathiepine (Ic) instead of 3-(R)-amino-3,4-dihydro-2H-1,5-benzoxathiepine (Ia-1).

Yield: 52% $^1$H NMR (d$_6$-DMSO) δ: 1.00 (d, 3H), 1.78 (bs, 1H), 2.24 (s, 3H), 2.31 (s, 3H), 2.55 (bs, 1H), 2.69 (m, 2H), 2.86 (bs, 1H), 3.10 (m, 3H), 3.53 (s, 3H), 3.94 (bs, 1H), 4.18 (bd, 1H), 4.99 (s, 2H), 6.81 (d, 1H), 6.92 (d, 1H), 7.03 (m, 3H), 7.18 (m, 1H).

Example 33

3-(R)-[3-(2-Methoxymethoxy-3-methoxyphenylthio)-2-(S)-methylpropyl]amino-3,4-dihydro-2H-1,5-benzoxathiepine (VIi)

The title compound (VIi) is obtained by carrying out the preparation as in example 26 but by using 2-(S)-methyl-3-(2-methoxymethoxy-3-methoxyphenylthio)-propionaldehyde (Vg) instead of 2-(S)-ethyl-3-(2-methoxymethoxy-3-methylphenylthio)propionaldehyde (Ve).

Yield: 76% $^1$H NMR (d$_6$-DMSO) δ: 1.00 (d, 3H), 1.77 (m, 1H), 2.02 (m, 1H), 2.55 (m, 1H), 2.64 (m, 1H), 2.70 (dd, 1H), 2.81 (dd, 1H), 3.09 (m, 3H), 3.54 (s, 3H), 3.77 (s, 3H), 3.92 (dd, 1H), 4.16 (dd, 1H), 5.05 (s, 2H), 6.96 (m, 5H), 7.17 (m, 1H), 7.33 (d, 1H).

Example 34

3-(R)-[3-(2-Methoxymethoxy-6-methylphenylthio)-2-(S)-methylpropyl]amino-3,4-dihydro-2H-1,5-benzoxathiepine (VIj)

The title compound (VIj) is obtained by carrying out the preparation as in example 26 but by using 2-(S)-methyl-3-(2-methoxymethoxy-6-methylphenylthio)-propionaldehyde (Vj) instead of 2-(S)-ethyl-3-(2-methoxymethoxy-3-methylphenylthio)propionaldehyde (Ve).

Yield: 74% $^1$H NMR (d$_6$-DMSO) δ: 0.96 (d, 3H), 1.56 (m, 1H), 1.88 (bs, 1H), 2.45 (s, 3H), 2.59 (m, 3H), 2.75 (dd, 1H), 2.89 (m, 3H), 3.42 (s, 3H), 3.86 (dd, 1H), 4.09 (dd, 1H), 5.24 (s, 2H), 6.95 (m, 4H), 7.16 (m, 2H), 7.33 (dd, 1H).

Reference Example 1

3-(R)-[3-(2-Methoxyphenylthio)-2-(S)-methoxypropyl]amino-3,4-dihydro-2H-1,5-benzoxathiepine (1-1)

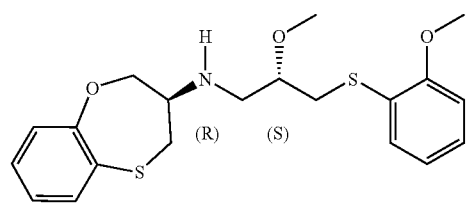

1.43 g (0.0063 mol) of 2-(S)-methoxy-3-(2-methoxyphenylthio)propionaldehyde (IIa-1) and 5 ml of 1,2-dichloroethane are introduced into a round-bottomed flask held under an inert atmosphere. 0.60 g (0.0063 mol) of 3-(R)-amino-3,4-dihydro-2H-1,5-benzoxathiepine (Ia-1), in solution in 5 ml of 1,2-dichloroethane, is added dropwise. The mixture is cooled to 0° C. and then 1 g (0.0047 mol) of sodium triacetoxyborohydride is introduced. The solution is stirred at ambient temperature for 5 hours and then hydrolyzed using a 10% aqueous sodium bicarbonate solution. The phases are separated and the aqueous phase is extracted with dichloromethane. The combined organic phases are washed with brine, dried over magnesium sulfate, filtered and concentrated under reduced pressure. The residue s purified by flash chromatography on silica gel (eluent: dichloromethane/ethyl acetate=90:10). 0.88 g (0.0022 mol) of the compound (1-1) is recovered in the form of a yellow oil.

Yield: 36% ¹H NMR (CDCl₃) δ: 1.96 (bs, 1 exchangeable H), 2.81 (dd, 1H), 2.98 (m, 2H), 3.12 (m, 4H), 3.41 (s, 3H), 3.49 (m, 1H), 3.90 (s, 3H), 4.16 (m, 2H), 6.86 (d, 1H), 6.94 (m, 3H), 7.12 (t, 1H), 7.20 (t, 1H), 7.35 (m, 2H).

0.88 g (0.0022 mol) of the product (1-1) is dissolved in 3 ml of methanol and then 0.23 g (0.0020 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.90 g (0.0018 mol) of the maleate of the compound (1-1) is obtained in the form of a white solid.

M.p. 122° C. [α]=−15.3 (c=0.300, methanol) Analysis C₂₄H₂NO₇S₂:

| Calc. %: | C 56.79 | H 5.76 | N 2.76 |
|---|---|---|---|
| Found: | C 56.42 | H 5.81 | N 2.96 |

¹H NMR (d₆-DMSO) δ: 3.22 (m, 8H), 3.36 (s, 3H), 3.78 (bs, 1H), 3.84 (s, 3H), 4.30 (bd, 1H), 4.46 (bd, 1H), 6.04 (s, 2H), 7.00 (m, 4H), 7.24 (m, 2H), 7.38 (m, 2H), 8.90 (bs, 2 exchangeable H) HPLC (Chiracel OD, hexane/isopropanol (90:10), 1 ml/min): compound (1-1), retention time=25.40 min; compound (1-2), retention time=21.99 min; ratio of the AUCs (1-1)/(1-2)=95:5.

Reference Example 2

3-(R)-[3-(2-Methoxyphenylthio)-2-(R)-methoxypropyl]amino-3,4-dihydro-2H-1,5-benzoxathiepine (1-2)

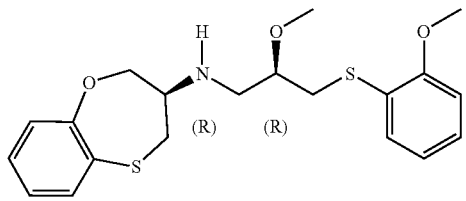

The compound (1-2) is obtained by carrying out the preparation as in reference example 1 but by using 2-(R)-methoxy-3-(2-methoxyphenylthio)propionaldehyde (IIa-2) instead of 2-(S)-methoxy-3-(2-methoxyphenylthio)propionaldehyde (IIa-1).

Yield: 33% ¹H NMR (CDCl₃) δ: 1.95 (bs, 1 exchangeable H), 3.03 (m, 7H), 3.41 (s, 3H), 3.50 (m, 1H), 3.90 (s, 3H), 4.16 (m, 2H), 6.86 (d, 1H), 6.93 (m, 3H), 7.12 (td, 1H), 7.21 (td, 1H), 7.34 (m, 2H).

0.79 g (0.002 mol) of the product (1-2) is dissolved in 3 ml of methanol and then 0.21 g (0.0018 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.90 g (0.0018 mol) of the maleate of the compound (1-2) is obtained in the form of a white solid.

M.p.: 116° C. [α]=+60.5 (c=0.228, methanol) Analysis C₂₄H₂₉NO₇S₂:

| Calc. %: | C 56.79 | H 5.76 | N 2.76 |
|---|---|---|---|
| Found: | C 56.55 | H 5.69 | N 2.92 |

¹H NMR (d₆-DMSO) δ: 3.21 (m, 8H), 3.36 (s, 3H), 3.81 (bs, 1H), 3.84 (s, 3H), 4.26 (bd, 1H), 4.43 (bd, 1H), 6.04 (s, 2H), 7.03 (m, 4H), 7.24 (m, 2H), 7.35 (d, 1H), 7.42 (d, 1H), 8.83 (bs, 2 exchangeable H) HPLC (Chiracel OD, hexane/isopropanol (90:10), 1 ml/min): compound (1-2), retention time=20.75 min; compound (1-1), retention time=25.47 min; ratio of the AUCs (1-2)/(1-1)=86:14.

Reference Example 3

3-(R)-[3-(2-Hydroxyphenylthio)-2-(S)-hydroxypropyl]amino-3,4-dihydro-2H-1,5-benzoxathiepine (1-3)

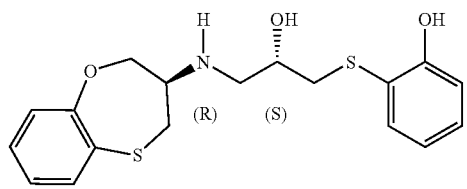

0.5 g (0.0021 mol) of 3-(R)-([(S)-3,4-epoxypropyl] amino)-3,4-dihydro-2H-1,5-benzoxathiepine (III-1) and 15 ml of ethanol are introduced into a round-bottomed flask kept under an inert atmosphere. 0.22 ml (0.0021 mol) of 2-hydroxythiophenol is subsequently added dropwise, followed, after stirring at ambient temperature for 15 minutes, by 0.45 g (0.0042 mol) of sodium carbonate. The mixture is stirred at ambient temperature for 12 hours and then concentrated under reduced pressure. The residue is taken up in dichloromethane and the solution obtained is washed with water and then dried over sodium sulfate, filtered and concentrated under vacuum. The residue is purified by flash chromatography on silica gel (eluent: dichloromethane/methanol=96:4). 0.58 g (0.0016 mol) of the compound (1-3) is recovered in the form of a pale yellow oil.

Yield: 76% ¹H NMR (d₆-DMSO) δ: 2.60 (m, 1H), 2.93 (m, 6H), 3.63 (m, 1H), 3.97 (dd, 1H), 4.12 (dd, 1H), 6.78 (m, 2H), 7.00 (m, 3H), 7.17 (td, 1H), 7.25 (dd, 1H), 7.33 (dd, 1H).

0.57 g (0.0016 mol) of the product (1-3) is dissolved in 3 ml of methanol and then 0.13 g (0.0014 mol) of oxalic acid, dissolved in 2 ml of methanol, is added. The solution obtained is concentrated and then ethyl ether is added. The precipitate formed is filtered off, washed with ethyl ether and dried under vacuum at 50° C. 0.52 g (0.0011 mol) of the oxalate of the compound (1-3) is obtained in the form of a white solid.

M.p.: 176–7° C. [α]=−5.2 (c=0.309, methanol) Analysis C₂₀H₂₃NO₇S₂:

| Calc. %: | C 52.96 | H 5.11 | N 3.09 |
| --- | --- | --- | --- |
| Found: | C 52.90 | H 5.15 | N 3.26 |

$^1$H NMR (d$_6$-DMSO) δ: 2.97 (m, 3H), 3.22 (m, 3H), 3.72 (bs, 1H), 3.91 (m, 1H), 4.35 (m, 2H), 6.79 (td, 1H), 6.85 (dd, 1H), 7.06 (m, 3H), 7.24 (m, 2H), 7.40 (dd, 1H). HPLC (Chiralpack AD, hexane/ethanol (50:50), 1 ml/min): compound (1-3), retention time=23.08 min; compound (1-4), retention time=19.40 min; ratio of the AUCs (1-3)/(1-4)=99:1.

Reference Example 4

3-(R)-[3-(2-Hydroxyphenylthio)-2-(R)-hydroxypropyl]amino-3,4-dihydro-2H-1,5-benzoxathiepine (1-4)

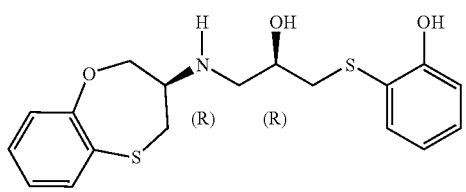

The compound (1-4) is obtained by carrying out the preparation as in reference example 3 but by using 3-(R)-([(R)-3,4-epoxypropyl]amino)-3,4-dihydro-2H-1,5-benzoxathiepine (III-2) instead of 3-(R)-([(S)-3,4-epoxypropyl]amino)-3,4-dihydro-2H-1,5-benzoxathiepine (III-1).

Yield: 95% $^1$H NMR (d$_6$-DMSO) δ: 2.68 (m, 2H), 2.89 (m, 3H), 3.10 (m, 2H), 3.63 (m, 1H), 3.93 (dd, 1H), 4.12 (dd, 1H), 6.79 (m, 2H), 7.00 (m, 3H), 7.17 (td, 1H), 7.25 (dd, 1H), 7.34 (dd, 1H).

0.50 g (0.0014 mol) of the product (1-4) is dissolved in 3 ml of methanol and then 0.12 g (0.0013 mol) of oxalic acid, dissolved in 2 ml of methanol, is added. The solution obtained is concentrated. The precipitate formed is filtered off, washed with ethyl ether and dried under vacuum at 50° C. 0.53 g (0.0011 mol) of the oxalate of the compound (1-4) is obtained in the form of a white solid.

M.p.: 135° C. [α]=+60.48 (c=0.248, methanol) Analysis C$_{20}$H$_{23}$NO$_7$S$_2$:

| Calc. %: | C 52.96 | H 5.11 | N 3.09 |
| --- | --- | --- | --- |
| Found: | C 53.33 | H 5.12 | N 3.15 |

$^1$H NMR (d$_6$-DMSO) δ: 2.96 (m, 3H), 3.23 (m, 3H), 3.68 (bs, 1H), 3.90 (m, 1H), 4.46 (m, 2H), 6.79 (t, 1H), 6.85 (d, 1H), 7.05 (m, 3H), 7.25 (m, 2H), 7.40 (dd, 1H). HPLC (Chiralpack AD, hexane/ethanol (50:50), 1 ml/min): compound (1-4), retention time=18.70 min; compound (1-3), retention time=22.71 min; ratio of the AUCs (1-4)/(1-3)=96:4.

Reference Example 5

3-(R)-[3-(2-Methoxyphenylthio)-2-(S)-hydroxypropyl]amino-3,4-dihydro-2H-1,5-benzoxathiepine (1-5)

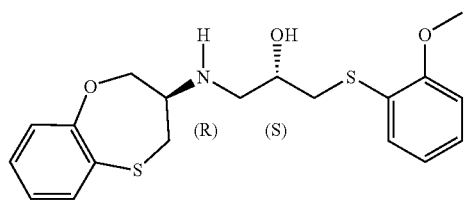

The compound (1-5) is obtained by carrying out the preparation as in reference example 3 but by using 2-methoxythiophenol instead of 2-hydroxythiophenol.

Yield: 38% $^1$H NMR (d$_6$-DMSO) δ: 2.12 (bs, 1 exchangeable H), 2.64 (m, 1H), 2.81 (m, 2H), 2.89 (dd, 1H), 3.06 (m, 3H), 3.65 (m, 1H), 3.81 (s, 3H), 3.97 (dd, 1H), 4.13 (dd, 1H), 5.07 (d, 1 exchangeable H), 6.95 (m, 4H), 7.16 (m, 2H), 7.31 (m, 2H).

0.20 g (0.0005 mol) of the product (1-5) is dissolved in 3 ml of methanol and then 0.06 g (0.0005 mol) of maleic acid, dissolved in 2 ml of methanol, is added. The solution obtained is concentrated and then ethyl ether is added. The precipitate is filtered off, washed with ethyl ether and dried under vacuum at 50° C. 0.14 g (0.0003 mol) of the maleate of the compound (1-5) is obtained in the form of a white solid.

M.p.: 133–5° C. [α]=−3.2 (c=0.436, methanol) Analysis C$_{23}$H$_{27}$NO$_7$S$_2$:

| Calc. %: | C 55.97 | H 5.51 | N 2.84 |
| --- | --- | --- | --- |
| Found: | C 55.83 | H 5.40 | N 2.93 |

$^1$H NMR (d$_6$-DMSO) δ: 3.03 (m, 3H), 3.25 (d, 2H), 3.30 (bs, 1H), 3.83 (s, 3H), 3.86 (bs, 1H), 3.99 (bs, 1H), 4.32 (bd, 1H), 4.47 (bd, 1H), 5.85 (bs, 1H), 6.03 (s, 2H), 7.00 (m, 4H), 7.22 (m, 2H), 7.32 (dd, 1H), 7.41 (dd, 1H). HPLC (Chiracel OD, hexane/ethanol (80:20), 1 ml/min): compound (1-5), retention time=20.04 min; compound (1-6), retention time=16.29 min; ratio of the AUCs (1-5)/(1-6)=95:5.

Reference Example 6

3-(R)-[3-(2-Methoxyphenylthio)-2-(R)-hydroxypropyl]amino-3,4-dihydro-2H-1,5-benzoxathiepine (1-6)

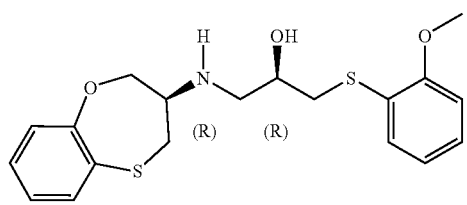

The compound (1-6) is obtained by carrying out the preparation as in reference example 5 but by using 3-(R)-

([(R)-3,4-epoxypropyl]amino)-3,4-dihydro-2H-1,5-benzoxathiepine (III-2) instead of 3-(R)-([(S)-3,4-epoxypropyl]amino)-3,4-dihydro-2H-1,5-benzoxathiepine (III-1).

Yield: 70% $^1$H NMR (d$_6$-DMSO) δ: 2.13 (bs, 1 exchangeable H), 2.68 (m, 2H), 2.88 (m, 2H), 2.99 (dd, 1H), 3.10 (m, 2H), 3.65 (m, 1H), 3.81 (s, 3H), 3.93 (dd, 1H), 4.12 (dd, 1H), 5.07 (d, 1 exchangeable H), 6.95 (m, 4H), 7.16 (m, 2H), 7.31 (m, 2H).

0.52 g (0.0014 mol) of the product (1-6) is dissolved in 3 ml of methanol and then 0.15 g (0.0013 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.59 g (0.0012 mol) of the maleate of the compound (1-6) is obtained in the form of a white solid.

M.p.: 136–8° C. [α]=+60.3 (c=0.745, methanol) Analysis $C_{23}H_{27}NO_7S_2$:

| Calc. %: | C 55.97 | H 5.51 | N 2.84 |
| Found:   | C 55.99 | H 5.59 | N 2.96 |

$^1$H NMR (d$_6$-DMSO) δ: 3.03 (m, 3H), 3.26 (d, 2H), 3.30 (bs, 1H), 3.83 (s, 3H), 3.86 (bs, 1H), 4.00 (bs, 1H), 4.26 (bd, 1H), 4.44 (bd, 1H), 5.85 (bs, 1H), 6.03 (s, 2H), 7.04 (m, 4H), 7.22 (m, 2H), 7.33 (dd, 1H), 7.43 (dd, 1H). HPLC (Chiracel OD, hexane/ethanol (80:20), 1 ml/min): compound (1-6), retention time=16.29 min; compound (1-5), retention time=20.04 min; ratio of the AUCs (1-6)/(1-5)=97:3.

Reference Example 7

3-(R)-[3-(2-Methoxyphenylthio)-2-(S)-methylpropyl]amino-3,4-dihydro-2H-1,5-benzoxathiepine (1-7)

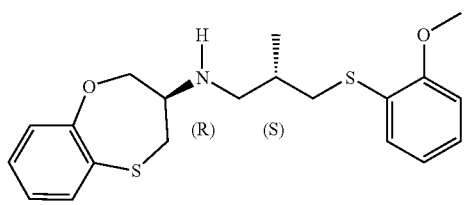

The compound (1-7) is obtained by carrying out the preparation as in example 26 but starting from the reaction mixture comprising 2-(S)-methyl-3-(2-methoxy-phenylthio)propionaldehyde (IIb-1) instead of 2-(S)-ethyl-3-(2-methoxymethoxy-3-methylphenylthio)propionaldehyde (Ve).

Yield: 58% $^1$H NMR (CDCl$_3$) δ: 1.10 (d, 3H), 1.68 (bs, 1 exchangeable H), 1.91 (m, 1H), 2.63 (dd, 1H), 2.78 (m, 2H), 2.93 (dd, 1H), 3.10 (m, 3H), 3.90 (s, 3H), 4.07 (dd, 1H), 4.23 (dd, 1H), 6.84 (d, 1H), 6.91 (m, 3H), 7.14 (m, 2H), 7.33 (m, 2H).

2.85 g (0.0076 mol) of the product (1-7) are dissolved in 5 ml of methanol and then 0.84 g (0.0072 mol) of fumaric acid, dissolved in 3 ml of methanol, is added. The solution obtained is concentrated and then isopropyl ether is added. The precipitate formed is filtered off, washed with isopropyl ether and dried under vacuum at 50° C. 3.36 g (0.0068 mol) of the fumarate of the compound (1-7) are obtained in the form of a white solid.

M.p.: 133–4° C. [α]=−1.2 (c=0.446, methanol) Analysis $C_{24}H_{29}NO_6S_2$:

| Calc. %: | C 58.63 | H 5.95 | N 2.85 |
| Found:   | C 58.53 | H 5.89 | N 2.74 |

$^1$H NMR (d$_6$-DMSO) δ: 1.01 (d, 3H), 1.80 (m, 1H), 2.59 (dd, 1H), 2.69 (m, 2H), 2.87 (dd, 1H), 3.11 (m, 3H), 3.81 (s, 3H), 3.98 (dd, 1H), 4.19 (dd, 1H), 6.61 (s, 2H), 6.96 (m, 4H), 7.16 (m, 2H), 7.27 (d, 1H), 7.34 (d, 1H). HPLC (Chiracel OD, hexane/isopropanol (80:20), 1 ml/min): compound (1-7), retention time=13.09 min; compound (1-8), retention time=9.15 min; ratio of the AUCs (1-7)/(1-8)=99:1.

Reference Example 8

3-(R)-[3-(2-Methoxyphenylthio)-2-(R)-methylpropyl]amino-3,4-dihydro-2H-1,5-benzoxathiepine (1-8)

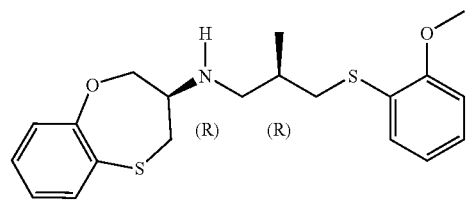

The compound (1-8) is obtained by carrying out the preparation as in example 26 but starting from the reaction mixture comprising 2-(R)-methyl-3-(2-methoxy-phenylthio)propionaldehyde (IIb-2) instead of 2-(S)-ethyl-3-(2-methoxymethoxy-3-methylphenylthio)propionaldehyde (Ve).

Yield: 58% $^1$H NMR (CDCl$_3$) δ: 1.10 (d, 3H), 1.68 (bs, 1 exchangeable H), 1.91 (m, 1H), 2.63 (dd, 1H), 2.78 (m, 2H), 2.93 (dd, 1H), 3.10 (m, 3H), 3.90 (s, 3H), 4.07 (dd, 1H), 4.23 (dd, 1H), 6.84 (d, 1H), 6.91 (m, 3H), 7.14 (m, 2H), 7.33 (m, 2H).

0.60 g (0.0016 mol) of the product (1-8) is dissolved in 3 ml of methanol and then 0.18 g (0.0015 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.72 g (0.0014 mol) of the maleate of the compound (1-8) is obtained in the form of a white solid.

M.p.: 140° C. [α]=+52.4 (c=0.254, methanol) Analysis $C_{24}H_{29}NO_6S_2$:

| Calc. %: | C 58.63 | H 5.95 | N 2.85 |
| Found:   | C 58.48 | H 5.99 | N 3.13 |

$^1$H NMR (d$_6$-DMSO) δ: 1.11 (d, 3H), 2.13 (m, 1H), 2.83 (dd, 1H), 2.98 (m, 1H), 3.06 (dd, 1H), 3.24 (m, 4H), 3.82 (s, 3H), 4.33 (bd, 1H), 4.44 (bd, 1H), 6.03 (s, 2H), 7.02 (m, 4H), 7.24 (m, 3H), 7.40 (d, 1H). HPLC (Chiralpack AS, methanol, 1 ml/min): compound (1-7), retention time=10.67 min; compound (1-8), retention time=8.81 min; ratio of the AUCs (1-8)/(1-7)=87:13.

Reference Example 9

3-(R)-[3-(2-Methoxyphenylthio)-2-(S)-ethylpropyl]amino-3,4-dihydro-2H-1,5-benzoxathiepine (1-9)

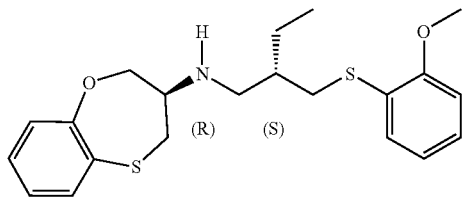

The compound (1-9) is obtained by carrying out the preparation as in example 26 but starting from the reaction mixture comprising 2-(S)-ethyl-3-(2-methoxyphenylthio)propionaldehyde (IId-1) instead of 2-(S)-ethyl-3-(2-methoxymethoxy-3-methylphenylthio)propionaldehyde (Ve).

Yield: 93% $^1$H NMR (d$_6$-DMSO) δ: 0.87 (t, 3H), 1.44 (m, 2H), 1.59 (m, 1H), 1.98 (bs, 1H), 2.64 (m, 2H), 2.82 (m, 2H), 3.04 (m, 3H), 3.80 (s, 3H), 3.93 (dd, 1H), 4.14 (dd, 1H), 6.96 (m, 4H), 7.15 (m, 2H), 7.28 (dd, 1H), 7.33 (dd, 1H).

1.1 g (0.0028 mol) of the product (1-9) are dissolved in 5 ml of methanol and then 0.29 g (0.0025 mol) of fumaric acid, dissolved in 3 ml of methanol, is added. The solution obtained is concentrated and then pentane is added. The precipitate formed is filtered off, washed with pentane and dried under vacuum at 50° C. 1.19 g (0.0023 mol) of the fumarate of the compound (1-9) are obtained in the form of a white solid.

M.p.: 86–8° C. [α]=–8 (c=0.512, methanol) Analysis C$_{25}$H$_{31}$NO$_6$S$_2$:

| Calc. %: | C 59.38 | H 6.18 | N 2.77 |
|---|---|---|---|
| Found: | C 59.32 | H 6.18 | N 2.98 |

$^1$H NMR (d$_6$-DMSO) δ: 0.87 (t, 3H), 1.44 (m, 2H), 1.63 (m, 1H), 2.68 (m, 2H), 2.85 (m, 2H), 3.02 (dd, 1H), 3.11 (m, 2H), 3.80 (s, 3H), 3.97 (dd, 1H), 4.16 (dd, 1H), 6.61 (s, 2H), 6.96 (m, 4H), 7.16 (m, 2H), 7.29 (dd, 1H), 7.34 (m, 1H). HPLC (Chiracel OD, hexane/isopropanol (95:5), 1 ml/min): compound (1-9), retention time=16.62 min; compound (1-10), retention time=14.69 min; ratio of the AUCs (1-9)/(1-10)=97:3.

Reference Example 10

3-(R)-[3-(2-Methoxyphenylthio)-2-(R)-ethylpropyl]amino-3,4-dihydro-2H-1,5-benzoxathiepine (1-10)

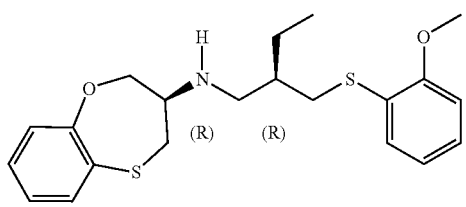

The compound (1-10) is obtained by carrying out the preparation as in example 26 but starting from the reaction mixture comprising 2-(R)-ethyl-3-(2-methoxyphenylthio)propionaldehyde (IId-2) instead of 2-(S)-ethyl-3-(2-methoxymethoxy-3-methylphenylthio)propionaldehyde (Ve).

Yield: 49% $^1$H NMR (d$_6$-DMSO) δ: 0.86 (t, 3H), 1.43 (m, 2H), 1.56 (m, 1H), 2.89 (m, 7H), 3.80 (s, 3H), 3.91 (dd, 1H), 4.14 (dd, 1H), 6.95 (m, 4H), 7.24 (m, 4H).

0.17 g (0.0044 mol) of the product (1-10) is dissolved in 3 ml of methanol and then 0.05 g (0.0043 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.15 g (0.0030 mol) of the maleate of the compound (1-10) is obtained in the form of a white solid.

M.p.: 140° C. [α]=+71.7 (c=0.318, methanol) Analysis C$_{25}$H$_{31}$NO$_6$S$_2$:

| Calc. %: | C 59.38 | H 6.18 | N 2.77 |
|---|---|---|---|
| Found: | C 59.20 | H 6.07 | N 2.93 |

$^1$H NMR (d$_6$-DMSO) δ: 0.90 (t, 3H), 1.52 (m, 2H), 1.99 (m, 1H), 3.16 (m, 7H), 3.82 (s, 3H), 4.33 (bd, 1H), 4.44 (m, 1H), 6.04 (s, 2H), 7.02 (m, 4H), 7.24 (m, 3H), 7.40 (d, 1H). HPLC (Chiracel OD, hexane/isopropanol (95:5), 1 ml/min): compound (1-10), retention time=14.01 min; compound (1-9), retention time=16.47 min; ratio of the AUCs (1-10)/(1-9)=98:2.

Reference Example 11

3-(R)-[3-(2-Methoxyphenylthio)-2-(S)-(n-propyl)propyl]amino-3,4-dihydro-2H-1,5-benzoxathiepine (1-11)

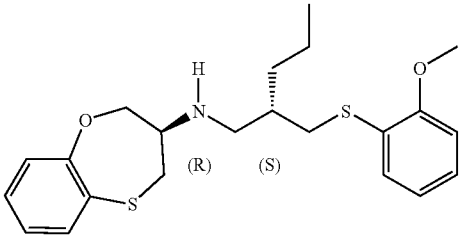

The compound (1-11) is obtained by carrying out the preparation as in example 26 but starting from the reaction mixture comprising 2-(S)-(n-propyl)-3-(2-methoxyphenylthio)propionaldehyde (IIe-1) instead of 2-(S)-ethyl-3-(2-methoxymethoxy-3-methylphenylthio)-propionaldehyde (Ve).

Yield: 80% $^1$H NMR (d$_6$-DMSO) δ: 0.85 (t, 3H), 1.33 (m, 4H), 1.65 (m, 1H), 1.96 (m, 1H), 2.63 (m, 2H), 2.82 (m, 2H), 3.03 (m, 3H), 3.80 (s, 3H), 3.92 (dd, 1H), 4.14 (dd, 1H), 6.95 (m, 4H), 7.16 (m, 2H), 7.28 (d, 1H), 7.34 (d, 1H).

0.31 g (0.0077 mol) of the product (1-11) is dissolved in 3 ml of methanol and then 0.08 g (0.0070 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.31 g (0.0060 mol) of the maleate of the compound (1-11) is obtained in the form of a white solid.

M.p.: 132–3° C. [α]=−12.7 (c=0.434, methanol) Analysis $C_{26}H_{33}NO_6S_2$:

| Calc. %: | C 60.09 | H 6.40 | N 2.70 |
|---|---|---|---|
| Found: | C 60.13 | H 6.29 | N 2.87 |

$^1$H NMR ($d_6$-DMSO) δ: 0.87 (t, 3H), 1.32 (m, 2H), 1.45 (m, 2H), 2.05 (bs, 1H), 3.13 (m, 8H), 3.82 (s, 3H), 4.33 (bd, 1H), 4.43 (bd, 1H), 6.04 (s, 2H), 7.02 (m, 4H), 7.24 (m, 3H), 7.40 (d, 1H). HPLC (Chiralpack AD, hexane/ethanol (97:3), 1 ml/min): compound (1-11), retention time=8.65 min; compound (1-12), retention time=9.16 min; ratio of the AUCs (1-11)/(1-12)=93:7.

Reference Example 12

3-(R)-[3-(2-Methoxyphenylthio)-2-(R)-(n-propyl) propyl]amino-3,4-dihydro-2H-1,5-benzoxathiepine (1-12)

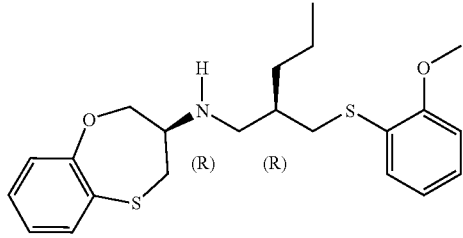

The compound (1-12) is obtained by carrying out the preparation as in example 26 but starting from the reaction mixture comprising 2-(R)-(n-propyl)-3-(2-methoxyphenylthio)propionaldehyde (IIe-2) instead of 2-(S)-ethyl-3-(2-methoxymethoxy-3-methylphenylthio)-propionaldehyde (Ve).

Yield: 47% $^1$H NMR (CDCl$_3$) δ: 0.90 (t, 3H), 1.37 (m, 2H), 1.46 (m, 2H), 1.81 (m, 1H), 2.74 (m, 2H), 3.03 (m, 5H), 3.90 (s, 3H), 4.08 (dd, 1H), 4.20 (dd, 1H), 6.84 (d, 1H), 6.94 (m, 3H), 7.14 (m, 2H), 7.34 (m, 2H).

0.16 g (0.0039 mol) of the product (1-12) is dissolved in 3 ml of methanol and then 0.04 g (0.0034 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.12 g (0.0023 mol) of the maleate of the compound (1-12) is obtained in the form of a white solid.

M.p.: 131–3° C. [α]=+63.3 (c=0.216, methanol) Analysis $C_{26}H_{33}NO_6S_2$:

| Calc. %: | C 60.09 | H 6.40 | N 2.70 |
|---|---|---|---|
| Found: | C 60.15 | H 6.56 | N 2.79 |

$^1$H NMR ($d_6$-DMSO) δ: 0.87 (t, 3H), 1.32 (m, 2H), 1.46 (m, 2H), 2.05 (bs, 1H), 3.16 (m, 8H), 3.82 (s, 3H), 4.33 (bd, 1H), 4.43 (bs, 1H), 6.04 (s, 2H), 7.02 (m, 4H), 7.24 (m, 3H), 7.40 (d, 1H). HPLC (Chiralpack AD, hexane/ethanol (97:3), 1 ml/min): compound (1-12), retention time=9.15 min; compound (1-11), retention time=8.66 min; ratio of the AUCs (1-12)/(1-11)=94:6.

Reference Example 13

3-(R)-[3-(2-Methoxyphenylthio)-2-(S)-(isopropyl) propyl]amino-3,4-dihydro-2H-1,5-benzoxathiepine (1-13)

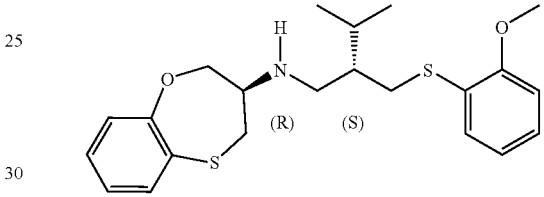

The compound (1-13) is obtained by carrying out the preparation as in example 26 but starting with the reaction mixture comprising 2-(S)-isopropyl-3-(2-methoxyphenylthio)propionaldehyde (IIf) instead of 2-(S)-ethyl-3-(2-methoxymethoxy-3-methylphenylthio)-propionaldehyde (Ve).

Yield: 70% $^1$H NMR ($d_6$-DMSO) δ: 0.88 (d, 3H), 0.90 (d, 3H), 1.46 (m, 1H), 1.92 (m, 2H), 2.65 (m, 2H), 2.82 (dd, 1H), 2.91 (m, 2H), 3.08 (m, 2H), 3.80 (s, 3H), 3.94 (dd, 1H), 4.13 (dd, 1H), 6.95 (m, 4H), 7.15 (m, 2H), 7.32 (m, 2H).

0.31 g (0.0077 mol) of the product (1-13) is dissolved in 3 ml of methanol and then 0.08 g (0.0069 mol) of maleic acid, dissolved in 2 ml of methanol, is added. The solution obtained is concentrated and then ethyl ether is added. The precipitate formed is filtered, washed with ethyl ether and dried under vacuum at 50° C. 0.32 g (0.0061 mol) of the maleate of the compound (1-13) is obtained in the form of a white solid.

M.p.: 114–5° C. [α]=−29.6 (c=0.361, methanol) Analysis $C_{26}H_{33}NO_6S_2$:

| Calc. %: | C 60.09 | H 6.40 | N 2.70 |
|---|---|---|---|
| Found: | C 60.03 | H 6.61 | N 2.83 |

$^1$H NMR ($d_6$-DMSO) δ: 0.89 (d, 3H), 0.93 (d, 3H), 1.90 (bs, 1H), 2.02 (m, 1H), 2.94 (dd, 1H), 3.06 (m, 3H), 3.30 (m, 3H), 3.81 (s, 3H), 4.32 (bd, 1H), 4.44 (bs, 1H), 6.04 (s, 3H), 6.97 (m, 2H), 7.08 (m, 2H); 7.22 (m, 2H), 7.31 (dd, 1H), 7.41 (dd, 1H).

Reference Example 14

3-(R)-[3-(2-Methoxyphenylthio)-2-(S)-methylpropyl]amino-7-methyl-3,4-dihydro-2H-1,5-benzoxathiepine (1-14)

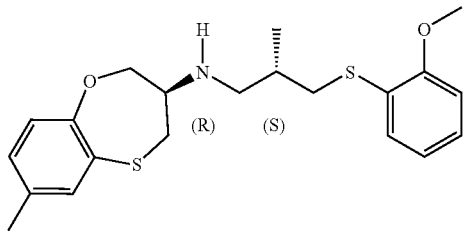

The compound (1-14) is obtained, in the form of a colorless oil, by carrying out the preparation as in example 26 but starting from the reaction mixture comprising 2-(S)-methyl-3-(2-methoxyphenylthio)propionaldehyde (IIb-1) instead of 2-(S)-ethyl-3-(2-methoxy-methoxy-3-methylphenylthio)propionaldehyde (Ve) and by using 3-(R)-amino-7-methyl-3,4-dihydro-2H-1,5-benzoxathiepine (Ib) instead of 3-(R)-amino-3,4-dihydro-2H-1,5-benzoxathiepine (Ia-1).

Yield: 36% $^1$H NMR (CDCl$_3$) δ: 1.10 (d, 3H), 1.68 (bs, 1H), 1.91 (m, 1H), 2.25 (s, 3H), 2.62 (dd, 1H), 2.77 (m, 2H), 2.92 (dd, 1H), 3.08 (m, 3H), 3.90 (s, 3H), 4.00 (dd, 1H), 4.20 (dd, 1H), 6.88 (m, 4H), 7.15 (m, 2H), 7.31 (dd, 1H).

0.22 g (0.0056 mol) of the product (1-14) is dissolved in 3 ml of methanol and then 0.065 g (0.0056 mol) of maleic acid, dissolved in 2 ml of methanol, is added. The solution obtained is concentrated and a white precipitate is formed; it is filtered off and dried under vacuum at 50° C. 0.25 g (0.0049 mol) of the maleate of the compound (1-14) is obtained in the form of a white solid.

M.p.: 148° C. [α]=12.2 (c=0.302, methanol) Analysis C$_{25}$H$_{31}$NO$_6$S$_2$:

| Calc. %: | C 59.38 | H 6.18 | N 2.77 |
|---|---|---|---|
| Found: | C 59.63 | H 6.20 | N 2.95 |

$^1$H NMR (d$_6$-DMSO) δ: 1.10 (d, 3H), 2.13 (m, 1H), 2.23 (s, 3H), 2.81 (dd, 1H), 2.97 (m, 1H), 3.09 (dd, 1H), 3.25 (m, 4H), 3.78 (bs, 1H), 3.82 (s, 3H), 4.24 (bd, 1H), 4.41 (bd, 1H), 6.04 (s, 2H), 6.99 (m, 4H), 7.19 (m, 2H), 7.28 (d, 1H).

Reference Example 15

3-(R)-[3-(2-Methoxyphenylthio)-2-(S)-methylpropyl]amino-6-methyl-3,4-dihydro-2H-1,5-benzoxathiepine (1-15)

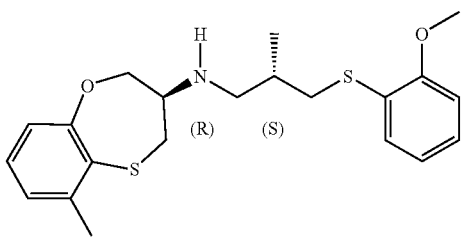

The compound (1-15) is obtained, in the form of a colorless oil, by carrying out the preparation as in example 26 but starting from the reaction mixture comprising 2-(S)-methyl-3-(2-methoxyphenylthio)propionaldehyde (IIb-1) instead of 2-(S)-ethyl-3-(2-methoxy-methoxy-3-methylphenylthio)propionaldehyde (Ve) and by using 3-(R)-amino-6-methyl-3,4-dihydro-2H,1,5-benzoxathiepine (Ic) instead of 3-(R)-amino-3,4-dihydro-2H-1,5-benzoxathiepine (Ia-1).

Yield: 23% $^1$H NMR (d$_6$-DMSO) δ: 1.00 (d, 3H), 1.75 (m, 1H), 1.99 (bs, 1H), 2.31 (s, 3H), 2.53 (m, 1H), 2.66 (m, 2H), 2.84 (dd, 1H), 3.09 (m, 3H), 3.80 (s, 3H), 3.92 (dd, 1H), 4.17 (bd, 1H), 6.81 (d, 1H), 6.94 (m, 3H), 7.02 (t, 1H), 7.15 (td, 1H), 7.27 (d, 1H).

0.10 g (0.0026 mol) of the product (1-15) is dissolved in 3 ml of methanol and then 0.03 g (0.0026 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.11 g (0.0022 mol) of the maleate of the compound (1-15) is obtained in the form of a white solid.

M.p.: 111–3° C. [α]=+16.3 (c=0.214, methanol) Analysis C$_{25}$H$_{31}$NO$_6$S$_2$:

| Calc. %: | C 59.38 | H 6.18 | N 2.77 |
|---|---|---|---|
| Found: | C 58.74 | H 6.20 | N 3.01 |

$^1$H NMR (d$_6$-DMSO) δ: 1.10 (d, 3H), 2.12 (bs, 1H), 2.33 (s, 3H), 2.81 (dd, 1H), 2.99 (bs, 1H), 3.09 (dd, 1H), 3.28 (bm, 5H), 3.82 (s, 3H), 4.39 (bm, 2H), 6.04 (s, 2H), 6.90 (d, 1H), 6.97 (m, 3H), 7.10 (t, 1H), 7.20 (td, 1H), 7.28 (dd, 1H).

Reference Example 16

3-(R)-[3-(2,3-Dihydrobenzofuran-7-thio)-2-(S)-methylpropyl]amino-3,4-dihydro-2H-1,5-benzoxathiepine (1-16)

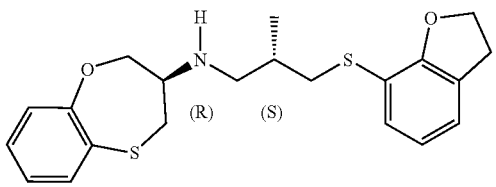

The compound (1-16) is obtained, in the form of a colorless oil, by carrying out the preparation as in example 26 but starting from the reaction mixture comprising 2-(S)-methyl-3-(2,3-dihydrobenzofuran-7-thio)propionaldehyde (IIc) instead of 2-(S)-ethyl-3-(2-methoxymethoxy-3-methylphenylthio)propionaldehyde (Ve).

Yield: 40% $^1$H NMR (d$_6$-DMSO) δ: 0.96 (d, 3H), 1.70 (m, 1H), 1.97 (bs, 1H), 2.67 (m, 4H), 3.07 (m, 3H), 3.19 (t, 2H), 3.32 (s, 3H), 3.89 (dd, 1H), 4.14 (bd, 1H), 4.54 (t, 2H), 6.79 (t, 1H), 6.97 (m, 2H), 7.08 (m, 2H), 7.17 (m, 1H), 7.33 (d, 1H).

0.20 g (0.0005 mol) of the product (1-16) is dissolved in 3 ml of methanol and 0.055 g (0.0005 mol) of maleic acid dissolved in 2 ml of methanol, is added. The solution obtained is concentrated and then ethyl ether is added. The precipitate formed is filtered off, washed with ethyl ether and dried under vacuum at 50° C. 0.15 g (0.0003 mol) of the maleate of the compound (1-16) is obtained in the form of a white solid.

M.p.: 116–8° C. [α]=+8.2 (c=0.291, methanol) Analysis $C_{25}H_{29}NO_6S_2$:

| Calc. %: | C 59.62 | H 5.80 | N 2.78 |
| --- | --- | --- | --- |
| Found: | C 59.51 | H 5.70 | N 3.06 |

$^1$H NMR (d$_6$-DMSO) δ: 1.07 (d, 3H), 2.06 (bs, 1H), 2.83 (m, 1H), 2.95 (bs, 1H), 3.08 (m, 2H), 3.21 (t, 2H), 3.25 (m, 2H), 3.79 (bs, 1H), 4.33 (bd, 1H), 4.42 (bs, 1H), 4.56 (t, 2H), 6.04 (s, 2H), 6.82 (t, 1H), 7.09 (m, 4H), 7.24 (td, 1H), 7.40 (d, 1H).

Reference Example 17

3-(R)-[3-(2-Hydroxy-3-methylphenylthio)-2-(S)-methylpropyl]amino-3,4-dihydro-2H-1,5-benzoxathiepine (1-17)

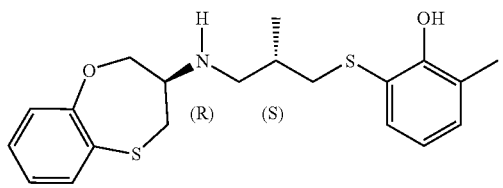

0.69 g (0.0016 mol) of 3-(R)-[3-(2-methoxymethoxy-3-methylphenylthio)-2-(S)-methylpropyl]amino-3,4-dihydro-2H-1,5-benzoxathiepine (VIb), 10 ml of methanol and 3 ml of hydrochloric acid (5N) are introduced into a 100 ml round bottomed flask. The mixture is brought to 50° C. for 12 hours. The methanol is evaporated under reduced pressure, then 3 ml of an aqueous sodium hydroxide solution (5N) are added and the mixture is extracted with dichloromethane. The combined organic phases are dried over sodium sulfate, filtered and concentrated under reduced pressure. The residue is purified by flash chromatography on silica gel (eluent: dichloromethane/methanol=99:1). 0.31 g (0.0008 mol) of the compound (1-17) is recovered in the form of a colorless oil.

Yield: 37% $^1$H NMR (d$_6$-DMSO) δ: 0.98 (d, 3H), 1.73 (m, 1H), 2.16 (s, 3H), 2.61 (m, 3H), 2.81 (dd, 1H), 2.96 (dd, 1H), 3.07 (m, 2H), 3.92 (dd, 1H), 4.15 (dd, 1H), 6.72 (t, 1H), 6.98 (m, 3H), 7.16 (m, 2H), 7.34 (d, 1H). 0.31 g (0.0008 mol) of the product (1-17) is dissolved in 3 ml of methanol and then 0.09 g (0.0008 mol) of maleic acid, dissolved in 2 ml of methanols is added. The solution obtained is concentrated and then ethyl ether is added. The precipitate formed is filtered off, washed with ethyl ether and dried under vacuum at 50° C. 0.25 g (0.0005 mol) of the maleate of the compound (1-17) is obtained in the form of a white solid.

M.p.: 124–6° C. [α]=−1.2 (c=0.255, methanol) Analysis $C_{24}H_{29}NO_6S_2$:

| Calc. %: | C 59.63 | H 5.94 | N 2.85 |
| --- | --- | --- | --- |
| Found: | C 59.23 | H 5.78 | N 2.80 |

$^1$H NMR (d$_6$-DMSO) δ: 1.09 (d, 3H), 2.07 (bs, 1H), 2.17 (s, 3H), 2.75 (dd, 1H), 2.98 (m, 2H), 3.16 (bs, 1H), 3.26 (m, 2H), 3.80 (bs, 1H), 4.35 (bd, 1H), 4.45 (bd, 1H), 6.04 (s, 2H), 6.76 (t, 1H), 7.00 (d, 1H), 7.06 (m, 2H), 7.16 (d, 1H), 7.25 (td, 1H), 7.39 (dd, 1H).

Reference Example 18

3-(R)-[3-(2-Hydroxyphenylthio)-2-(S)-methylpropyl]amino-3,4-dihydro-2H-1,5-benzoxathiepine (1-18)

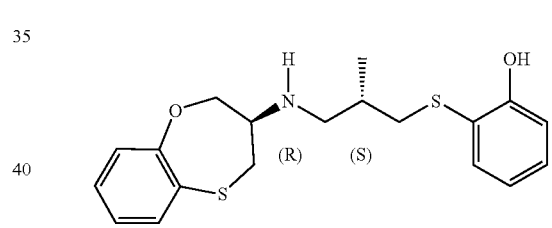

The compound (1-18) is obtained, in the form of a pale yellow oil, by carrying out the preparation as in reference example 17 but by replacing 3-(R)-[3-(2-methoxymethoxy-3-methylphenylthio)-2-(S)-methylpropyl]-amino-3,4-dihydro-2H-1,5-benzoxathiepine (VIb) with 3-(R)-[3-(2-(methoxymethoxy)phenylthio)-2-(S)-methylpropyl]amino-3,4-dihydro-2H-1,5-benzoxathiepine (VId)

Yield: 95% $^1$H NMR (d$_6$-DMSO) δ: 0.99 (d, 3H), 1.73 (m, 1H), 2.59 (m, 3H), 2.80 (m, 1H), 3.05 (m, 3H), 3.91 (dd, 1H), 4.15 (bd, 1H), 6.78 (m, 2H), 6.99 (m, 3H), 7.19 (m, 2H), 7.33 (m, 1H).

1.2 g (0.0033 mol) of the product (1-18) are dissolved in 5 ml of methanol and then 0.3 g (0.0026 mol) of maleic acid, dissolved in 3 ml of methanol, is added. The solution obtained is concentrated and then ethyl ether is added. The precipitate formed is filtered off, washed with ethyl ether and dried under vacuum at 50° C. 0.88 g (0.0018 mol) of the maleate of the compound (1-18) is obtained in the form of a white solid.

M.p.: 119–21° C. [α]=15.3 (c=0.416, methanol) Analysis $C_{23}H_{27}NO_6S_2$:

| Calc. %: | C 57.84 | H 5.70 | N 2.93 |
| --- | --- | --- | --- |
| Found: | C 57.51 | H 5.82 | N 2.80 |

$^1$H NMR (d$_6$-DMSO) δ: 1.09 (d, 3H), 2.1 (m, 1H), 2.79 (dd, 1H), 2.95 (m, 1H), 3.05 (dd, 1H), 3.18 (m, 1H), 3.29 (m, 3H), 3.81 (bs, 1H), 4.35 (bd, 1H), 4.45 (bd, 1H), 6.04 (s, 2H), 6.82 (m, 2H), 7.06 (m, 3H), 7.24 (m, 2H), 7.39 (dd, 1H).

Reference Example 19

3-(R)-[3-(2-Hydroxy-3-ethylphenylthio)-2-(S)-methylpropyl]amino-3,4-dihydro-2H-1,5-benzoxathiepine (1-19)

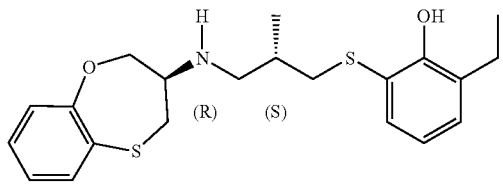

The compound (1-19) is obtained, in the form of a colorless oil, by carrying out the preparation as in reference example 17 but by replacing 3-(R)-[3-(2-methoxymethoxy-3-methylphenylthio)-2-(S)-methylpropyl]-amino-3,4-dihydro-2H-1,5-benzoxathiepine (VIb) with 3-(R)-[3-(2-methoxymethoxy-3-ethylphenylthio)-2-(S)-methylpropyl]amino-3,4-dihydro-2H-1,5-benzoxathiepine (VIe).

Yield: 33% $^1$H NMR (CDCl$_3$) δ: 1.04 (d, 3H), 1.22 (t, 3H), 1.91 (m, 1H), 2.67 (q, 2H), 2.79 (m, 4H), 3.05 (m, 2H), 3.15 (m, 1H), 4.02 (dd, 1H), 4.34 (dd, 1H), 6.77 (t, 1H), 6.98 (m, 2H), 7.13 (m, 2H), 7.32 (dd, 1H), 7.37 (dd, 1H).

0.11 g (0.0003 mol) of the product (1-19) is dissolved in 3 ml of methanol and then 0.033 g (0.00028 mol) of maleic acid, dissolved in 2 ml of methanol, is added. The solution obtained is concentrated and ethyl ether is added. The precipitate formed is filtered off, washed with ethyl ether and dried under vacuum at 50° C. 0.075 g (0.00015 mol) of the maleate of the compound (1-19) is obtained in the form of a white solid.

M.p.: 120° C. [α]=+1.4 (c=0.280, methanol) Analysis C$_{25}$H$_{31}$NO$_6$S$_2$:

| Calc. %: | C 59.38 | H 6.18 | N 2.77 |
| --- | --- | --- | --- |
| Found: | C 59.18 | H 6.28 | N 2.68 |

$^1$H NMR (d$_6$-DMSO) δ: 1.11 (m, 6H); 2.07 (bs, 1H), 2.58 (q, 2H), 2.74 (dd, 1H), 2.99 (m, 2H), 3.21 (m, 3H), 3.79 (bs, 1H), 4.34 (bd, 1H), 4.42 (bs, 1H), 6.04 (s, 2H), 6.80 (t, 1H), 7.05 (m, 3H), 7.17 (d, 1H), 7.24 (td, 1H), 7.39 (d, 1H), 8.56 (bs, 1 exchangeable H).

Reference Example 20

3-(R)-[3-(2-Hydroxy-3-methylphenylthio)-2-(S)-ethylpropyl]amino-3,4-dihydro-2H-1,5-benzoxathiepine (1-20)

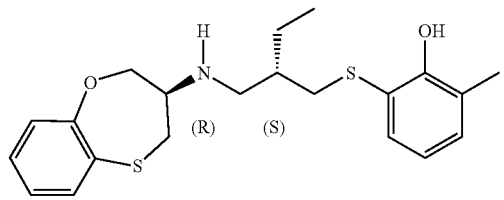

The compound (1-20) is obtained, in the form of a colorless oil, by carrying out the preparation as in reference example 17 but by replacing 3-(R)-[3-(2-methoxymethoxy-3-methylphenylthio)-2-(S)-methylpropyl]-amino-3,4-dihydro-2H-1,5-benzoxathiepine (VIb) with 3-(R)-[3-(2-methoxymethoxy-3-methylphenylthio)-2-(S)-ethylpropyl]amino-3,4-dihydro-2H-1,5-benzoxathiepine (VIa).

Yield: 91% $^1$H NMR (d$_6$-DMSO) δ: 0.85 (t, 3H), 1.42 (m, 2H), 1.57 (m, 1H), 2.16 (s, 3H), 2.66 (m, 2H), 2.85 (m, 3H), 3.07 (m, 2H), 3.94 (dd, 1H), 4.14 (dd, 1H), 6.72 (t, 1H), 6.98 (m, 3H), 7.17 (m, 2H), 7.34 (d, 1H)

0.32 g (0.0008 mol) of the product (1-20) is dissolved in 3 ml of methanol and then 0.09 g (0.0008 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.31 g (0.0006 mol) of the maleate of the compound (1-20) is obtained in the form of a white solid.

M.p.: 111–2° C. [α]=−7.8 (c=0.332, methanol) Analysis C$_{25}$H$_{31}$NO$_6$S$_2$:

| Calc. %: | C 59.38 | H 6.18 | N 2.77 |
| --- | --- | --- | --- |
| Found: | C 59.04 | H 6.28 | N 2.84 |

$^1$H NMR (d$_6$-DMSO) δ: 0.87 (t, 3H), 1.52 (m, 2H), 1.94 (bs, 1H), 2.17 (s, 3H), 3.07 (m, 6H), 3.81 (bs, 1H), 4.34 (bd, 1H), 4.43 (bd, 1H), 6.04 (s, 2H), 6.76 (t, 1H), 7.00 (d, 1H), 7.06 (m, 2H), 7.16 (d, 1H), 7.25 (td, 1H), 7.40 (d, 1H), 8.64 (bs, exchangeable H).

Reference Example 21

3-(R)-[3-(2-Hydroxy-3-methylphenylthio)-2-(S)-(isopropyl)propyl]amino-3,4-dihydro-2H-1,5-benzoxathiepine (1-21)

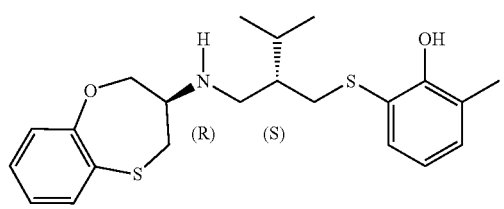

The compound (1-21), which is not purified at this stage but salified directly, is obtained by carrying out the preparation as in reference example 17 but by replacing 3-(R)-[3-(2-methoxymethoxy-3-methylphenylthio)-2-(S)-methylpropyl]amino-3,4-dihydro-2H-1,5-benzoxathiepine (VIb) with 3-(R)-[3-(2-methoxymethoxy-3-methylphenylthio)-2-(S)-(isopropyl)propyl]amino-3,4-dihydro-2H-1,5-benzoxathiepine (VIc).

Crude yield: 84%

0.083 g (0.0002 mol) of the product (1-21) is dissolved in 3 ml of methanol and then 0.024 g (0.0002 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.08 g (0.00015 mol) of the maleate of the compound (1-21) is obtained in the form of a white solid.

M.p.: 127° C. $[\alpha]$=−29.4 (c=0.211, methanol) Analysis $C_{26}H_{33}NO_6S_2$:

| Calc. %: | 60.09 | H 6.40 | N 2.70 |
|---|---|---|---|
| Found: | C 59.85 | H 6.43 | N 2.77 |

$^1$H NMR (d$_6$-DMSO) δ: 0.85 (d, 3H), 0.90 (d, 3H), 1.85 (bs, 1H), 2.01 (bs, 1H), 2.17 (s, 3H), 2.86 (dd, 1H), 2.96 (dd, 1H), 3.10 (bs, 1H), 3.29 (bs, 3H), 3.83 (bs, 1H), 4.34 (d, 1H), 4.44 (bs, 1H), 6.04 (s, 2H), 6.76 (t, 1H), 7.00 (d, 1H), 7.07 (m, 2H), 7.17 (d, 1H), 7.25 (t, 1H), 7.40 (d, 1H), 8.65 (bs, exchangeable H).

Reference Example 22

3-(R)-[3-(2-Hydroxy-3-methylphenylthio)-2-(S)-methylpropyl]amino-6-methyl-3,4-dihydro-2H-1,5-benzoxathiepine (1-22)

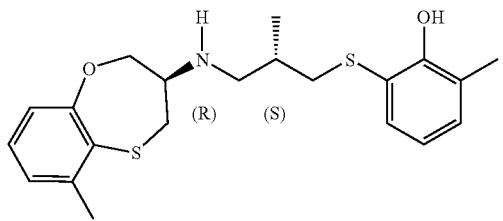

The compound (1-22) is obtained, in the form of a colorless oil, by carrying out the preparation as in reference example 17 but by replacing 3-(R)-[3-(2-methoxymethoxy-3-methylphenylthio)-2-(S)-methylpropyl]-amino-3,4-dihydro-2H-1,5-benzoxathiepine (VIb) with 3-(R)-[3-(2-methoxymethoxy-3-methylphenylthio)-2-(S)-methylpropyl]amino-6-methyl-3,4-dihydro-2H-1,5-benzoxathiepine (VIg).

Yield: 95% $^1$H NMR (d$_6$-DMSO) δ: 0.98 (d, 3H), 1.74 (m, 1H), 2.16 (s, 3H), 2.31 (s, 3H), 2.55 (m, 1H), 2.41 (m, 2H), 2.86 (m, 1H), 2.96 (dd, 1H), 3.11 (m, 2H), 3.94 (bs, 1H), 4.17 (bd, 1H), 6.72 (t, 1H), 6.81 (d, 1H), 6.92 (d, 1H), 6.97 (d, 1H), 7.03 (t, 1H), 7.14 (d, 1H).

0.315 g (0.0008 mol) of the product (1-22) is dissolved in 3 ml of methanol and then 0.084 g (0.0007 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.35 g (0.0007 mol) of the maleate of the compound (1-22) is obtained in the form of a white solid.

M.p.: 108–9° C. $[\alpha]$=+13.4 (c=0.209, methanol) Analysis $C_{25}H_{31}NO_6S_2$:

| Calc. %: | C 59.38 | H 6.18 | N 2.77 |
|---|---|---|---|
| Found: | C 59.38 | H 6.26 | N 3.00 |

$^1$H NMR (d$_6$-DMSO) δ: 1.09 (d, 3H), 2.06 (m, 1H), 2.17 (s, 3H), 2.33 (s, 3H), 2.75 (dd, 1H), 2.99 (m, 2H), 3.16 (bs, 1H), 3.27 (m, 3H), 3.79 (bs, 1H), 4.39 (m, 2H), 6.04 (s, 2H), 6.76 (t, 1H), 6.90 (d, 1H), 7.00 (m, 2H), 7.10 (t, 1H), 7.16 (d, 1H).

Reference Example 23

3-(R)-[3-(2-Hydroxy-3-methoxyphenylthio)-2-(S)-methylpropyl]amino-3,4-dihydro-2H-1,5-benzoxathiepine (1-23)

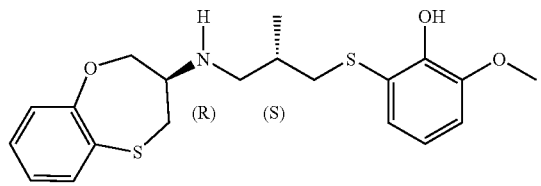

The compound (1-23), which is not purified at this stage but salified directly, is obtained by carrying out the preparation as in reference example 17 but by replacing 3-(R)-[3-(2-methoxymethoxy-3-methylphenylthio)-2-(S)-methylpropyl]amino-3,4-dihydro-2H-1,5-benzoxathiepine (VIb) with 3-(R)-[3-(2-methoxymethoxy-3-methoxyphenylthio)-2-(S)-methylpropyl]amino-3,4-dihydro-2H-1,5-benzoxathiepine (VIi).

Crude yield: 73%

0.13 g (0.0003 mol) of the product (1-23) is dissolved in 3 ml of methanol and then 0.035 g (0.0003 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.103 g (0.0002 mol) of the maleate of the compound (1-23) is obtained in the form of a white solid.

M.p.: 137–9° C. $[\alpha]$=−11.6 (c=0.268, methanol) Analysis $C_{24}H_{29}NO_7S_2$:

| Calc. %: | C 56.78 | H 5.76 | N 2.76 |
|---|---|---|---|
| Found: | C 56.82 | H 5.85 | N 2.89 |

$^1$H NMR (d$_6$-DMSO) δ: 1.08 (d, 3H), 2.07 (m, 1H), 2.79 (dd, 1H), 2.96 (m, 1H), 3.04 (dd, 1H), 3.17 (m, 1H), 3.27 (m, 3H), 3.79 (s, 3H), 4.35 (bd, 1H), 4.44 (bd, 1H), 6.04 (s, 2H), 6.77 (m, 1H), 6.86 (m, 2H), 7.06 (m, 2H), 7.24 (m, 1H), 7.39 (d, 1H), 8.79 (bs, exchangeable), 9.02 (bs, exchangeable).

Reference Example 24

3-(R)-[3-(2,3-Dimethoxyphenylthio)-2-(S)-methylpropyl]amino-3,4-dihydro-2H-1,5-benzoxathiepine (1-24)

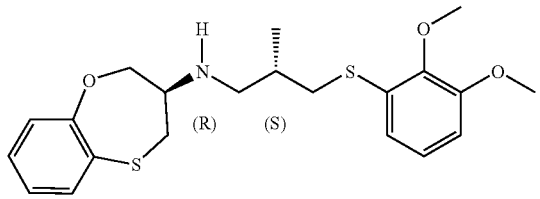

The compound (1-24) is obtained by carrying out the preparation as in example 26 but starting from the reaction mixture comprising 2-(S)-methyl-3-(2,3-dimethoxyphenylthio)propionaldehyde (IIg) instead of 2-(S)-ethyl-3-(2-methoxymethoxy-3-methylphenylthio)-propionaldehyde (Ve).

Yield: 37% $^1$H NMR (CDCl$_3$) δ: 1.00 (d, 3H), 1.78 (m, 1H), 2.02 (bs, 1H), 2.62 (m, 3H), 2.81 (dd, 1H), 3.08 (m, 3H), 3.70 (s, 3H), 3.78 (s, 3H), 3.92 (dd, 1H), 4.17 (dd, 1H), 6.86 (m, 2H), 7.01 (m, 3H), 7.17 (m, 1H), 7.33 (d, 1H).

0.22 g (0.0005 mol) of the product (1-24) is dissolved in 3 ml of methanol and then 0.057 g (0.0005 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.175 g (0.0003 mol) of the maleate of the compound (1-24) is obtained in the form of a white solid.

M.p.: 117–9° C. [α]=+1 (c=0.270, methanol) Analysis C$_{25}$H$_{31}$NO$_7$S$_2$:

| Calc. %: | C 57.56 | H 5.99 | N 2.68 |
|---|---|---|---|
| Found: | C 57.16 | H 5.82 | N 2.92 |

$^1$H NMR (d$_6$-DMSO) δ: 1.11 (d, 3H), 2.14 (bs, 1H), 2.82 (dd, 1H), 2.98 (bs, 1H), 3.11 (dd, 1H), 3.17 (bs, 1H), 3.30 (m, 3H), 3.72 (s, 3H), 3.79 (s, 3H), 4.34 (bd, 1H), 4.40 (bs, 1H), 6.89 (m, 2H), 7.06 (m, 3H), 7.25 (m, 1H), 7.40 (dd, 1H), 8.78 (bs, exchangeable H).

Reference Example 25

3-(R)-[3-(2-Hydroxy-3-(isopropyl)phenylthio)-2-(S)-methylpropyl]amino-3,4-dihydro-2H-1,5-benzoxathiepine (1-25)

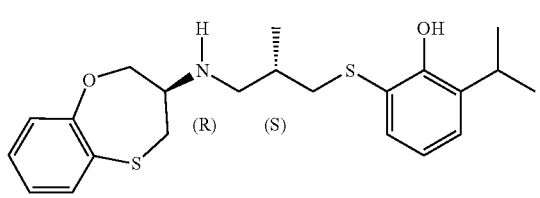

The compound (1-25) is obtained, in the form of a colorless oil, by carrying out the preparation as in reference example 17 but by replacing 3-(R)-[3-(2-methoxymethoxy-3-methylphenylthio)-2-(S)-methylpropyl]amino-3,4-dihydro-2H-1,5-benzoxathiepine (VIb) with 3-(R)-[3-(2-methoxymethoxy-3-(isopropyl)phenylthio)-2-(S)-methylpropyl]amino-3,4-dihydro-2H-1,5-benzoxathiepine (VIh).

Yield: 68% $^1$H NMR (CDCl$_3$) δ: 1.05 (d, 3H), 1.23 (d, 6H), 1.55 (bs, exchangeable H), 1.91 (m, 1H), 2.76 (m, 3H), 2.86 (dd, 1H), 3.04 (m, 2H), 3.14 (bs, 1H), 3.32 (m, 1H), 4.02 (dd, 1H), 4.33 (dd, 1H), 6.80 (m, 1H), 6.97 (m, 2H), 7.15 (m, 2H), 7.34 (m, 2H).

0.124 g (0.0003 mol) of the product (1-25) is dissolved in 3 ml of methanol and then 0.036 g (0.0003 mol) of maleic acid, dissolved in 2 ml of methanol, is added. The solution obtained is concentrated and then ethyl ether is added. The precipitate formed is filtered off, washed with ethyl ether and dried under vacuum at 50° C. 0.155 g (0.0003 mol) of the maleate of the compound (1-25) is obtained in the form of a white solid.

M.p.: 126° C. [α]=+4.1 (c=0.245, methanol) Analysis C$_{26}$H$_{33}$NO$_6$S$_2$:

| Calc. %: | C 60.09 | H 6.40 | N 2.69 |
|---|---|---|---|
| Found: | C 59.70 | H 6.33 | N 2.72 |

$^1$H NMR (d$_6$-DMSO) δ: 1.09 (d, 3H), 1.15 (d, 6H), 2.08 (m, 1H), 2.75 (dd, 1H), 2.98 (m, 2H), 3.16 (bs, 1H), 3.27 (m, 4H), 3.78 (bs, 1H), 4.34 (bd, 1H), 4.43 (bd, 1H), 6.04 (s, 2H), 6.84 (t, 1H), 7.06 (m, 3H), 7.18 (d, 1H), 7.24 (t, 1H), 7.39 (d, 1H), 8.52 (bs, exchangeable), 8.76 (bs, exchangeable).

Reference Example 26

3-(R)-[3-(2-Hydroxy-6-methylphenylthio)-2-(S)-methylpropyl]amino-3,4-dihydro-2H-1,5-benzoxathiepine (1-26)

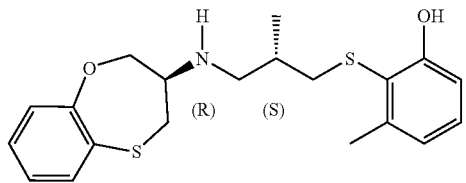

The compound (1-26) is obtained, in the form of a colorless oil, by carrying out the preparation as in reference example 17 but by replacing 3-(R)-[3-(2-methoxymethoxy-3-methylphenylthio)-2-(S)-methylpropyl]-amino-3,4-dihydro-2H-1,5-benzoxathiepine (VIb) with 3-(R)-[3-(2-methoxymethoxy-6-methylphenylthio)-2-(S)-methylpropyl]amino-3,4-dihydro-2H-1,5-benzoxathiepine (VIj).

Yield: 88% $^1$H NMR (d$_6$-DMSO) δ: 0.95 (d, 3H), 1.61 (m, 1H), 2.40 (s, 3H), 2.60 (m, 2H), 2.77 (dd, 1H), 2.88 (dd, 1H), 3.00 (m, 2H), 3.88 (dd, 1H), 4.11 (dd, 1H), 6.71 (m, 2H), 6.99 (m, 3H), 7.17 (m, 1H), 7.33 (dd, 1H).

0.39 g (0.001 mol) of the product (1-26) is dissolved in 3 ml of methanol and then 0.105 g (0.0009 mol) of maleic acid, dissolved in 2 ml of methanol, is added. The solution obtained is concentrated and then ethyl ether is added. The precipitate formed is filtered out, washed with ethyl ether and dried under vacuum at 50° C. 0.37 g (0.0007 mol) of the maleate of the compound (1-26) is obtained in the form of a white solid.

M.p.: 153–4° C. [α]=0 (c=0.2, methanol) Analysis $C_{24}H_{29}NO_6S_2$:

| Calc. %: | C 58.63 | H 5.95 | N 2.85 |
| Found: | C 58.53 | H 5.97 | N 3.04 |

$^1$H NMR (d$_6$-DMSO) δ: 1.06 (d, 3H), 1.96 (m, 1H), 2.42 (s, 3H), 2.71 (dd, 1H), 2.91 (dd, 2H), 3.15 (m, 1H), 3.24 (bs, 2H), 3.76 (bs, 1H), 4.36 (m, 2H), 6.04 (s, 2H), 6.74 (d, 2H), 7.05 (m, 3H), 7.24 (m, 1H), 7.39 (dd, 1H).

The compounds of formula (1) and their therapeutically acceptable salts exhibit advantageous pharmacological properties, in particular cardiac cytoprotective properties.

This is because they are active with regard to the cardiomyocyte by inhibiting the contraction of the rat isolated left atrium induced by veratrine and because it is accepted that veratrine slows down the inactivation of the sodium channel and produces a long-lasting sodium current which reproduces the sodium overload observed during ischemia. This pharmacological test is carried out according to the technique described in Naunyn-Schmiedeberg's Arch. Pharmacol., 1993, 348, 184 according to the following protocol.

Male Wistar rats (OFA, Iffa Credo, France) weighing 400–450 g are used. The animals are placed in quarantine for 4 to 8 days with free access to standardized laboratory food before they are used in the experiments. The animals are housed individually 24 hours before the tests. Water filtered through a 0.22 μm filter is freely available from an automatic dispenser. The quarantine area and the experimental laboratory are air-conditioned (temperature: 20±3° C.; relative humidity: 55±5%) and are illuminated from 7 a.m. to 7 p.m. All the rats are treated according to the code of ethics for laboratory animals (Guide for the Care and Use of Laboratory Animals, U.S. Department of Agriculture, Public Health Service, National Institutes of Health publication No. 85–23, Revised 1985) and the protocol (No. 31) is carried out in accordance with the recommendations of the local research animals ethics committee.

The animals are sacrificed using a lethal dose of sodium pentobarbital (50 mg/kg) administered intra-peritoneally. The thorax is opened and the left atrium is rapidly excised and mounted, in the vertical position, in an organ vessel comprising 20 ml of Krebs liquid (NaCl, 119 mmol; KCl, 5.6 mmol; MgSO$_4$, 1.17 mmol; CaCl$_2$, 2.1 mmol; NaH$_2$PO$_4$, 1 mmol; NaHCO$_3$, 25 mmol; glucose, 10 mmol; pH=7.4). The bath is maintained at a constant temperature of 34° C. while continuously bubbling in an O$_2$/CO$_2$ (95:5) mixture. The atrium is stimulated by means of an electric current with a frequency of 4 Hz (duration of the pulse 1 ms) using two electrodes (Campden, Stimulator 915, Phymep, Paris, France). The contractile force is measured using a sensor (Statham; UC2). The amplifier is connected to an MP 100 interface (Biopac Systems, Goleta, Calif., USA) and the analog signal is digitized simultaneously and analyzed (Acknowledge III, Biopac Systems). After 30 min of returning to equilibrium, a concentration of the test product or of the vehicle is introduced into the organ vessel. Fifteen minutes after the introduction of the product or of the vehicle, veratrine (100 μg/ml) is added. The systolic tension developed is measured before the introduction of the product or of the vehicle and immediately before the addition of veratrine, so as to detect any negative or positive inotropic effect of the product or vehicle. The maximum amplitude of the contraction induced by the veratrine is measured independently of time. The test product is dissolved in DMSO in an amount sufficient to obtain a mother solution with a concentration equal to 10 mmol. This mother solution is subsequently diluted with Krebs liquid to the desired concentration of test product. The highest concentration of DMSO in fine is 0.1%.

Statistical analysis of the intergroup results (product versus vehicle) is carried out by an analysis of variance ANOVA followed by a Dunett test.

The cytoprotective activity of the compounds of the invention was also demonstrated in vivo in an occlusion-reperfusion model in the anesthetized animal.

Thus, the compounds of the invention are capable of normalizing the electrical disturbances of the ECG brought about by a regional ischemia followed by a reperfusion, this being achieved without a significant effect on the hemodynamic parameters. The test in question is carried out according to the technique described in J. Cardiovasc. Pharmacol., 1995, 25, 126 according to the following protocol.

Male New Zealand rabbits (Elévage des Dombes, Romans, Chatillon-sur-Chalaronne, France) weighing 2.2 to 2.7 kg are used. The animals are placed in quarantine for 4 to 8 days with free access to standardized laboratory food before they are used in the experiments. The animals are housed individually. Water filtered through a 0.22 μm filter is freely available from an automatic dispenser. The quarantine area and the experimental laboratory are air-conditioned (temperature: 20±3° C.; relative humidity: 55±5%) and are illuminated from 7 a.m. to 7 p.m. All the animals are treated according to the code of ethics for laboratory animals (Guide for the Care and Use of Laboratory Animals, U.S. Department of Agriculture, Public Health Service, National Institutes of Health publication No. 85-23, Revised 1985) and the protocol (No. 28) is carried out in accordance with the recommendations of the local research animals ethics committee. The animals are anesthetized using sodium pentobarbital (60 mg/kg) administered intravenously (i.v.) via a catheter positioned in the vein of the ear. The animals are instrumented with respiratory assistance (683 rodent/small animal ventilator, Havard Apparatus, Les Ulis, France). The gas mixture inhaled is enriched in oxygen. The respiratory rhythm, the flow volume and the percentage of oxygen in the gas mixture are adjusted so as to keep the gases in the blood within physiological limits. A polyethylene catheter, introduced into the carotid artery, is used both for the measurements of arterial pressure and to take the samples intended for the analysis of the blood gases (ABL 510, Radiometer, Copenhagen, Denmark). Anesthesia is maintained by injections of sodium pentobarbital as required. The body temperature of the animals is kept at 38–39° C. throughout the duration of the experiment using a heating blanket (Homothermic Blanket, Havard Apparatus). The various catheters are rinsed using a sterile saline solution (0.9%) comprising heparin (150 U.I./ml). The ECG (DII derivation) is recorded in order to measure the variations in the heart rate (RR interval) and in the amplitude of the ST segment. The arterial pressure is digitized and analyzed simultaneously (Dataflow®, Crystal Biotech, Northboro, Mass.). The thorax of the animal is opened at the fourth intercostal space and the pericardium is incised so as to reveal the left coronary artery. A ligature (Vicryl®, 5/0, Ethicon, Paris, France) is passed under this artery. After examining the ECG in order to detect any signs of myocardial lesions (persistent rise of the ST segment above 0.25 mV), a period of stabilization lasting 30 min is systematically observed. Any animal showing a possible myocardial lesion is excluded from the study. The test compound or the vehicle is administered per os (p.o.), as a 1% solution in methyl-cellulose, in a proportion of 1 ml/kg via a gastric tube made of flexible rubber. Anesthesia is produced 60 min after administration of the test compound or of the vehicle. The main coronary artery is then ligated for 10 min, i.e. 60 min after anesthesia, the tension in the ligature is subsequently relaxed completely for 10 min and then reestablished at the end of the procedure. The heart is excised and perfused using a formaldehyde solution (10%). The surface not fixed by the formaldehyde is regarded as the surface at risk.

The parameters measured in the experiment are:
the systolic and diastolic arterial pressure;
the heart rate (measured from the RR intervals);
the amplitude of the ST segment.

All the parameters mentioned above are measured preocclusion, 5 min and 10 min postocclusion and then 5 min, 10 min and 20 min after reperfusion.

The results obtained for some compounds of formula (1), given as nonlimiting examples, and those obtained for the derivative R 56865 (blocker of noninactivated sodium channels), atenolol (β-blocker) and diltiazem (blocker of calcium channels), chosen as reference product, are reported in the table below:

| Compound or control | Contraction with veratrine Inhibition $IC_{50}$ | ST segment % inhibition at 2.5 mg/kg p.o. | Arterial pressure % variation | Heart rate % variation |
| --- | --- | --- | --- | --- |
| 1-1 | 0.64 | 85 | 8 | 2 |
| 1-7 | 0.14 | 69 | 5 | 0 |
| R 56865 | 0.25 | 0 | — | — |
| Atenolol | >10 | 49 | −9 | −13 |
| Diltiazem | >10 | 30 | −27 | −5 |

The results of the tests therefore show that the compounds of formula (1);
oppose the long-lasting sodium current induced by veratrine;
tend to normalize the electrical disturbances in the ECG brought about by a regional ischemia followed by a reperfusion.

The in vitro activity of these compounds of the invention is of the same order of magnitude as that of the product R 56865, atenolol and diltiazem being inactive in this test.

The in vivo activity of these compounds of the invention is much greater than that of all the control products (R 56865, atenolol and diltiazem). Furthermore, it should be pointed out that, at the dose of 2.5 mg/kg administered by the oral route, these products of the invention effectively inhibit the raising of the ST segment without significantly modifying the heart rate and the arterial pressure, contrary to the control products active in this model (atenolol and diltiazem).

The molecules of the invention thus oppose the sodium overload by specifically interacting at the noninactivated sodium channel. They show an in vivo cardioprotective activity in the absence of hemodynamic effect.

For this reason, the compounds of the invention and their therapeutically acceptable salts are potentially of use as medicaments, in particular in the field of cardiology, especially in the treatment of certain cardiovascular pathologies, such as, for example, cardiac ischemia, stable angina, unstable angina, cardiac insufficiency, myocardial infarction, cardiac rhythm disorders or long QT syndrome of congenital origin.

The compounds of the invention, which can also possess a sufficient activity in modulating neuronal sodium channels and which have appropriate pharmacokinetic properties, may be active with regard to the central and/or peripheral nervous system. Consequently, some compounds of the invention are regarded as also being able to be of use in the treatment of diseases or disorders such as, for example, cerebral ischemia, transitory ischemic attack, neuropathies of a traumatic or ischemic nature, neurodegenerative diseases (Trends in Pharmacological Science, 1995, 16, 309; Clin. Exp. Pharmacol. Physiol., 2000, 27(8), 569), epilepsy and pain of neuropathic origin (Brain Res., 2000, 871(1), 98).

The compounds of the invention can be administered orally, nasally, sublingually, rectally or parenterally. Two preparations of the compounds of the invention are given hereinafter as nonlimiting formulation examples. The ingredients, and others, which are therapeutically acceptable can be introduced in other proportions without altering the scope of the invention. The terms "active ingredient" used in the formulation examples hereinbelow refer to a compound of formula (1) or an addition salt or optionally a hydrate of an addition salt of the compound of formula (1) with a pharmaceutically acceptable inorganic acid or organic acid.

Formulation Example 1

Tablets

| | |
| --- | --- |
| Active ingredient | 100 g |
| Lactose | 570 g |
| Corn starch | 200 g |
| Sodium lauryl sulfate | 5 g |
| Polyvinylpyrrolidone | 10 g |
| Microcrystalline cellulose | 100 g |
| Saturated vegetable oil | 15 g | i.e. 10,000 tablets, each comprising 10 mg of the active ingredient.

Formulation Example 2

Injectable Solution

| | |
| --- | --- |
| Active ingredient | 10 mg |
| Acetic acid | 20 mg |
| Sodium acetate | 5.9 mg |
| Sterile distilled water | q.s. for 2 ml |
| Sterile bottle or vial. | |

APPENDIX 1
Scheme A
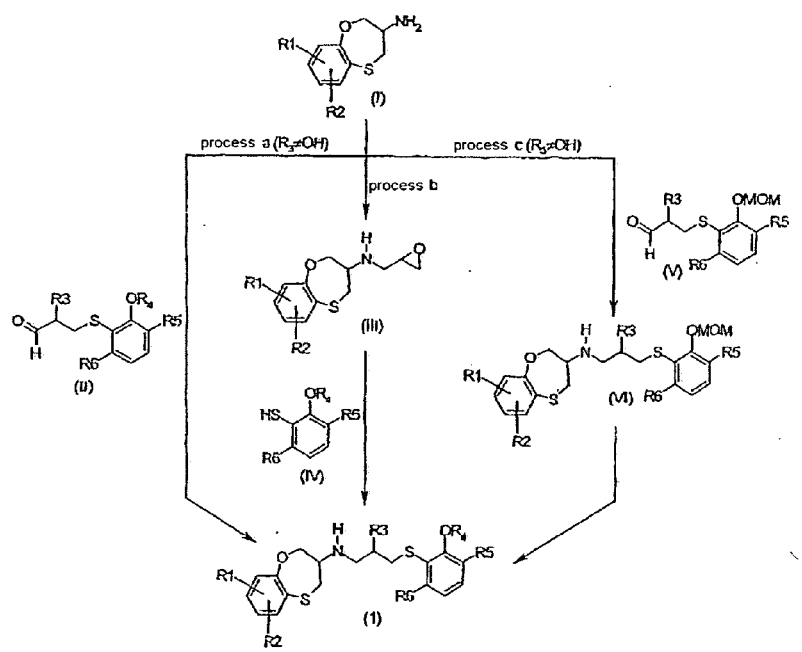

APPENDIX 2
Scheme B
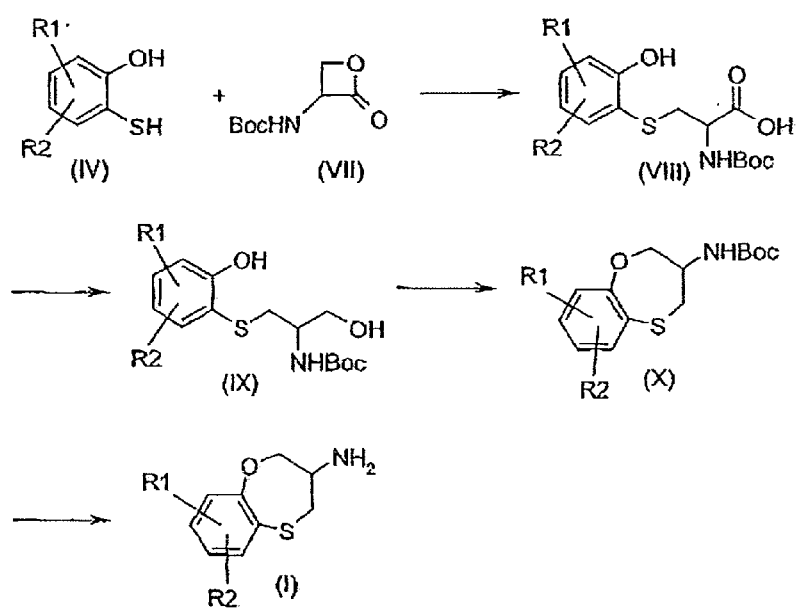

APPENDIX 3
Scheme C
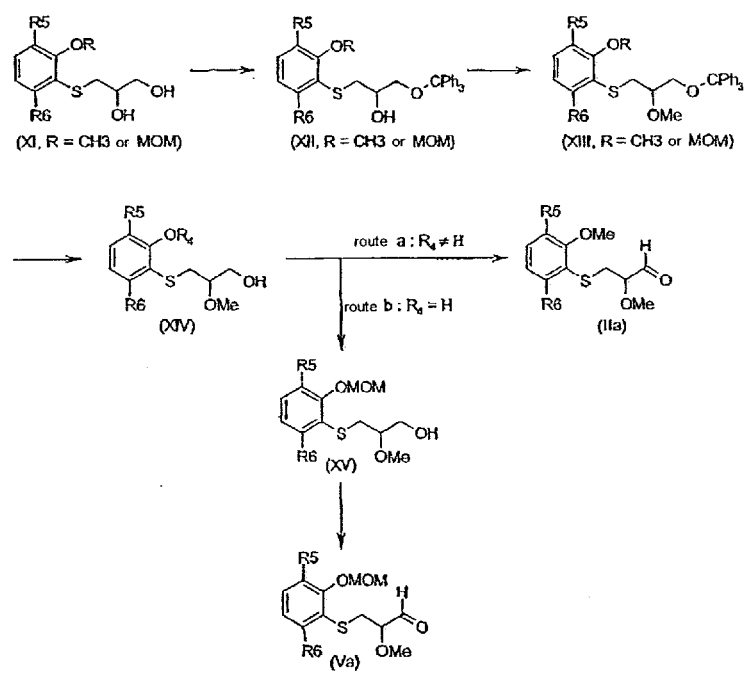

APPENDIX 4
Scheme D
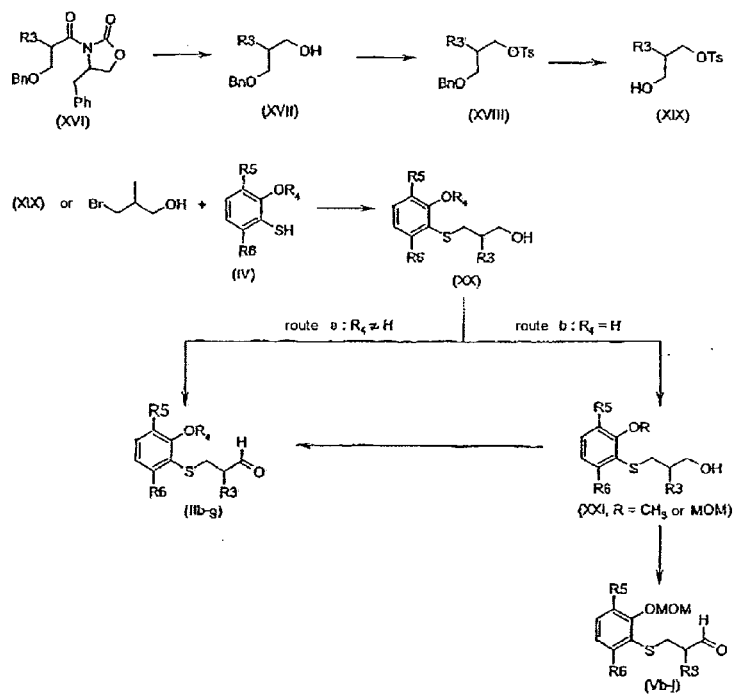

What is claimed is:

1. A 3-arylthiopropylamino-3,4-dihydro-2H-1,5-aryloxathiepine derivative of general formula (1)

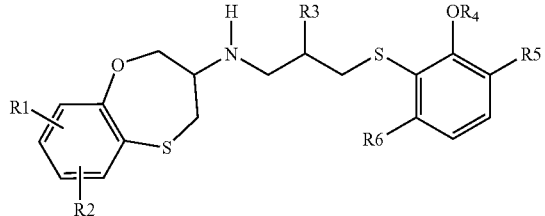

(1)

wherein:
R$_1$ and R$_2$, which are identical or different, represent:
  a hydrogen atom;
  a fluorine atom or a chlorine atom;
  a hydroxyl group;
  a linear or branched (C$_1$–C$_3$) alkyl;
  a cyclopropyl radical;
  a cyclopropoxy radical;
R$_3$ represents:
  a linear or branched (C$_1$–C$_3$) alkyl radical;
  a hydroxyl group or a methoxy radical;
R$_4$ represents:
  a hydrogen atom or a methyl radical; and
R$_5$ and R$_6$, which are identical or different, represent:
  a hydrogen atom;
  a linear or branched (C$_1$–C$_3$) alkyl radical;
  a linear or branched (C$_1$–C$_3$) alkoxy radical;
  a linear or branched (C$_1$–C$_3$) alkylthio radical;
  an alkylamino radical;
provided that, when R$_4$ represents a methyl radical, then R$_5$ represents a hydrogen atom, a (C$_1$–C$_3$) alkoxy radical, a linear or branched (C$_1$–C$_3$) alkylthio radical or an alkylamino radical,
its addition salts and the hydrates of these addition salts with pharmaceutically acceptable inorganic acids or pharmaceutically acceptable organic acids,
and its tautomeric forms, the enantiomers and the mixtures of enantiomers, and the stereoisomers, pure or as a racemic or nonracemic mixture.

2. The derivative of claim 1, wherein:
R$_1$ and R$_2$, which are identical or different, represent:
  a hydrogen atom;
  a fluorine atom or a chlorine atom;
  a hydroxyl group;
  an alkyl radical selected from methyl, ethyl, propyl and isopropyl radicals;
  a cyclopropyl radical;
  an alkoxy radical selected from methoxy, ethoxy, propoxy and isopropoxy radicals;
  a cyclopropoxy radical;
R$_3$ represents;
  an alkyl radical selected from methyl, ethyl, propyl and isopropyl radicals;
  a hydroxyl group or a methoxy radical;
R$_4$ represents:
  a hydrogen atom or a methyl radical; and
R$_5$ and R$_6$, which are identical or different, represent:
  a hydrogen atom;
  an alkyl radical selected from methyl, ethyl and isopropyl radicals;
  an alkoxy radical selected from methoxy, ethoxy, propoxy and isopropoxy radicals;
  an alkylthio radical selected from methylthio, ethylthio and isopropylthio radicals;
  an alkylamino radical selected from N-methylamino and N,N-dimethylamino radicals;
its addition salts and the hydrates of these addition salts with pharmaceutically acceptable inorganic acids or pharmaceutically acceptable organic acids,
and its tautomeric forms, the enantiomers and the mixtures of enantiomers, and the stereoisomers, pure or as a racemic or nonracemic mixture.

3. The derivative of claim 1, selected from
3-[3-(2-methoxyphenylthio)-2-methoxypropyl]amino-3,4-dihydro-2H-1,5-benzoxathiepine;
3-[3-(2-methoxyphenylthio)-2-hydroxypropyl]amino-3,4-dihydro-2H-1,5-benzoxathiepine;
3-[3-(2-hydroxyphenylthio)-2-hydroxypropyl]amino-3,4-dihydro-2H-1,5-benzoxathiepine;
3-[3-(2-methoxyphenylthio)-2-methylpropyl]amino-3,4-dihydro-2H-1,5-benzoxathiepine;
3-[3-(2-methoxyphenylthio)-2-ethylpropyl]amino-3,4-dihydro-2H-1,5-benzoxathiepine;
3-[3-(2-methoxyphenylthio)-2-(n-propyl)propyl]amino-3,4-dihydro-2H-1,5-benzoxathiepine;
3-[3-(2-methoxyphenylthio)-2-(isopropyl) propyl]amino-3,4-dihydro-2H-1,5-benzoxathiepine;
3-[3-(2-methoxyphenylthio)-2-methylpropyl]amino-7-methyl-3,4-dihydro-2H-1,5-benzoxathiepine;
3-[3-(2-methoxyphenylthio)-2-methylpropyl]amino-6-methyl-3,4-dihydro-2H-1,5-benzoxathiepine;
3-[3-(2-hydroxy-3-methylphenylthio)-2-methylpropyl]-amino-3,4-dihydro-2H-1,5-benzoxathiepine;
3-[3-(2-hydroxyphenylthio)-2-methylpropyl]amino-3,4-dihydro-2H-1,5-benzoxathiepine;
3-[3-(2-hydroxy-3-ethylphenylthio)-2-methylpropyl]-amino-3,4-dihydro-2H-1,5-benzoxathiepine;
3-[3-(2,3-dihydrobenzofuran-7-thio)-2-methylpropyl]-amino-3,4-dihydro-2H-1,5-benzoxathiepine;
3-[3-(2-hydroxy-3-methylphenylthio)-2-ethylpropyl]-amino-3,4-dihydro-2H-1,5-benzoxathiepine;
3-[3-(2-hydroxy-3-methylphenylthio)-2-(isopropyl)-propyl]amino-3,4-dihydro-2H-1,5-benzoxathiepine;
3-[3-(2-hydroxy-3-methylphenylthio)-2-methylpropyl]-amino-6-methyl-3,4-dihydro-2H-1,5-benzoxathiepine;
3-[3-(2-hydroxy-3-methoxyphenylthio)-2-methylpropyl]-amino-3,4-dihydro-2H-1,5-benzoxathiepine;
3-[3-(2,3-dimethoxyphenylthio)-2-methylpropyl]amino-3,4-dihydro-2H-1,5-benzoxathiepine;
3-[3-(2-hydroxy-3-(isopropyl)phenylthio)-2-methylpropyl]amino-3,4-dihydro-2H-1,5-benzoxathiepine;
3-[3-(2-hydroxy-6-methylphenylthio)-2-methylpropyl]-amino-3,4-dihydro-2H-1,5-benzoxathiepine,
its addition salts and the hydrates of these addition salts with pharmaceutically acceptable inorganic acids or pharmaceutically acceptable organic acids,
and its tautomeric forms, the enantiomers and the mixtures of enantiomers, and the stereoisomers, pure or as a racemic or nonracemic mixture.

4. A process for the preparation of the compound of general formula (1) of claim 1 in which R$_3$ represents a linear or branched (C$_1$–C$_3$) alkyl radical or a methoxy radical and R$_4$ represents a methyl radical, wherein an amine of formula (I)

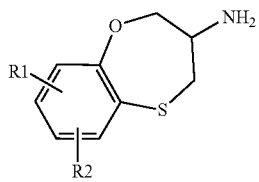

in which $R_1$ and $R_2$ are as defined in claim 1, or one of its salts, is reacted with an aldehyde of formula (II)

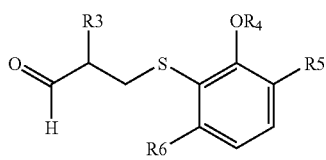

in which $R_3$ represents a linear or branched ($C_1$–$C_3$) alkyl radical or a methoxy radical, $R_4$ represents a methyl radical and $R_5$ and $R_6$ are as defined in claim 1, in the presence of a reducing agent and at a temperature of between −20° C. and +25° C., to give a compound of formula (1)

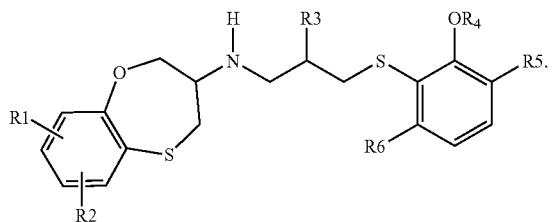

5. A process for the preparation of the compound of general formula (1) of claim 1 in which $R_3$ represents a linear or branched ($C_1$–$C_3$) alkyl radical or a methoxy radical and $R_4$ represents a hydrogen atom, wherein an amine of formula (I)

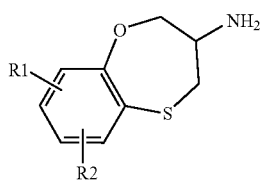

in which $R_1$ and $R_2$ are as defined in claim 1, or one of its salts, is reacted with a compound of formula (V)

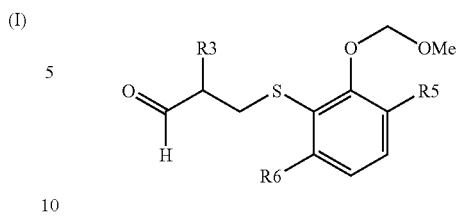

in which $R_3$ represents a linear or branched ($C_1$–$C_3$) alkyl radical or a methoxy radical and $R_5$ and $R_6$ are as defined in claim 1, in the presence of a reducing agent and at a temperature of between −20° C. and +25° C., to give a compound of formula (VI)

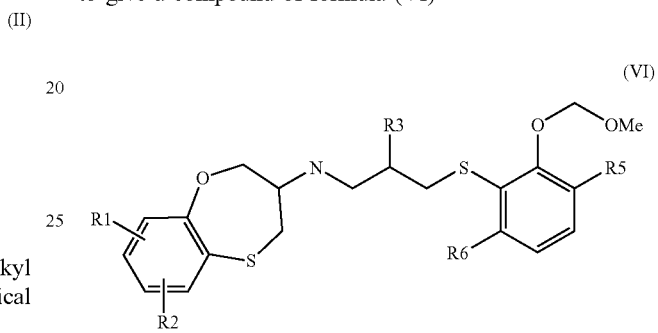

which is hydrolyzed to give a compound of formula (1)

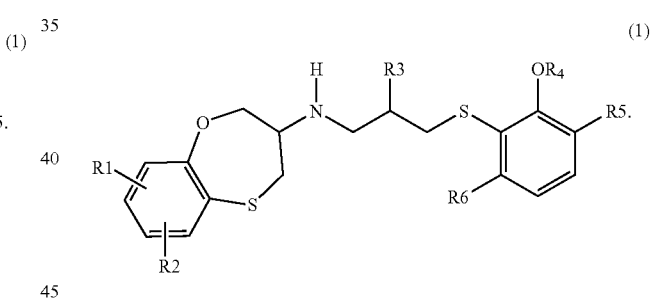

in which $R_3$ represents a linear or branched ($C_1$–$C_3$) alkyl radical or a methoxy radical and $R_4$ a hydrogen atom.

6. A process for the preparation of the compound of general formula (1) of claim 1 in which $R_3$ is a hydroxyl group, wherein an epoxide of formula (III)

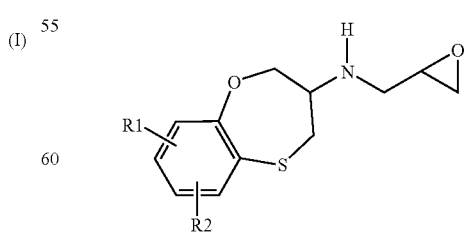

in which $R_1$ and $R_2$ are as defined in claim 1, is reacted with an arylthiol of formula (IV)

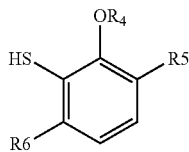

(IV)

in which R$_4$, R$_5$ and R$_6$ are as defined in claim 1, in a protic solvent, in the presence of an inorganic base and at a temperature of between 20° C. and 70° C., to give a compound of formula (1)

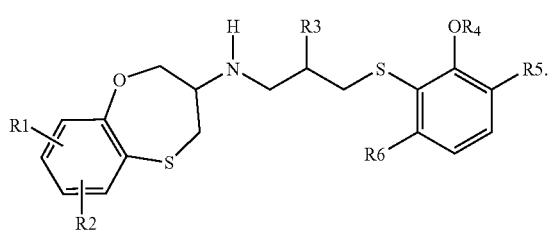

(1)

in which R$_1$, R$_2$, R$_4$, R$_5$ and R$_6$ are as defined in claim 1 and R$_3$ is a hydroxyl group.

7. The derivative of general formula (1) of claim 1, which has the (R) absolute configuration at the C(3) asymmetric carbon atom of the 3,4-dihydro-2H-1,5-benzoxathiepine fragment and the (S) absolute configuration at the asymmetric carbon atom which carries the R$_3$ group.

8. The derivative of claim 7, which is selected from the following stereoisomers:

3-(R)-[3-(2-methoxyphenylthio)-2-(S)-methoxypropyl]-amino-3,4-dihydro-2H-1,5-benzoxathiepine;
3-(R)-[3-(2-methoxyphenylthio)-2-(S)-hydroxypropyl]-amino-3,4-dihydro-2H-1,5-benzoxathiepine;
3-(R)-[3-(2-hydroxyphenylthio)-2-(S)-hydroxypropyl]-amino-3,4-dihydro-2H-1,5-benzoxathiepine;
3-(R)-[3-(2-methoxyphenylthio)-2-(S)-methylpropyl]-amino-3,4-dihydro-2H-1,5-benzoxathiepine;
3-(R)-[3-(2-methoxyphenylthio)-2-(S)-ethylpropyl]amino-3,4-dihydro-2H-1,5-benzoxathiepine;
3-(R)-[3-(2-methoxyphenylthio)-2-(S)-(n-propyl)propyl]-amino-3,4-dihydro-2H-1,5-benzoxathiepine;
3-(R)-[3-(2-methoxyphenylthio)-2-(S)-(isopropyl)-propyl]amino-3,4-dihydro-2H-1,5-benzoxathiepine;
3-(R)-[3-(2-methoxyphenylthio)-2-(S)-methylpropyl]-amino-7-methyl-3,4-dihydro-2H-1,5-benzoxathiepine;
3-(R)-[3-(2-methoxyphenylthio)-2-(S)-methylpropyl]-amino-6-methyl-3,4-dihydro-2H-1,5-benzoxathiepine,
3-(R)-[3-(2-hydroxy-3-methylphenylthio)-2-(S)-methylpropyl]amino-3,4-dihydro-2H-1,5-benzoxathiepine;
3-(R)-[3-(2-hydroxyphenylthio)-2-(S)-methylpropyl]-amino-3,4-dihydro-2H-1,5-benzoxathiepine;
3-(R)-[3-(2-hydroxy-3-ethylphenylthio)-2-(S)-methylpropyl]amino-3,4-dihydro-2H-1,5-benzoxathiepine;
3-(R)-[3-(2,3-dihydrobenzofuran-7-thio)-2-(S)-methylpropyl]amino-3,4-dihydro-2H-1,5-benzoxathiepine;
3-(R)-[3-(2-hydroxy-3-methylphenylthio)-2-(S)-ethylpropyl]amino-3,4-dihydro-2H-1,5-benzoxathiepine;
3-(R)-[3-(2-hydroxy-3-methylphenylthio)-2-(S)-(isopropyl)-propyl]amino-3,4-dihydro-2H-1,5-benzoxathiepine;
3-(R)-[3-(2-hydroxy-3-methylphenylthio)-2-(S)-methylpropyl]amino-6-methyl-3,4-dihydro-2H-1,5-benzoxathiepine;
3-(R)-[3-(2-hydroxy-3-methoxyphenylthio)-2-(S)-methylpropyl]amino-3,4-dihydro-2H-1,5-benzoxathiepine;
3-(R)-[3-(2,3-dimethoxyphenylthio)-2-(S)-methylpropyl]-amino-3,4-dihydro-2H-1,5-benzoxathiepine;
3-(R)-[3-(2-hydroxy-3-isopropylphenylthio)-2-(S)-methylpropyl]amino-3,4-dihydro-2H-1,5-benzoxathiepine;
3-(R)-[3-(2-hydroxy-6-methylphenylthio)-2-(S)-methylpropyl]amino-3,4-dihydro-2H-1,5-benzoxathiepine, their addition salts and the hydrates of these addition salts with pharmaceutically acceptable inorganic acids or pharmaceutically acceptable organic acids, and their tautomeric forms, the enantiomers and the mixtures of enantiomers, and the stereoisomers, pure or as a racemic or nonracemic mixture.

9. A compound as claimed in claim 1 as medicament.

10. A pharmaceutical composition, comprising, as active ingredient, at least one compound of claim 1 in combination with an inert pharmaceutical carrier or other pharmaceutically acceptable vehicles.

11. A method of treating a living animal body afflicted with stable angina, unstable angina, cardiac insufficiency, long QT syndrome of congenital origin, myocardial infarction and cardiac rhythm disorders, comprising the step of administering an amount of a compound of claim 1, which is effective for alleviation of such condition.

12. A method of treating a living animal body afflicted with cerebral ischemia, transitory ischemic attack, neuropathies of a traumatic or ischemic nature, and epilepsy, comprising the step of administering an amount of a compound of claim 1, which is effective for alleviation of such condition.

13. A method of treating a living animal body afflicted with pain of neuropathic origin and of neurodegenerative diseases, comprising the step of administering an amount of a compound of claim 1, which is effective for alleviation of such condition.

* * * * *

UNITED STATES PATENT AND TRADEMARK OFFICE
CERTIFICATE OF CORRECTION

| | | |
|---|---|---|
| PATENT NO. | : 7,109,234 B2 | Page 1 of 1 |
| APPLICATION NO. | : 10/472728 | |
| DATED | : September 19, 2006 | |
| INVENTOR(S) | : Bernard Vacher et al. | |

It is certified that error appears in the above-identified patent and that said Letters Patent is hereby corrected as shown below:

Title Page, #75 Inventors: "Florence Castan-Cuisat" should be --Florence Castan-Cuisiat--.

Signed and Sealed this

Sixth Day of March, 2007

JON W. DUDAS
*Director of the United States Patent and Trademark Office*